(12) United States Patent
Uhl et al.

(10) Patent No.: US 11,987,564 B2
(45) Date of Patent: May 21, 2024

(54) PTPRD INHIBITORS AND USES THEREOF

(71) Applicant: United States Government as represented by the Department of Veterans Affairs, Washington, DC (US)

(72) Inventors: George Richard Uhl, Albuquerque, NM (US); Ian M. Henderson, Sandia Park, NM (US); Wei Wang, Tucson, AZ (US); Thomas Prisinzano, Lexington, KY (US)

(73) Assignees: Arizona Board of Regents on Behalf of the University of Arizona, Tucson, AZ (US); The United States Government as respresented by the Department of Veterans Affairs, Washington, DC (US); The University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 17/734,897

(22) Filed: May 2, 2022

(65) Prior Publication Data

US 2022/0380332 A1 Dec. 1, 2022

Related U.S. Application Data

(60) Provisional application No. 63/182,532, filed on Apr. 30, 2021.

(51) Int. Cl.
*C07D 311/54* (2006.01)
*C07D 405/12* (2006.01)
*C07D 409/12* (2006.01)
*C07D 417/12* (2006.01)

(52) U.S. Cl.
CPC .......... *C07D 311/54* (2013.01); *C07D 405/12* (2013.01); *C07D 409/12* (2013.01); *C07D 417/12* (2013.01)

(58) Field of Classification Search
CPC .. C07D 311/54; C07D 405/12; C07D 409/12; C07D 417/12; A61K 31/352
See application file for complete search history.

(56) References Cited

U.S. PATENT DOCUMENTS

2012/0225864 A1   9/2012   Gan

FOREIGN PATENT DOCUMENTS

| CN | 1911925 | 2/2007 |
| WO | WO 2019/246262 | 12/2019 |
| WO | PCT/US2021/044008 | 7/2021 |
| WO | WO2022/026894 | 2/2022 |
| WO | PCT/US22/27318 | 5/2022 |

OTHER PUBLICATIONS

Banker et al., Prodrugs, Modern Pharmaceutics, Third Edition, Revised and Expanded, pp. 451 and 596 (1996).*
Bundgaard, Design of Prodrugs, p. 1, 1985.*
Silverman, Prodrugs and Drug Delivery Systems, The Organic Chemistry of Drug Design and Drug Action, pp. 352-399, 1992.*
Wolff, Some consideration for prodrug design, Burger's Medicinal Chemistry and Drug Discovery, 5th Edition, vol. 1: Principles and Practice, pp. 975-977, 1995.*
Jordan, V.C., Tamoxifen: A most unlikely pioneering medicine, Nature Reviews: Drug Discovery, vol. 2, 2003, pp. 205-213.*
Ling et al., CAPLUS Abstract 155:52258 (2011).*
Uhl et al., Cocaine reward is reduced by decreased expression of receptor-type protein tyrosine phosphatase D (PTPRD) and by a novel PTPRD antagonist, PNAS vol. 115, No. 45, pp. 11597-11602 (Nov. 2018).*
Association for Frontotemporal Degeneration 2023 (3 pages).
Baell (2016) "Feeling Nature's PAINS: Natural Products, Natural Product Drugs, and Pan Assay Interference Compounds (Pains)" J. Nat. Prod. 79, 616-628.
Bisson (2016) "Can Invalid Bioactives Undermine National Product-Based Drug Discovery?" J. Med Chem. 59: 167-1690.
Cavallini et al., "An unbiased approach to identifying tau kinases that phosphorylate tau at sites associated with Alzheimer disease." J. Biol. Chem. 288, 23331-23347 (2013).
Chow et al. Phosphorylation of FE65 Ser610 by serum- and glucocorticoid-induced kinase 1 modulates Alzheimer's disease amyloid precursor protein processing, Biochem. J., 2015, 470, 303-317.
Congdon, E. M. Sigurdsson, "Tau-targeting therapies for Alzheimer disease." Nat. Rev. Neurol. 14, 399-415 (2018).
Corticobasal Degeneration 2022 (5 pages).
Dai (2006) "Fruit and Vegetable Juices and Alzheimer's Disease: the Kame Project" the American Journal of Medicine 119, 751-759.
Dhavan, L. H. Tsai, A decade of CDK5. Nat. Rev. Mol. Cell Biol. 2, 749-759 (2001).
Drink Orange Juice Daily to Stave off Alzheimer's (Aug. 19, 2011) The Indian Express, https://indianexpress.com/article/lifestyle/health/drink-orange-juice-to-stave-off-alzheimers/.
Ferrer, I. et al., "Glycogen synthase kinase-3 is associated with neuronal and glial hyperphosphorylated tau deposits in Alzheimer's disease, Pick's disease, progressive supranuclear palsy and corticobase degeneration" Acta Neurophathol 104:583-591 (2002).
Giannakopoulos, P. G. Gold, A. von Gunten, P. R. Hof, C. Bouras, "Pathological substrates of cognitive decline in Alzheimer's disease." Front Neurol. Neurosci. 24, 20-29 (2009).
Gjevre, J.A. et al., "Restless Legs Syndrome as a Comorbidity in Rheumatoid Arthritis" Autoimmune Diseases vol. 2013 Article ID 352782.

(Continued)

*Primary Examiner* — Deepak R Rao
(74) *Attorney, Agent, or Firm* — Ballard Spahr LLP

(57) ABSTRACT

Disclosed are small molecule PTPRD inhibitors and uses thereof. Methods of using the PTPRD inhibitors include methods of treating, preventing, or delaying the progression of a disorder responsive to PTPRD inhibition, including for example nicotine dependence, addiction, obesity, metabolic syndrome, and substance-use disorders such as stimulant-use disorders and opioid-use disorders.

16 Claims, No Drawings

(56) References Cited

OTHER PUBLICATIONS

Haleagrahara, N. et al., "Therapeutic effect of quercetin in collagen-induced arthritis" Biomedicene and Pharmacology 90 38-46 (2017).

Hara (2019) "Translating of the Biology of Aging into Novel Therapeutics for Alzheimer Disease," Neurology 92: 84-93.

Hughes, E. Nikolakaki, S. E. Plyte, N. F. Totty, J. R. Woodgett, "Modulation of the glycogen synthase kinase-3 family by tyrosine phosphorylation." EMBO J 12, 803-808 (1993).

Inoue et al., Serum- and glucocorticoid-inducible kinases in migroglia, Biochemical and Biophysical Research Communications, 478, 1, 2016, 53-59.

Kimura, K. Ishiguro, S. Hisanaga, "Physiological and pathological phosphorylation of tau by Cdk5." Front Mol. Neurosci. 7, 65 (2014).

Kobayashi et al., "Phosphorylation of cyclin-dependent kinase 5 (Cdk5) at Tyr-15 is inhibited by Cdk5 activators and does not contribute to the activation of Cdk5." J Biol Chem 289, 19627-19636 (2014).

Lang F., (Patho)physiological significance of the serum- and glucocorticoid-inducible kinase isoforms, Physiol. Rev., 2006, 1151-1178.

Lauretti, O. Dincer, D. Pratico, "Glycogen synthase kinase-3 signaling in Alzheimer's disease." Biochim. Biophys. Acta. Mol. Cell Res. 1867, 118664 (2020).

Ling, Q. et al., "Synthesis and LAR inhibition of 7-alkoxy analogues of illudalic acid" Acta pharmaceutica Sinica 45(11):1385-97.

Miranda (2006) "Differential Effects of Flavonoids on Bovine Kidney Low Molecular Mass Protein Tryosine Phosphatase." Journal of Enzyme Inhibition and Medicinal Chemistry, 21(4): 419-425.

Murai (1996) "Tyrosine Dephosphorylation of Glycogen Synthase Kinase-3 is Involved in its Extracellular Signal-Dependent Inactivation," FEBS Letters 392, 153-160.

Pulido (1995), "Molecular Characterization of the Human Transmembrane Protein-Tyrosine Phosphatase" The Journal of Biological Chemistry, vol. 270, No. 12, 6722-6728.

Raveh, et al. (2011), Rosetta FlexPepDock ab-initio: simultaneous folding, docking and refinement of peptides onto their receptors. PloS one 6, e18934.

Selner et al., "Diverse levels of sequence selectivity and catalytic efficiency of protein-tyrosine phosphatases." Biochemistry 53, 397-412 (2014).

Shah, D. K. Lahiri, "Cdk5 activity in the brain—multiple paths of regulation." J Cell Sci. 127, 2391-2400 (2014).

Suganthy "Bioactive Effects of Quercetin in the Central Nervous System: Focusing on the Mechanisms of Actions," Biomedicine and Pharmacotherapy, 84: 892-908.

Tsai, R.M. and Boxer, A.L. "Treatment of Frontotemporal Dementia" Curr. Treat. Options Neurol. 16:319 (2014).

Uhl et al., Cocaine reward id reduced by decreased expression of receptor-type protein tyrosine phosphatase D (PTPRD) and by a novel PTPRD antagonist, Proc Natl Acad Sci USA 115, 11597-11602 (2018).

Vavoura (2022) "Characterization and Differentiation of Fresh Orange Juice Variety Based on Conventional Physicochemical Parameters, Flavonoids, and Volatile Compounds Using Chemometrics "Molecules, 27, 6166.

Wilcock, G.K. M. M. Esiri, "Plaques, tangles and dementia. A quantitative study." J. Neurol. Sci. 56, 343-356 (1982).

U.S. Appl. No. 63/059,038, filed Jul. 30, 2020, George Richard Uhl.
U.S. Appl. No. 17/390,497, filed Jul. 30, 2021, George Richard Uhl.
U.S. Appl. No. 18/177,471, filed Mar. 2, 2023, George Richard Uhl.
U.S. Appl. No. 63/182,532, filed Apr. 30, 2021, George Richard Uhl.

* cited by examiner

PTPRD INHIBITORS AND USES THEREOF

CROSS-REFERENCE TO RELATED APPLICATIONS

This application claims priority to U.S. Provisional Application No. 63/182,532, filed Apr. 30, 2021, the entirety of which is incorporated into this application by reference.

STATEMENT REGARDING FEDERALLY SPONSORED RESEARCH

This invention was made with government support under grant number U01DA047713 awarded by the National Institutes of Health. The government has certain rights in the invention.

BACKGROUND

Substance abuse and nicotine dependence accounts for a high number of preventable illnesses and deaths each year and places significant social and financial tolls on society. Drug addiction is a dependence on an illegal drug or a legal, often prescribed medication. Individuals who are addicted to drugs or medications are often unable to control their drug use and often continue using the drug despite the harm it causes.

For many individuals, casual illegal drug use or temporary use of opioid pain medication for temporary acute pain, or in some cases, chronic pain, can lead to full-on addiction. Addiction can cause serious long-term health consequences, including problems with physical and mental health, relationships, employment, among other issues. When an individual repeatedly ingests or injects opioids or stimulants, for example, it is nearly impossible to suddenly stop taking the opioid or stimulant. As a result, the individual tends to focus on obtaining these substances as a way to function until dependency progresses to a point where the individual can no longer function in society. The difficulty with stopping use of many addictive substances such as opioids and stimulants relates to the reward effect produced when such substances are ingested or injected, as a result of the massive release of various rewarding chemicals in the brain such as dopamine, among others.

Addiction is a complex disorder characterized by compulsive drug use. While each drug produces different physical effects, all abused substances can alter the way the brain functions. Consuming or injecting a recreational or prescribed substance that is prone to cause addiction results in a surge in dopamine levels in the brain, which triggers feelings of reward. The brain recalls those feelings and creates a desire for the feeling to return again. In an individual that becomes addicted, the substance in question can take on the same significance as other survival behaviors, such as eating and drinking. Changes in the brain can interfere with the ability to think clearly, exercise good judgment, and control behavior.

An individual addicted to drugs may have the desire to quit, but most individuals find that they cannot do so without medical or therapeutic intervention. Depending on the level of addiction, the individual may need help withdrawing from using the drug, i.e., detoxification. Addiction and relapse, however, remain significant obstacles among those who seek help.

Nicotine dependence, primarily from tobacco use, presents its own unique problem. Tobacco use causes nearly 6 million deaths per year globally, with trends showing that tobacco use will cause more than 8 million deaths annually by 2030. In the United States alone, cigarette smoking is responsible for more than 480,000 deaths per year, including more than 41,000 deaths resulting from secondhand smoke. The economic cost of smoking for the United States is more than $300 billion each year, including nearly $170 billion in direct medical care for adults and more than $156 billion in lost productivity due to premature death and exposure to secondhand smoke.

The complex etiologies of substance-use disorders and nicotine dependence include features related to the rewarding properties of addictive substance. Rewarding properties of addictive substances play substantial roles in placement of such substances on Drug Enforcement Agency (DEA) schedules that mandate more or less constraints for prescribing in the United States. However, no anti-addiction therapeutic has yet been licensed based on its ability to reduce reward from illicit or prescribed substances that are prone to abuse. Accordingly, there is a need for therapeutic agents that display anti-addiction properties, e.g., that reduce the reward associated with the use of an addictive substance. This need and others are met by the following disclosure.

SUMMARY

The compounds described herein are potent inhibitors of receptor-type tyrosine-protein phosphatase delta (PTPRD). PTPRD is associated with several addiction-related phenotypes. Accordingly, by inhibiting PTPRD's ability to dephosphorylate certain substrates, including addiction-associated substrates, the compounds are useful for treating, preventing, or delaying the progression of addiction or dependence to a substance, including without limitation, nicotine, opioids, and stimulants. In some aspects, for example, the disclosed compounds can reduce the reward associated with certain substances that are prone to lead to dependency or addiction, and in doing so, treat, prevent, or delay the progression of a substance-use disorder or nicotine dependence. In other aspects, the compounds can be useful in treating obesity or metabolic syndrome.

In one aspect, this disclosure relates to compounds having a structure represented by Formula (I):

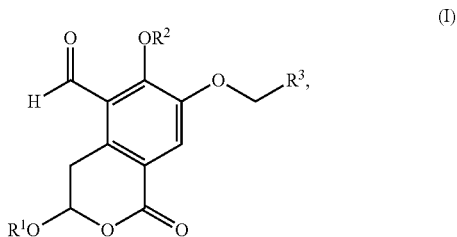

wherein $R^1$ is hydrogen, C1-C4 alkyl, C2-C4 alkenyl, C1-C4 haloalkyl, C1-C4 cyanoalkyl, C1-C4 hydroxyalkyl, C2-C4 alkoxy, C2-C4 haloalkoxy, C1-C4 alkylamino, C1-C4 acetyl, or (C1-C4)(C1-C4) dialkylamino;

$R^2$ is C1-C4 alkyl, C2-C4 alkenyl, C1-C4 haloalkyl, C1-C4 cyanoalkyl, C1-C4 hydroxyalkyl, C2-C4 alkoxy, C2-C4 haloalkoxy, C1-C4 alkylamino, or (C1-C4)(C1-C4) dialkylamino;

$R^3$ is hydrogen, C1-C9 alkyl, C2-C9 alkenyl, C2-C9 haloalkyl, C2-C9 cyanoalkyl, C2-C9 hydroxyalkyl, C2-C9 alkoxy, C2-C9 haloalkoxy, C2-C9 alkylamino, —(C1-C9 alkyl)NR$^4$R$^5$, C3-C8 cycloalkyl, C3-C8 cycloalkenyl, C3-C7 heterocyclyl, C3-C7 heterocycloalkenyl, C6-C10 aryl, C4-C9 heteroaryl, —(C1-C9 alkyl)(C3-C8 cycloalkyl), —(C1-C9 alkyl)(C3-C8 cycloalkenyl), —(C1-C9 alkyl)(C3-C7 heterocyclyl), —(C1-C9 alkyl)(C3-C7 heterocycloalkenyl), —(C1-C9 alkyl)(C6-C10 aryl), —(C1-C9 alkyl)(C4-C9 heteroaryl), —(C1-C9 alkyl)COR$^6$, —(C0-C9 alkyl)(C$_6$H$_4$)OR$^7$, or —(CO)R$^8$;

wherein R$^4$ and R$^5$, when present, are independently C1-C9 alkyl;

R$^6$, when present, is hydrogen, C1-C4 alkyl, C2-C4 alkenyl, C1-C4 haloalkyl, C1-C4 cyanoalkyl, C1-C4 hydroxyalkyl, C1-C4 alkoxy, C1-C4 haloalkoxy, C1-C4 alkylamino, C1-C4 aminoalkyl, or (C1-C4)(C1-C4) dialkylamino;

R$^7$, when present, is hydrogen, C1-C9 alkyl, C2-C9 alkenyl, C2-C9 haloalkyl, C2-C9 cyanoalkyl, C2-C9 hydroxyalkyl, C2-C9 haloalkoxy, C2-C9 alkoxy, C2-C9 alkylamino, C3-C8 cycloalkyl, C3-C8 cycloalkenyl, C3-C7 heterocyclyl, C3-C7 heterocycloalkenyl, C6-C10 aryl, or C4-C9 heteroaryl;

R$^8$, when present, is hydrogen, C1-C9 alkyl, C2-C9 alkenyl, C2-C9 haloalkyl, C2-C9 cyanoalkyl, C2-C9 hydroxyalkyl, C2-C9 haloalkoxy, C2-C9 alkoxy, C2-C9 alkylamino, C3-C8 cycloalkyl, C3-C8 cycloalkenyl, C3-C7 heterocyclyl, C3-C7 heterocycloalkenyl, C6-C10 aryl, or C4-C9 heteroaryl;

or a pharmaceutically-acceptable salt or prodrug thereof; provided that when R$^1$ is hydrogen and R$^2$ is methyl, R$^3$ is not isopropyl, propyl, butyl, pentyl, benzyl, or -methylcyclohexane.

Also disclosed is a method for treating, preventing, or delaying the progression of a disorder responsive to inhibition of receptor-type tyrosine-protein phosphatase delta (PT-PRD), the method comprising administering to a subject in need thereof an effective amount of a compound represented by Formula (I):

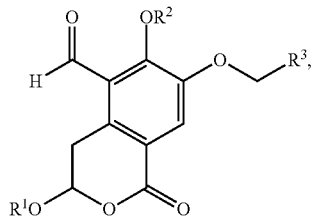

(I)

wherein R$^1$ is hydrogen, C1-C4 alkyl, C2-C4 alkenyl, C1-C4 haloalkyl, C1-C4 cyanoalkyl, C1-C4 hydroxyalkyl, C2-C4 alkoxy, C2-C4 haloalkoxy, C1-C4 alkylamino, C1-C4 acetyl, or (C1-C4)(C1-C4) dialkylamino;

R$^2$ is C1-C4 alkyl, C2-C4 alkenyl, C1-C4 haloalkyl, C1-C4 cyanoalkyl, C1-C4 hydroxyalkyl, C2-C4 alkoxy, C2-C4 haloalkoxy, C1-C4 alkylamino, or (C1-C4)(C1-C4) dialkylamino;

R$^3$ is hydrogen, C1-C9 alkyl, C2-C9 alkenyl, C2-C9 haloalkyl, C2-C9 cyanoalkyl, C2-C9 hydroxyalkyl, C2-C9 alkoxy, C2-C9 haloalkoxy, C2-C9 alkylamino, —(C1-C9 alkyl)NR$^4$R$^5$, C3-C8 cycloalkyl, C3-C8 cycloalkenyl, C3-C7 heterocyclyl, C3-C7 heterocycloalkenyl, C6-C10 aryl, C4-C9 heteroaryl, —(C1-C9 alkyl)(C3-C8 cycloalkyl), —(C1-C9 alkyl)(C3-C8 cycloalkenyl), —(C1-C9 alkyl)(C3-C7 heterocyclyl), —(C1-C9 alkyl)(C3-C7 heterocycloalkenyl), —(C1-C9 alkyl)(C6-C10 aryl), —(C1-C9 alkyl)(C4-C9 heteroaryl), —(C1-C9 alkyl)COR$^6$, —(C0-C9 alkyl)(C$_6$H$_4$)OR$^7$, or —(CO)R$^8$;

wherein R$^4$ and R$^5$, when present, are independently C1-C9 alkyl;

R$^6$, when present, is hydrogen, C1-C4 alkyl, C2-C4 alkenyl, C1-C4 haloalkyl, C1-C4 cyanoalkyl, C1-C4 hydroxyalkyl, C1-C4 alkoxy, C1-C4 haloalkoxy, C1-C4 alkylamino, C1-C4 aminoalkyl, or (C1-C4)(C1-C4) dialkylamino;

R$^7$, when present, is hydrogen, C1-C9 alkyl, C2-C9 alkenyl, C2-C9 haloalkyl, C2-C9 cyanoalkyl, C2-C9 hydroxyalkyl, C2-C9 haloalkoxy, C2-C9 alkoxy, C2-C9 alkylamino, C3-C8 cycloalkyl, C3-C8 cycloalkenyl, C3-C7 heterocyclyl, C3-C7 heterocycloalkenyl, C6-C10 aryl, or C4-C9 heteroaryl;

R$^8$, when present, is hydrogen, C1-C9 alkyl, C2-C9 alkenyl, C2-C9 haloalkyl, C2-C9 cyanoalkyl, C2-C9 hydroxyalkyl, C2-C9 haloalkoxy, C2-C9 alkoxy, C2-C9 alkylamino, C3-C8 cycloalkyl, C3-C8 cycloalkenyl, C3-C7 heterocyclyl, C3-C7 heterocycloalkenyl, C6-C10 aryl, or C4-C9 heteroaryl;

or a pharmaceutically-acceptable salt or prodrug thereof.

Also disclosed is a method for treating, preventing, or delaying the progression of a substance-use disorder, nicotine dependence, obesity, or metabolic syndrome, the method comprising administering to a subject in need thereof an effective amount of a compound represented by Formula (I):

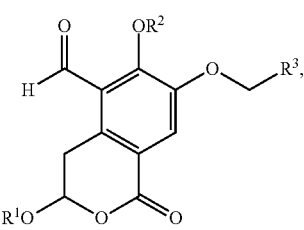

(I)

wherein R$^1$ is hydrogen, C1-C4 alkyl, C2-C4 alkenyl, C1-C4 haloalkyl, C1-C4 cyanoalkyl, C1-C4 hydroxyalkyl, C2-C4 alkoxy, C2-C4 haloalkoxy, C1-C4 alkylamino, C1-C4 acetyl, or (C1-C4)(C1-C4) dialkylamino;

R$^2$ is C1-C4 alkyl, C2-C4 alkenyl, C1-C4 haloalkyl, C1-C4 cyanoalkyl, C1-C4 hydroxyalkyl, C2-C4 alkoxy, C2-C4 haloalkoxy, C1-C4 alkylamino, or (C1-C4)(C1-C4) dialkylamino;

R$^3$ is hydrogen, C1-C9 alkyl, C2-C9 alkenyl, C2-C9 haloalkyl, C2-C9 cyanoalkyl, C2-C9 hydroxyalkyl, C2-C9 alkoxy, C2-C9 haloalkoxy, C2-C9 alkylamino, —(C1-C9 alkyl)NR$^4$R$^5$, C3-C8 cycloalkyl, C3-C8 cycloalkenyl, C3-C7 heterocyclyl, C3-C7 heterocycloalkenyl, C6-C10 aryl, C4-C9 heteroaryl, —(C1-C9 alkyl)(C3-C8 cycloalkyl), —(C1-C9 alkyl)(C3-C8 cycloalkenyl), —(C1-C9 alkyl)(C3-C7 heterocyclyl), —(C1-C9 alkyl)(C3-C7 heterocycloalkenyl), —(C1-C9 alkyl)(C6-C10 aryl), —(C1-C9 alkyl)(C4-C9 heteroaryl), —(C1-C9 alkyl)COR$^6$, —(C0-C9 alkyl)(C$_6$H$_4$)OR$^7$, or —(CO)R$^8$;

wherein R$^4$ and R$^5$, when present, are independently C1-C9 alkyl;

R⁶, when present, is hydrogen, C1-C4 alkyl, C2-C4 alkenyl, C1-C4 haloalkyl, C1-C4 cyanoalkyl, C1-C4 hydroxyalkyl, C1-C4 alkoxy, C1-C4 haloalkoxy, C1-C4 alkylamino, C1-C4 aminoalkyl, or (C1-C4)(C1-C4) dialkylamino;

R⁷, when present, is hydrogen, C1-C9 alkyl, C2-C9 alkenyl, C2-C9 haloalkyl, C2-C9 cyanoalkyl, C2-C9 hydroxyalkyl, C2-C9 haloalkoxy, C2-C9 alkoxy, C2-C9 alkylamino, C3-C8 cycloalkyl, C3-C8 cycloalkenyl, C3-C7 heterocyclyl, C3-C7 heterocycloalkenyl, C6-C10 aryl, or C4-C9 heteroaryl;

R⁸, when present, is hydrogen, C1-C9 alkyl, C2-C9 alkenyl, C2-C9 haloalkyl, C2-C9 cyanoalkyl, C2-C9 hydroxyalkyl, C2-C9 haloalkoxy, C2-C9 alkoxy, C2-C9 alkylamino, C3-C8 cycloalkyl, C3-C8 cycloalkenyl, C3-C7 heterocyclyl, C3-C7 heterocycloalkenyl, C6-C10 aryl, or C4-C9 heteroaryl;

or a pharmaceutically-acceptable salt or prodrug thereof.

Still other objects and advantages of the present disclosure will become readily apparent by those skilled in the art from the following detailed description, which is shown and described by reference to preferred aspects, simply by way of illustration of the best mode. As will be realized, the disclosure is capable of other and different aspects, and its several details are capable of modifications in various respects, without departing from the disclosure. Accordingly, the description is to be regarded as illustrative in nature and not as restrictive.

DETAILED DESCRIPTION

The present invention can be understood more readily by reference to the following detailed description of the invention and the Examples included therein.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present compositions, methods, and kits may be understood more readily by reference to the following detailed description of preferred embodiments and the examples included therein.

While aspects of this disclosure can be described and claimed in a particular statutory class, such as the system statutory class, this is for convenience only and one of skill in the art will understand that each aspect of this disclosure can be described and claimed in any statutory class. Unless otherwise expressly stated, it is in no way intended that any method or aspect set forth herein be construed as requiring that its steps be performed in a specific order. Accordingly, where a method claim does not specifically state in the claims or description that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present application is not entitled to antedate such publication by virtue of prior invention. Further, stated publication dates may be different from actual publication dates, which can require independent confirmation.

A. DEFINITIONS

Listed below are definitions of various terms used to describe this invention. These definitions apply to the terms as they are used throughout this specification, unless otherwise limited in specific instances, either individually or as part of a larger group.

As used in the specification and in the claims, the term "comprising" can include the aspects "consisting of" and "consisting essentially of."

As used in the specification and claims, the singular forms "a," "an," and "the" include plural referents unless the context clearly dictates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, "$IC_{50}$" is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein. In a further aspect, $IC_{50}$ refers to the half-maximal (50%) inhibitory concentration (IC) of a substance.

As used herein, "$EC_{50}$" is intended to refer to the concentration of a substance (e.g., a compound or a drug) that is required for 50% agonism of a biological process, or component of a process, including a protein, subunit, organelle, ribonucleoprotein, etc. In one aspect, an $EC_{50}$ can refer to the concentration of a substance that is required for 50% agonism in vivo, as further defined elsewhere herein. In a further aspect, $EC_{50}$ refers to the concentration of agonist that provokes a response halfway between the baseline and maximum response.

"Optional" or "optionally" means that the subsequently described event or circumstance may or may not occur, and that the description includes instances where said event or circumstance occurs and instances where it does not.

The term "pharmaceutically acceptable salt," as used herein, refers to an inorganic or organic salt of a disclosed compound that is suitable for administration to a subject.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption.

Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "by weight," when used in conjunction with a component, unless specially stated to the contrary is based on the total weight of the formulation or composition in which the component is included. For example, if a particular element or component in a composition or article is said to have 8% by weight, it is understood that this percentage is in relation to a total compositional percentage of 100%.

A weight percent of a component, or weight %, or wt %, unless specifically stated to the contrary, is based on the total weight of the formulation or composition in which the component is included.

As used herein, the term "subject" can be a vertebrate, such as a mammal, a fish, a bird, a reptile, or an amphibian. Thus, the subject can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with an ailment, disease, or disorder. The term "patient" includes human and veterinary subjects.

As used herein, the terms "treatment" and "treating" refer to the medical management of a subject with the intent to cure, ameliorate, stabilize, or prevent an ailment, disease, pathological condition, disorder, or injury. This term includes active treatment, that is, treatment directed specifically toward the improvement of a disease, pathological condition, disorder, or injury, and also includes causal treatment, that is, treatment directed toward removal of the cause of the associated disease, pathological condition, disorder, or injury. In addition, this term includes palliative treatment, that is, treatment designed for the relief of symptoms rather than the curing of the disease, pathological condition, disorder, or injury; preventative treatment, that is, treatment directed to minimizing or partially or completely inhibiting the development of the associated disease, pathological condition, disorder, or injury; and supportive treatment, that is, treatment employed to supplement another specific therapy directed toward the improvement of the associated disease, pathological condition, disorder, or injury. In various aspects, the term covers any treatment of a subject, including a mammal (e.g., a human), and includes: (i) preventing the disorder or condition from occurring in a subject that can be predisposed to the disorder or condition but has not yet been diagnosed as having it; (ii) inhibiting the disorder or condition, i.e., arresting its development or exacerbation thereof, or (iii) relieving the disorder or condition, i.e., promoting healing of the disorder or condition. In one aspect, the subject is a mammal such as a primate, and, in a further aspect, the subject is a human.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by a disclosed compound.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "dosage form" means a pharmacologically active material in a medium, carrier, vehicle, or device suitable for administration to a subject. A dosage forms can comprise inventive a disclosed compound, a product of a disclosed method of making, or a salt, solvate, or polymorph thereof, in combination with a pharmaceutically acceptable excipient, such as a preservative, buffer, saline, or phosphate buffered saline. Dosage forms can be made using conventional pharmaceutical manufacturing and compounding techniques. Dosage forms can comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol). A dosage form formulated for injectable use can have a disclosed compound, a product of a disclosed method of making, or a salt, solvate, or polymorph thereof, suspended in sterile saline solution for injection together with a preservative.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as a recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a non-aromatic carbon-based ring type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —NH₂, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl can be two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —NA$^1$A$^2$, where A$^1$ and A$^2$ can be, independently, hydrogen or alkyl, cycloalkyl, alkenyl, cycloalkenyl, alkynyl, cycloalkynyl, aryl, or heteroaryl group as described herein. A specific example of amino is —NH₂.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl)amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen," or "halide," as used herein can be used interchangeably and refer to F, Cl, Br, or I.

The terms "pseudohalide," "pseudohalogen," or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl," as used herein can be used interchangeably and refer to single and multi-cyclic aromatic or non-aromatic ring systems in which at least one of the ring members is other than carbon. Thus, the term is inclusive of, but not limited to, "heterocycloalkyl," "heteroaryl," "bicyclic heterocycle," and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group that has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula —$N_3$.

The term "nitro" as used herein is represented by the formula —$NO_2$.

The term "nitrile" or "cyano" as used herein is represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" is represented by the formula -$A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogen of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —$O(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}$Ph, which may be substituted with $R°$; —$(CH_2)_{0-4}O(CH_2)_{0-1}$Ph which may be substituted with $R°$; —CH=CHPh, which may be substituted with $R°$; —$(CH_2)_{0-4}O(CH_2)_{0-1}$-pyridyl which may be substituted with $R°$; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR$—, $SC(S)SR°$; —$(CH_2)_{0-4}SC(O)R°$; —$(CH_2)_{0-4}C(O)NR°_2$; —$C(S)NR°_2$; —$C(S)SR°$; —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°)_2$; $SiR°_3$; —$(C_{1-4}$ straight or branched alkylene)O—$N(R°)_2$; or —$(C_{1-4}$ straight or branched alkylene)C(O)O—$N(R°)_2$, wherein each $R°$ may be substituted as defined below and is independently hydrogen, $C_{1-6}$ aliphatic, —$CH_2$Ph, —$O(CH_2)_{0-1}$Ph, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R°$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R*, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet{}_2$, —NO$_2$, —SiR$^\bullet{}_3$, —OSiR$^\bullet{}_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet{}_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger{}_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger{}_2$, —C(S)NR$^\dagger{}_2$, —C(NH)NR$^\dagger{}_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet{}_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon-containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

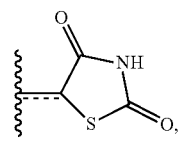

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included.

During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

When the disclosed compounds contain one chiral center, the compounds exist in two enantiomeric forms. Unless specifically stated to the contrary, a disclosed compound includes both enantiomers and mixtures of enantiomers, such as the specific 50:50 mixture referred to as a racemic mixture. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step can liberate the desired enantiomeric form. Alternatively, specific enantiomers can be synthesized by asymmetric synthesis using optically active reagents, substrates, catalysts or solvents, or by converting one enantiomer into the other by asymmetric transformation.

Designation of a specific absolute configuration at a chiral carbon in a disclosed compound is understood to mean that the designated enantiomeric form of the compounds can be provided in enantiomeric excess (e.e.). Enantiomeric excess, as used herein, is the presence of a particular enantiomer at greater than 50%, for example, greater than 60%, greater than 70%, greater than 75%, greater than 80%, greater than 85%, greater than 90%, greater than 95%, greater than 98%, or greater than 99%. In one aspect, the designated enantiomer is substantially free from the other enantiomer. For example, the "R" forms of the compounds can be substantially free from the "S" forms of the compounds and are, thus, in enantiomeric excess of the "S" forms. Conversely, "S" forms of the compounds can be substantially free of "R" forms of the compounds and are, thus, in enantiomeric excess of the "R" forms.

When a disclosed compound has two or more chiral carbons, it can have more than two optical isomers and can exist in diastereoisomeric forms. For example, when there are two chiral carbons, the compound can have up to four optical isomers and two pairs of enantiomers ((S,S)/(R,R) and (R,S)/(S,R)). The pairs of enantiomers (e.g., (S,S)/(R, R)) are mirror image stereoisomers of one another. The stereoisomers that are not mirror-images (e.g., (S,S) and (R,S) are diastereomers. The diastereoisomeric pairs can be separated by methods known to those skilled in the art, for example chromatography or crystallization and the individual enantiomers within each pair may be separated as described above. Unless otherwise specifically excluded, a disclosed compound includes each diastereoisomer of such compounds and mixtures thereof.

The compounds according to this disclosure may form prodrugs at hydroxyl or amino functionalities using alkoxy, amino acids, etc., groups as the prodrug forming moieties. For instance, the hydroxymethyl position may form mono-, di- or triphosphates and again these phosphates can form prodrugs. Preparations of such prodrug derivatives are discussed in various literature sources (examples are: Alexander et al., J. Med. Chem. 1988, 31, 318; Aligas-Martin et al., PCT WO 2000/041531, p. 30). The nitrogen function converted in preparing these derivatives is one (or more) of the nitrogen atoms of a compound of the disclosure.

"Derivatives" of the compounds disclosed herein are pharmaceutically acceptable salts, prodrugs, deuterated forms, radioactively labeled forms, isomers, solvates and combinations thereof. The "combinations" mentioned in this context are refer to derivatives falling within at least two of the groups: pharmaceutically acceptable salts, prodrugs, deuterated forms, radioactively labeled forms, isomers, and solvates. Examples of radioactively labeled forms include compounds labeled with tritium, phosphorous-32, iodine-129, carbon-11, fluorine-18, and the like.

Compounds described herein comprise atoms in both their natural isotopic abundance and in non-natural abundance. The disclosed compounds can be isotopically labeled or isotopically substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{35}$S, $^{18}$F and $^{36}$Cl, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules that owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

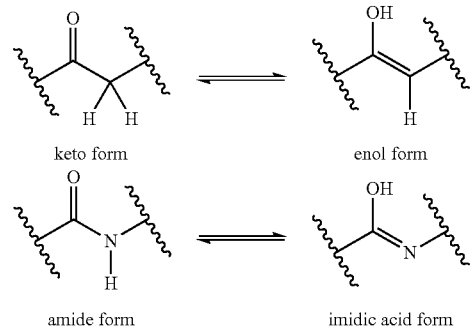

keto form          enol form amide form          imidic acid form

Likewise, amides with an N-hydrogen can exist in an equilibrium of the amide form and the imidic acid form. As another example, pyrazoles can exist in two tautomeric forms, $N^1$-unsubstituted, 3-$A^3$ and $N^1$-unsubstituted, 5-$A^3$ as shown below.

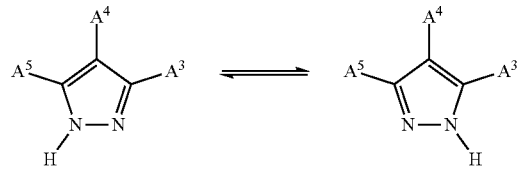

Unless stated to the contrary, the invention includes all such possible tautomers.

It is known that chemical substances form solids that are present in different states of order that are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

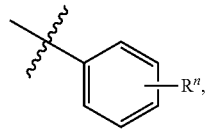

which is understood to be equivalent to a formula:

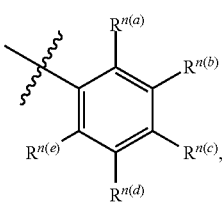

wherein n is typically an integer. That is, R" is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Strem Chemicals (Newburyport, MA), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

"PTPRD," as used herein, refers to a phosphatase enzyme known as receptor-type tyrosine-protein phosphatase delta, which is encoded by the PTPRD gene. The PTPRD enzyme contains an extracellular region, a single transmembrane segment, and two intracytoplasmic catalytic domains. The extracellular region of the enzyme comprises three Ig-like and eight fibronectin type III-like domains. The PTPRD enzyme is also known as HPTP, HPTPD, HPTPDELTA, PTPD, RPTDELTA, protein tyrosine phosphatase, receptor type D, protein tyrosine phosphatase receptor type D, and R-PTP-delta.

"Metabolic syndrome" refers to a cluster of conditions that increase the risk of heart disease, stroke, and diabetes. These conditions include one or more of high blood pressure, high blood sugar, excess body fat around the waist, and abnormal cholesterol levels.

"Obesity" refers to a disorder involving excessive body fat that increase the risk of health problems, typically occurring when a subject's body mass index is 30 or greater.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

B. COMPOUNDS

In one aspect, the disclosed compounds act as potent PTPRD inhibitors. The receptor type protein tyrosine phosphatase PTPRD binds to extracellular ligands in ways that alter activities of its intracellular protein tyrosine phosphatase. PTPRD is one of the most highly-expressed, largely-neuronal receptor-type protein tyrosine phosphatases, as documented in human and mouse RNAseq, in situ hybridization and immunohistochemical studies. Candidate PTPRD substrates that were nominated by PTPRD knockout phosphoproteomics and confirmed by in vitro studies include β actin, dock4, cofilin, as well as a phosphotyrosine sequence shared by GSK3a and GSK30.

As demonstrated by this disclosure, human genetic and mouse model studies support contributions of variation in PTPRD signaling to addiction-related phenotypes that include vulnerability to develop a substance-use disorder, reward from stimulants and opioids, and ability to quit use of opioids or nicotine use. For example, there is decreased cocaine reward in mice with decreased levels of PTPRD expression, meaning that small molecule inhibitors of the activity of PTPRD's phosphatase can reduce human reward from stimulants and other substances that are prone to abuse or dependance.

The disclosed compounds are based in part on in vitro and in vivo studies of PTPRD phosphatase inhibitors as anti-addiction therapeutics. PTPRD has no reported in vitro small molecule structure-activity relationship (SAR) data. To improve understanding of PTPRD/1 interactions and to identify routes to development of improved PTPRD phosphatase inhibitors as potential anti-addiction therapeutics, the inventors synthesized and conducted in vitro tests of activities of a series of PTPRD inhibitors, using a design-make-test-analyze cycle. In vitro activities were tested using recombinant PTPRD and related tyrosine phosphatases, pNPP hydrolysis, and pYGSK3 orthophosphate release assays. Certain disclosed compounds were docked to PTPRD's phosphatase in silico. The results surprisingly demonstrate that the disclosed compounds have potent effects on PTPRD inhibition, and in turn, are useful in treating, preventing, or delaying the progression of addiction, a substance-use disorder, a nicotine dependence, or another disorder responsive to PTPRD inhibition.

1. Structure

In one aspect, the compounds have a structure represented by Formula (I):

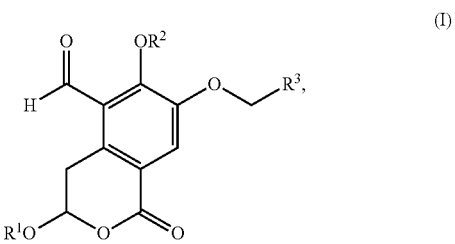

(I)

wherein $R^1$ is hydrogen, C1-C4 alkyl, C2-C4 alkenyl, C1-C4 haloalkyl, C1-C4 cyanoalkyl, C1-C4 hydroxyalkyl, C2-C4 alkoxy, C2-C4 haloalkoxy, C1-C4 alkylamino, C1-C4 acetyl, or (C1-C4)(C1-C4) dialkylamino;

$R^2$ is C1-C4 alkyl, C2-C4 alkenyl, C1-C4 haloalkyl, C1-C4 cyanoalkyl, C1-C4 hydroxyalkyl, C2-C4 alkoxy, C2-C4 haloalkoxy, C1-C4 alkylamino, or (C1-C4)(C1-C4) dialkylamino;

$R^3$ is hydrogen, C1-C9 alkyl, C2-C9 alkenyl, C2-C9 haloalkyl, C2-C9 cyanoalkyl, C2-C9 hydroxyalkyl, C2-C9 alkoxy, C2-C9 haloalkoxy, C2-C9 alkylamino, —(C1-C9 alkyl)$NR^4R^5$, C3-C8 cycloalkyl, C3-C8 cycloalkenyl, C3-C7 heterocyclyl, C3-C7 heterocloalkenyl, C6-C10 aryl, C4-C9 heteroaryl, —(C1-C9 alkyl)(C3-C8 cycloalkyl), —(C1-C9 alkyl)(C3-C8 cycloalkenyl), —(C1-C9 alkyl)(C3-C7 heterocyclyl), —(C1-C9 alkyl)(C3-C7 heterocycloalkenyl), —(C1-C9 alkyl)(C6-C10 aryl), —(C1-C9 alkyl)(C4-C9 heteroaryl), —(C1-C9 alkyl)COR$^6$, —(C0-C9 alkyl)(C$_6$H$_4$)OR$^7$, or —(CO)R$^8$;

wherein R$^4$ and R$^5$, when present, are independently C1-C9 alkyl;

R$^6$, when present, is hydrogen, C1-C4 alkyl, C2-C4 alkenyl, C1-C4 haloalkyl, C1-C4 cyanoalkyl, C1-C4 hydroxyalkyl, C1-C4 alkoxy, C1-C4 haloalkoxy, C1-C4 alkylamino, C1-C4 aminoalkyl, or (C1-C4)(C1-C4) dialkylamino;

R$^7$, when present, is hydrogen, C1-C9 alkyl, C2-C9 alkenyl, C2-C9 haloalkyl, C2-C9 cyanoalkyl, C2-C9 hydroxyalkyl, C2-C9 haloalkoxy, C2-C9 alkoxy, C2-C9 alkylamino, C3-C8 cycloalkyl, C3-C8 cycloalkenyl, C3-C7 heterocyclyl, C3-C7 heterocycloalkenyl, C6-C10 aryl, or C4-C9 heteroaryl;

R$^8$, when present, is hydrogen, C1-C9 alkyl, C2-C9 alkenyl, C2-C9 haloalkyl, C2-C9 cyanoalkyl, C2-C9 hydroxyalkyl, C2-C9 haloalkoxy, C2-C9 alkoxy, C2-C9 alkylamino, C3-C8 cycloalkyl, C3-C8 cycloalkenyl, C3-C7 heterocyclyl, C3-C7 heterocycloalkenyl, C6-C10 aryl, or C4-C9 heteroaryl;

or a pharmaceutically-acceptable salt or prodrug thereof; provided that when R$^1$ is hydrogen and R$^2$ is methyl, R$^3$ is not isopropyl, propyl, butyl, pentyl, benzyl, or -methylcyclohexane.

In a further aspect, R$^1$ is hydrogen or C1-C2 alkyl; R$^2$ is C1-C2 alkyl; and R$^3$ is hydrogen, C1-C4 alkyl, C2-C4 alkenyl, C2-C4 haloalkyl, C2-C4 alkoxy, —(C1-C4 alkyl)NR$^4$R$^5$, —(C1-C4 alkyl)COR$^6$, C3-C8 cycloalkyl, C3-C7 heterocyclyl, C6-C10 aryl, C4-C9 heteroaryl, —(C1-C4 alkyl)(C6-C10 aryl), —(C1-C4 alkyl)(C4-C9 heteroaryl), —(CO—C4 alkyl)(C$_6$H$_4$)OR$^7$, or —(CO)R$^8$; wherein R$^4$ and R$^5$, when present, are independently C1-C4 alkyl; R$^6$, when present, is hydrogen or C1-C4 alkyl; R$^7$, when present, is hydrogen or C1-C4 alkyl; and R$^8$, when present, is hydrogen, C1-C4 alkyl, C2-C4 alkenyl, C2-C4 haloalkyl, C2-C4 cyanoalkyl, C2-C4 hydroxyalkyl, C2-C4 haloalkoxy, C2-C4 alkoxy, C2-C9 alkylamino, C3-C8 cycloalkyl, C3-C8 cycloalkenyl, C3-C7 heterocyclyl, C3-C7 heterocycloalkenyl, C6-C10 aryl, or C4-C9 heteroaryl.

In a still further aspect, the compounds have a structure represented by Formula (II):

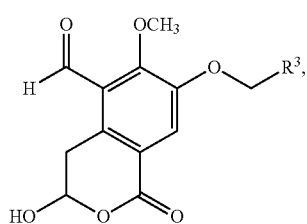

(II)

wherein R$^3$ is hydrogen, C1-C4 alkyl, C2-C4 alkenyl, C2-C4 haloalkyl, C2-C4 alkoxy, —(C1-C4 alkyl)NR$^4$R$^5$, C3-C8 cycloalkyl, C3-C7 heterocyclyl, C6-C10 aryl, C4-C9 heteroaryl, —(C1-C4 alkyl)(C6-C10 aryl), —(C1-C4 alkyl)(C4-C9 heteroaryl), —(CO—C4 alkyl)(C$_6$H$_4$)OR$^7$, or —(CO)R$^8$; wherein R$^4$ and R$^5$, when present, are independently C1-C4 alkyl; R$^7$, when present, is hydrogen or C1-C4 alkyl; and R$^8$, when present, is hydrogen, C1-C4 alkyl, C2-C4 haloalkyl, C2-C4 hydroxyalkyl, C2-C4 haloalkoxy, C2-C4 alkoxy, C3-C8 cycloalkyl, C3-C7 heterocyclyl, C3-C7 heterocycloalkenyl, C6-C10 aryl, or C4-C9 heteroaryl.

a. R$^1$ Groups

In one aspect, R$^1$ can be hydrogen, C1-C4 alkyl, C2-C4 alkenyl, C1-C4 haloalkyl, C1-C4 cyanoalkyl, C1-C4 hydroxyalkyl, C2-C4 alkoxy, C2-C4 haloalkoxy, C1-C4 alkylamino, C1-C4 acetyl, or (C1-C4)(C1-C4) dialkylamino. Non-limiting examples of suitable R$^1$ groups include hydrogen, methyl, ethyl, n-propyl, isopropyl, ethenyl, n-propenyl, isopropenyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —CH$_2$OCH$_3$, —CH$_2$CH$_2$OCH$_3$, —CH$_2$CH$_2$OCH$_2$CH$_3$, —CH$_2$OCH$_2$Cl, —CH$_2$CH$_2$OCH$_2$Br, —CH$_2$CH$_2$OCH$_2$CH$_2$F, —CH$_2$NH$_2$, —CH$_2$CH$_2$NH$_2$, —CH$_2$CH$_2$CH$_2$NH$_2$, —CH(CH$_3$)CH$_2$NH$_2$, and —CH$_2$N(CH$_3$)$_2$.

In a further aspect, R$^1$ is hydrogen or C1-C2 alkyl, e.g., methyl or ethyl. In a still further aspect, R$^1$ is hydrogen.

b. R$^2$ Groups

In one aspect, R$^2$ is C1-C4 alkyl, C2-C4 alkenyl, C1-C4 haloalkyl, C1-C4 cyanoalkyl, C1-C4 hydroxyalkyl, C2-C4 alkoxy, C2-C4 haloalkoxy, C1-C4 alkylamino, or (C1-C4)(C1-C4) dialkylamino. Non-limiting examples of suitable R$^2$ groups include methyl, ethyl, n-propyl, isopropyl, ethenyl, n-propenyl, isopropenyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —CH$_2$OCH$_3$, —CH$_2$CH$_2$OCH$_3$, —CH$_2$CH$_2$OCH$_2$CH$_3$, —CH$_2$OCH$_2$Cl, —CH$_2$CH$_2$OCH$_2$Br, —CH$_2$CH$_2$OCH$_2$CH$_2$F, —CH$_2$NH$_2$, —CH$_2$CH$_2$NH$_2$, —CH$_2$CH$_2$CH$_2$NH$_2$, —CH(CH$_3$)CH$_2$NH$_2$, and —CH$_2$N(CH$_3$)$_2$.

In a further aspect, R$^2$ is C1-C2 alkyl, e.g., methyl or ethyl. In a still further aspect, R$^2$ is methyl.

c. R$^3$ Groups

In one aspect, R$^3$ can be hydrogen, C1-C9 alkyl, C2-C9 alkenyl, C2-C9 haloalkyl, C2-C9 cyanoalkyl, C2-C9 hydroxyalkyl, C2-C9 alkoxy, C2-C9 haloalkoxy, C2-C9 alkylamino, —(C1-C9 alkyl)NR$^4$R$^5$, C3-C8 cycloalkyl, C3-C8 cycloalkenyl, C3-C7 heterocyclyl, C3-C7 heterocycloalkenyl, C6-C10 aryl, C4-C9 heteroaryl, —(C1-C9 alkyl)(C3-C8 cycloalkyl), —(C1-C9 alkyl)(C3-C8 cycloalkenyl), —(C1-C9 alkyl)(C3-C7 heterocyclyl), —(C1-C9 alkyl)(C3-C7 heterocycloalkenyl), —(C1-C9 alkyl)(C6-C10 aryl), —(C1-C9 alkyl)(C4-C9 heteroaryl), —(C1-C9 alkyl)COR$^6$, —(C0-C9 alkyl)(C$_6$H$_4$)OR$^7$, or —(CO)R$^8$.

In one aspect, R$^4$ and R$^5$, when present, are independently C1-C9 alkyl. Non-limiting examples of suitable R$^4$ and R$^5$ groups include methyl, ethyl, n-propyl, isopropyl, ethenyl, n-propenyl, isopropenyl, pentyl, isopentyl, hexyl, heptyl, octyl, nonyl, 3-methylpentyl, 2,3-dimethylpentyl, 3-ethyl-2-methylpentyl, 3-ethyl-4-methylhexyl, 4-ethyl-3-methylheptyl, 4-ethyl-5-methyloctyl, or 5-ethyl-4-methylnonyl.

In one aspect, R$^6$, when present, is hydrogen, C1-C4 alkyl, C2-C4 alkenyl, C1-C4 haloalkyl, C1-C4 cyanoalkyl, C1-C4 hydroxyalkyl, C1-C4 alkoxy, C1-C4 haloalkoxy, C1-C4 alkylamino, C1-C4 aminoalkyl, or (C1-C4)(C1-C4) dialkylamino. Non-limiting examples of suitable R$^6$ groups include methyl, ethyl, n-propyl, isopropyl, ethenyl, n-propenyl, isopropenyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —CH$_2$OCH$_3$, —CH$_2$CH$_2$OCH$_3$, —CH$_2$CH$_2$OCH$_2$CH$_3$, —CH$_2$OCH$_2$Cl, —CH$_2$CH$_2$OCH$_2$Br, —CH$_2$CH$_2$OCH$_2$CH$_2$F, —CH$_2$NH$_2$, —CH$_2$CH$_2$NH$_2$, —CH$_2$CH$_2$CH$_2$NH$_2$, —CH(CH$_3$)CH$_2$NH$_2$, and —CH$_2$N(CH$_3$)$_2$.

In one aspect, R$^7$, when present, is hydrogen, C1-C9 alkyl, C2-C9 alkenyl, C2-C9 haloalkyl, C2-C9 cyanoalkyl, C2-C9 hydroxyalkyl, C2-C9 haloalkoxy, C2-C9 alkoxy, C2-C9 alkylamino, C3-C8 cycloalkyl, C3-C8 cycloalkenyl, C3-C7 heterocyclyl, C3-C7 heterocycloalkenyl, C6-C10 aryl, or C4-C9 heteroaryl. Non-limiting examples of suitable R$^7$ groups include methyl, ethyl, n-propyl, isopropyl, ethenyl, n-propenyl, isopropenyl, pentyl, isopentyl, hexyl, heptyl, octyl, nonyl, 3-methylpentyl, 2,3-dimethylpentyl, 3-ethyl-2-methylpentyl, 3-ethyl-4-methylhexyl, 4-ethyl-3-methylheptyl, 4-ethyl-5-methyloctyl, or 5-ethyl-4-methylnonyl. Other suitable examples include —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —CH$_2$OCH$_3$, —CH$_2$CH$_2$OCH$_3$, —CH$_2$CH$_2$OCH$_2$CH$_3$, —CH$_2$OCH$_2$Cl, —CH$_2$CH$_2$OCH$_2$Br, —CH$_2$CH$_2$OCH$_2$CH$_2$F, —CH$_2$NH$_2$, —CH$_2$CH$_2$NH$_2$, —CH$_2$CH$_2$CH$_2$NH$_2$, —CH(CH$_3$)CH$_2$NH$_2$, and —CH$_2$N(CH$_3$)$_2$. Still further examples include cyclopropyl, cyclopentyl, and cyclohexyl. Other examples include benzyl, pyridyl, and the like.

In one aspect, R$^8$, when present, is hydrogen, C1-C9 alkyl, C2-C9 alkenyl, C2-C9 haloalkyl, C2-C9 cyanoalkyl, C2-C9 hydroxyalkyl, C2-C9 haloalkoxy, C2-C9 alkoxy, C2-C9 alkylamino, C3-C8 cycloalkyl, C3-C8 cycloalkenyl, C3-C7 heterocyclyl, C3-C7 heterocycloalkenyl, C6-C10 aryl, or C4-C9 heteroaryl. Non-limiting examples of suitable R$^8$ groups include methyl, ethyl, n-propyl, isopropyl, ethenyl, n-propenyl, isopropenyl, pentyl, isopentyl, hexyl, heptyl, octyl, nonyl, 3-methylpentyl, 2,3-dimethylpentyl, 3-ethyl-2-methylpentyl, 3-ethyl-4-methylhexyl, 4-ethyl-3-methylheptyl, 4-ethyl-5-methyloctyl, or 5-ethyl-4-methylnonyl. Other suitable examples include —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —CH$_2$OCH$_3$, —CH$_2$CH$_2$OCH$_3$, —CH$_2$CH$_2$OCH$_2$CH$_3$, —CH$_2$OCH$_2$Cl, —CH$_2$CH$_2$OCH$_2$Br, —CH$_2$CH$_2$OCH$_2$CH$_2$F, —CH$_2$NH$_2$, —CH$_2$CH$_2$NH$_2$, —CH$_2$CH$_2$CH$_2$NH$_2$, —CH(CH$_3$)CH$_2$NH$_2$, and —CH$_2$N(CH$_3$)$_2$. Still further examples include cyclopropyl, cyclopentyl, and cyclohexyl. Other examples include benzyl, pyridyl, and the like.

In a further aspect, R$^3$ is hydrogen or has a structure represented by the formula:

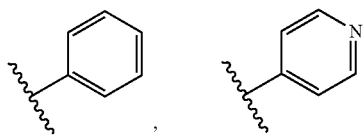

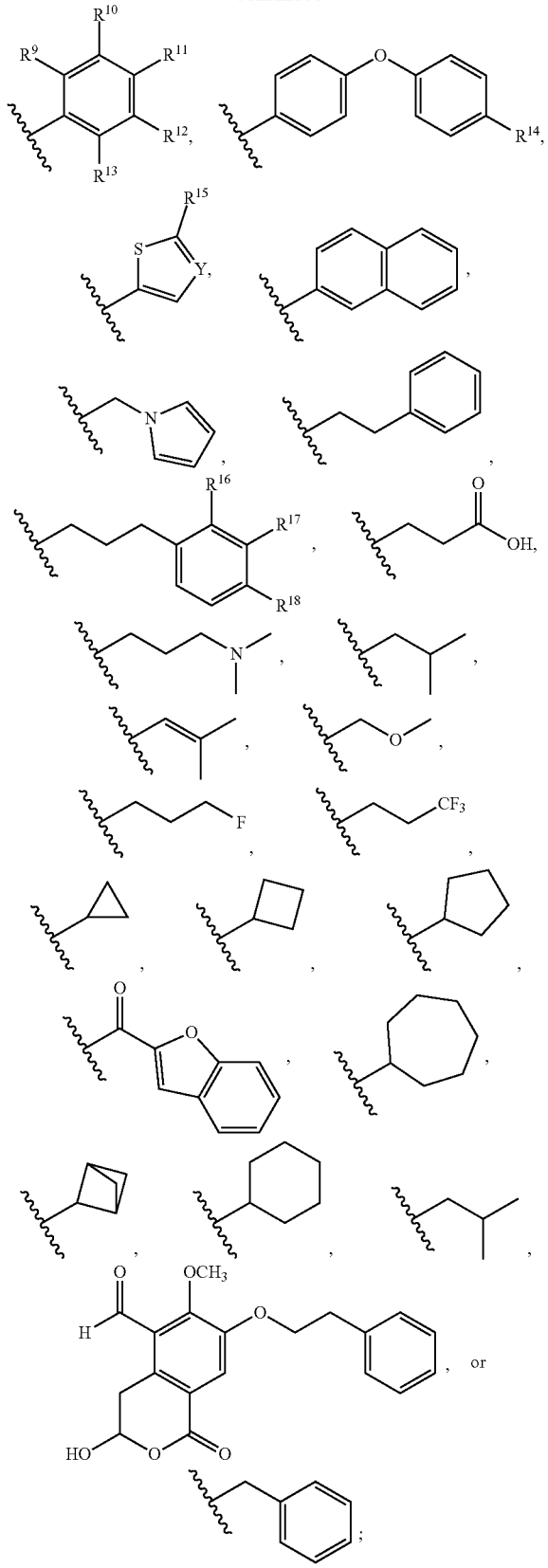

wherein R$^9$-R$^{13}$, when present, are independently hydrogen, methyl, —OCH$_3$, —CN, —CF$_3$, —OCF$_3$, or halide; R$^{14}$, when present, is hydrogen or halide; $R^{15}$, when present, is methyl or halide; Y, when present, is CH or N; and $R^{16-18}$, when present, are independently hydrogen, hydroxyl, or halide.

In a further aspect, $R^3$ has a structure represented by the formula:

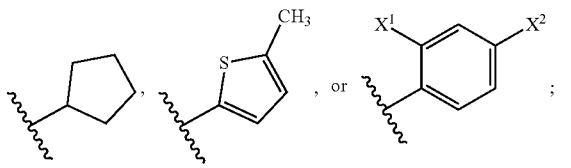

wherein $X^1$ and $X^2$, when present, is independently —Cl, —Br, —I, or —F.

2. Prodrugs

Also disclosed are prodrugs of the compounds. Suitable prodrugs include without limitation compounds in which the aldehyde group on the compounds is converted to an oxime, bisulfate, amine, or other suitable, reversibly-reacting functional group.

According to one aspect, the prodrug can be an oxime compound corresponding to the structure represented by Formula (III):

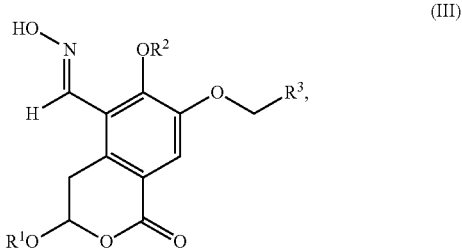

wherein $R^1$ is hydrogen, C1-C4 alkyl, C2-C4 alkenyl, C1-C4 haloalkyl, C1-C4 cyanoalkyl, C1-C4 hydroxyalkyl, C2-C4 alkoxy, C2-C4 haloalkoxy, C1-C4 alkylamino, C1-C4 acetyl, or (C1-C4)(C1-C4) dialkylamino;

$R^2$ is C1-C4 alkyl, C2-C4 alkenyl, C1-C4 haloalkyl, C1-C4 cyanoalkyl, C1-C4 hydroxyalkyl, C2-C4 alkoxy, C2-C4 haloalkoxy, C1-C4 alkylamino, or (C1-C4)(C1-C4) dialkylamino;

$R^3$ is hydrogen, C1-C9 alkyl, C2-C9 alkenyl, C2-C9 haloalkyl, C2-C9 cyanoalkyl, C2-C9 hydroxyalkyl, C2-C9 alkoxy, C2-C9 haloalkoxy, C2-C9 alkylamino, —(C1-C9 alkyl)NR$^4$R$^5$, C3-C8 cycloalkyl, C3-C8 cycloalkenyl, C3-C7 heterocyclyl, C3-C7 heterocycloalkenyl, C6-C10 aryl, C4-C9 heteroaryl, —(C1-C9 alkyl)(C3-C8 cycloalkyl), —(C1-C9 alkyl)(C3-C8 cycloalkenyl), —(C1-C9 alkyl)(C3-C7 heterocyclyl), —(C1-C9 alkyl)(C3-C7 heterocycloalkenyl), —(C1-C9 alkyl)(C6-C10 aryl), —(C1-C9 alkyl)(C4-C9 heteroaryl), —(C1-C9 alkyl)COR$^6$, —(C0-C9 alkyl)(C$_6$H$_4$)OR$^7$, or —(CO)R$^8$;

wherein $R^4$ and $R^5$, when present, are independently C1-C9 alkyl;

$R^6$, when present, is hydrogen, C1-C4 alkyl, C2-C4 alkenyl, C1-C4 haloalkyl, C1-C4 cyanoalkyl, C1-C4 hydroxyalkyl, C1-C4 alkoxy, C1-C4 haloalkoxy, C1-C4 alkylamino, C1-C4 aminoalkyl, or (C1-C4)(C1-C4) dialkylamino;

$R^7$, when present, is hydrogen, C1-C9 alkyl, C2-C9 alkenyl, C2-C9 haloalkyl, C2-C9 cyanoalkyl, C2-C9 hydroxyalkyl, C2-C9 haloalkoxy, C2-C9 alkoxy, C2-C9 alkylamino, C3-C8 cycloalkyl, C3-C8 cycloalkenyl, C3-C7 heterocyclyl, C3-C7 heterocycloalkenyl, C6-C10 aryl, or C4-C9 heteroaryl;

$R^8$, when present, is hydrogen, C1-C9 alkyl, C2-C9 alkenyl, C2-C9 haloalkyl, C2-C9 cyanoalkyl, C2-C9 hydroxyalkyl, C2-C9 haloalkoxy, C2-C9 alkoxy, C2-C9 alkylamino, C3-C8 cycloalkyl, C3-C8 cycloalkenyl, C3-C7 heterocyclyl, C3-C7 heterocycloalkenyl, C6-C10 aryl, or C4-C9 heteroaryl;

or a pharmaceutically-acceptable salt thereof.

In some aspects of the prodrugs of Formula (III), when $R^1$ is hydrogen and $R^2$ is methyl, $R^3$ is not isopropyl, propyl, butyl, pentyl, benzyl, or -methylcyclohexane.

In a still further aspect, the prodrugs have a structure represented by Formula (II):

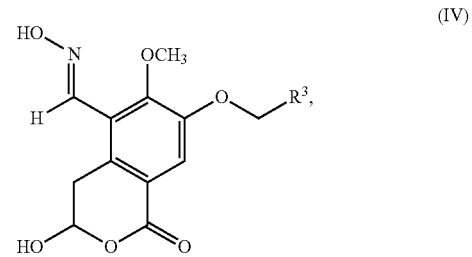

wherein $R^3$ is hydrogen, C1-C4 alkyl, C2-C4 alkenyl, C2-C4 haloalkyl, C2-C4 alkoxy, —(C1-C4 alkyl)NR$^4$R$^5$, C3-C8 cycloalkyl, C3-C7 heterocyclyl, C6-C10 aryl, C4-C9 heteroaryl, —(C1-C4 alkyl)(C6-C10 aryl), —(C1-C4 alkyl)(C4-C9 heteroaryl), —(CO—C4 alkyl)(C$_6$H$_4$)OR$^7$, or —(CO)R$^8$; wherein $R^4$ and $R^5$, when present, are independently C1-C4 alkyl; $R^7$, when present, is hydrogen or C1-C4 alkyl; and $R^8$, when present, is hydrogen, C1-C4 alkyl, C2-C4 haloalkyl, C2-C4 hydroxyalkyl, C2-C4 haloalkoxy, C2-C4 alkoxy, C3-C8 cycloalkyl, C3-C7 heterocyclyl, C3-C7 heterocycloalkenyl, C6-C10 aryl, or C4-C9 heteroaryl.

The oxime (aldoxime) prodrugs can be any of the compounds described above, in which the aldehyde group has been converted to an aldoxime. Methods for converting aldehydes to aldoximes are known in the art.

In a further aspect, the prodrug can be a bisulfate adduct of the disclosed compounds, in which the aldehyde group has been converted to a bisulfate group. Thus, the prodrug can be a bisulfate compound having a structure represented by Formula (V):

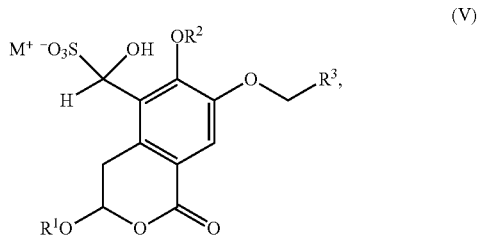

wherein $R^1$ is hydrogen, C1-C4 alkyl, C2-C4 alkenyl, C1-C4 haloalkyl, C1-C4 cyanoalkyl, C1-C4 hydroxyalkyl, C2-C4 alkoxy, C2-C4 haloalkoxy, C1-C4 alkylamino, C1-C4 acetyl, or (C1-C4)(C1-C4) dialkylamino;

R² is C1-C4 alkyl, C2-C4 alkenyl, C1-C4 haloalkyl, C1-C4 cyanoalkyl, C1-C4 hydroxyalkyl, C2-C4 alkoxy, C2-C4 haloalkoxy, C1-C4 alkylamino, or (C1-C4)(C1-C4) dialkylamino;

R³ is hydrogen, C1-C9 alkyl, C2-C9 alkenyl, C2-C9 haloalkyl, C2-C9 cyanoalkyl, C2-C9 hydroxyalkyl, C2-C9 alkoxy, C2-C9 haloalkoxy, C2-C9 alkylamino, —(C1-C9 alkyl)NR⁴R⁵, C3-C8 cycloalkyl, C3-C8 cycloalkenyl, C3-C7 heterocyclyl, C3-C7 heterocycloalkenyl, C6-C10 aryl, C4-C9 heteroaryl, —(C1-C9 alkyl)(C3-C8 cycloalkyl), —(C1-C9 alkyl)(C3-C8 cycloalkenyl), —(C1-C9 alkyl)(C3-C7 heterocyclyl), —(C1-C9 alkyl)(C3-C7 heterocycloalkenyl), —(C1-C9 alkyl)(C6-C10 aryl), —(C1-C9 alkyl)(C4-C9 heteroaryl), —(C1-C9 alkyl)COR⁶, —(C0-C9 alkyl)(C₆H₄)OR⁷, or —(CO)R⁸;

wherein R⁴ and R⁵, when present, are independently C1-C9 alkyl;

R⁶, when present, is hydrogen, C1-C4 alkyl, C2-C4 alkenyl, C1-C4 haloalkyl, C1-C4 cyanoalkyl, C1-C4 hydroxyalkyl, C1-C4 alkoxy, C1-C4 haloalkoxy, C1-C4 alkylamino, C1-C4 aminoalkyl, or (C1-C4)(C1-C4) dialkylamino;

R⁷, when present, is C1-C9 alkyl, C2-C9 alkenyl, C2-C9 haloalkyl, C2-C9 cyanoalkyl, C2-C9 hydroxyalkyl, C2-C9 haloalkoxy, C2-C9 alkoxy, C2-C9 alkylamino, C3-C8 cycloalkyl, C3-C8 cycloalkenyl, C3-C7 heterocyclyl, C3-C7 heterocycloalkenyl, C6-C10 aryl, or C4-C9 heteroaryl;

R⁸, when present, is hydrogen, C1-C9 alkyl, C2-C9 alkenyl, C2-C9 haloalkyl, C2-C9 cyanoalkyl, C2-C9 hydroxyalkyl, C2-C9 haloalkoxy, C2-C9 alkoxy, C2-C9 alkylamino, C3-C8 cycloalkyl, C3-C8 cycloalkenyl, C3-C7 heterocyclyl, C3-C7 heterocycloalkenyl, C6-C10 aryl, or C4-C9 heteroaryl;

or a pharmaceutically-acceptable salt thereof; wherein M⁺ corresponds to a cation such as sodium and the like.

In some aspects of the prodrugs of Formula (V), when R¹ is hydrogen and R² is methyl, R³ is not isopropyl, propyl, butyl, pentyl, benzyl, or -methylcyclohexane.

In a further aspect, the bisulfate prodrugs have a structure represented by Formula (VI):

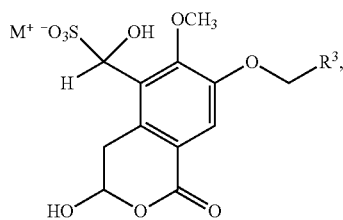

(VI)

wherein R³ is hydrogen, C1-C4 alkyl, C2-C4 alkenyl, C2-C4 haloalkyl, C2-C4 alkoxy, —(C1-C4 alkyl)NR⁴R⁵, C3-C8 cycloalkyl, C3-C7 heterocyclyl, C6-C10 aryl, C4-C9 heteroaryl, —(C1-C4 alkyl)(C6-C10 aryl), —(C1-C4 alkyl)(C4-C9 heteroaryl), —(CO—C4 alkyl)(C₆H₄)OR⁷, or —(CO)R⁸; wherein R⁴ and R⁵, when present, are independently C1-C4 alkyl; R⁷, when present, is hydrogen or C1-C4 alkyl; and R⁸, when present, is hydrogen, C1-C4 alkyl, C2-C4 haloalkyl, C2-C4 hydroxyalkyl, C2-C4 haloalkoxy, C2-C4 alkoxy, C3-C8 cycloalkyl, C3-C7 heterocyclyl, C3-C7 heterocycloalkenyl, C6-C10 aryl, or C4-C9 heteroaryl; wherein M⁺ corresponds to a cation such as sodium and the like.

In another aspect, the prodrugs can be compounds in which the aldehyde group has been converted to an amine. Thus, the amine prodrugs can have a structure represented by Formula (VII):

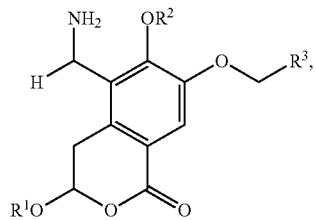

(VII)

wherein R¹ is hydrogen, C1-C4 alkyl, C2-C4 alkenyl, C1-C4 haloalkyl, C1-C4 cyanoalkyl, C1-C4 hydroxyalkyl, C2-C4 alkoxy, C2-C4 haloalkoxy, C1-C4 alkylamino, C1-C4 acetyl, or (C1-C4)(C1-C4) dialkylamino;

R² is C1-C4 alkyl, C2-C4 alkenyl, C1-C4 haloalkyl, C1-C4 cyanoalkyl, C1-C4 hydroxyalkyl, C2-C4 alkoxy, C2-C4 haloalkoxy, C1-C4 alkylamino, or (C1-C4)(C1-C4) dialkylamino;

R³ is hydrogen, C1-C9 alkyl, C2-C9 alkenyl, C2-C9 haloalkyl, C2-C9 cyanoalkyl, C2-C9 hydroxyalkyl, C2-C9 alkoxy, C2-C9 haloalkoxy, C2-C9 alkylamino, —(C1-C9 alkyl)NR⁴R⁵, C3-C8 cycloalkyl, C3-C8 cycloalkenyl, C3-C7 heterocyclyl, C3-C7 heterocycloalkenyl, C6-C10 aryl, C4-C9 heteroaryl, —(C1-C9 alkyl)(C3-C8 cycloalkyl), —(C1-C9 alkyl)(C3-C8 cycloalkenyl), —(C1-C9 alkyl)(C3-C7 heterocyclyl), —(C1-C9 alkyl)(C3-C7 heterocycloalkenyl), —(C1-C9 alkyl)(C6-C10 aryl), —(C1-C9 alkyl)(C4-C9 heteroaryl), —(C1-C9 alkyl)COR⁶, —(C0-C9 alkyl)(C₆H₄)OR⁷, or —(CO)R⁸;

wherein R⁴ and R⁵, when present, are independently C1-C9 alkyl;

R⁶, when present, is hydrogen, C1-C4 alkyl, C2-C4 alkenyl, C1-C4 haloalkyl, C1-C4 cyanoalkyl, C1-C4 hydroxyalkyl, C1-C4 alkoxy, C1-C4 haloalkoxy, C1-C4 alkylamino, C1-C4 aminoalkyl, or (C1-C4)(C1-C4) dialkylamino;

R⁷, when present, is hydrogen, C1-C9 alkyl, C2-C9 alkenyl, C2-C9 haloalkyl, C2-C9 cyanoalkyl, C2-C9 hydroxyalkyl, C2-C9 haloalkoxy, C2-C9 alkoxy, C2-C9 alkylamino, C3-C8 cycloalkyl, C3-C8 cycloalkenyl, C3-C7 heterocyclyl, C3-C7 heterocycloalkenyl, C6-C10 aryl, or C4-C9 heteroaryl;

R⁸, when present, is hydrogen, C1-C9 alkyl, C2-C9 alkenyl, C2-C9 haloalkyl, C2-C9 cyanoalkyl, C2-C9 hydroxyalkyl, C2-C9 haloalkoxy, C2-C9 alkoxy, C2-C9 alkylamino, C3-C8 cycloalkyl, C3-C8 cycloalkenyl, C3-C7 heterocyclyl, C3-C7 heterocycloalkenyl, C6-C10 aryl, or C4-C9 heteroaryl;

or a pharmaceutically-acceptable salt thereof; wherein M⁺ corresponds to a cation such as sodium and the like.

In some aspects of the prodrugs of Formula (VII), when R¹ is hydrogen and R² is methyl, R³ is not isopropyl, propyl, butyl, pentyl, benzyl, or -methylcyclohexane.

In a further aspect, the amine prodrugs can have a structure represented by Formula (VIII):

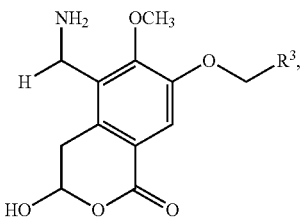

(VIII)

wherein $R^3$ is hydrogen, C1-C4 alkyl, C2-C4 alkenyl, C2-C4 haloalkyl, C2-C4 alkoxy, —(C1-C4 alkyl)$NR^4R^5$, C3-C8 cycloalkyl, C3-C7 heterocyclyl, C6-C10 aryl, C4-C9 heteroaryl, —(C1-C4 alkyl)(C6-C10 aryl), —(C1-C4 alkyl)(C4-C9 heteroaryl), —(CO—C4 alkyl)($C_6H_4$)$OR^7$, or —(CO)$R^8$; wherein $R^4$ and $R^5$, when present, are independently C1-C4 alkyl; $R^7$, when present, is hydrogen or C1-C4 alkyl; and $R^8$, when present, is hydrogen, C1-C4 alkyl, C2-C4 haloalkyl, C2-C4 hydroxyalkyl, C2-C4 haloalkoxy, C2-C4 alkoxy, C3-C8 cycloalkyl, C3-C7 heterocyclyl, C3-C7 heterocycloalkenyl, C6-C10 aryl, or C4-C9 heteroaryl.

A variety of other prodrugs can be used. In general, it is contemplated that prodrugs of the compounds can be those in which the aldehyde group is converted to another reversibly-reacting functional group as one of skill in the art would appreciate.

3. Pharmaceutically-Acceptable Salts

In one aspect, the compounds can be in the form of a pharmaceutically-acceptable salt. Non-limiting examples of pharmaceutically-acceptable salts are mineral acid (hydrochloric acid, hydrobromic acid, phosphoric acid, and the like) salts, organic acid (acetic acid, propionic acid, glutamic acid, citric acid and the like) salts, and quaternary ammonium (methyl iodide, ethyl iodide, and the like) salts. Other non-limiting examples include, but are not limited to, sulfate, citrate, acetate, oxalate, chloride, bromide, iodide, nitrate, bisulfate, phosphate, acid phosphate, phosphonic acid, isonicotinate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. Still other salts include, but are not limited to, salts with inorganic bases including alkali metal salts such as sodium salts, and potassium salts; alkaline earth metal salts such as calcium salts, and magnesium salts; aluminum salts; and ammonium salts. Other salts with organic bases include salts with diethylamine, diethanolamine, meglumine, and N,N'-dibenzylethylenediamine. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

Pharmaceutically-acceptable salts of the compounds can be salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts. Similarly, acid addition salts, such as mineral acids, organic carboxylic and organic sulfonic acids, e.g., hydrochloric acid, methanesulfonic acid, maleic acid, are also contemplated. Neutral forms of the compounds can be regenerated by contacting the salt with a base or acid and isolating the parent compound in a conventional manner.

4. Example Compounds

Specific non-limiting examples of the compounds include those listed in Table 1.

TABLE 1

EXAMPLE COMPOUNDS

| Identifier | Structure |
|---|---|
| ZFX-C-25 | 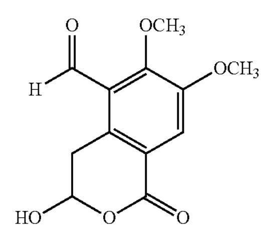 [SMILES: COc1cc2c(c(C=O)c1OC)CC(O)OC2=O] |
| ZFX-C-16 | 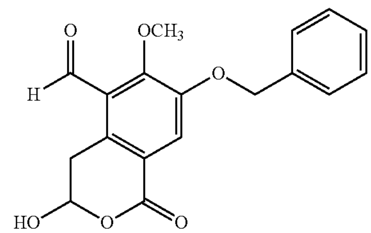 [SMILES: COc1c(OCc2ccccc2)cc2c(c1C=O)CC(O)OC2=O] |

TABLE 1-continued

EXAMPLE COMPOUNDS

| Identifier | Structure |
| --- | --- |
| ZFX-C-100 | 3-hydroxy-8-methoxy-7-(pyridin-4-ylmethoxy)-1-oxo-isochroman-5-carbaldehyde |
| ZFX-C-90 | 3-hydroxy-8-methoxy-7-((4-methylbenzyl)oxy)-1-oxo-isochroman-5-carbaldehyde |
| ZFX-C-99 | 3-hydroxy-8-methoxy-7-((4-methoxybenzyl)oxy)-1-oxo-isochroman-5-carbaldehyde |
| ZFX-C-125 | 3-hydroxy-8-methoxy-7-((3-methoxybenzyl)oxy)-1-oxo-isochroman-5-carbaldehyde |
| ZFX-C-127 | 3-hydroxy-8-methoxy-7-((2-methoxybenzyl)oxy)-1-oxo-isochroman-5-carbaldehyde |
| ZFX-C-92 | 7-((4-cyanobenzyl)oxy)-3-hydroxy-8-methoxy-1-oxo-isochroman-5-carbaldehyde |

TABLE 1-continued

EXAMPLE COMPOUNDS

| Identifier | Structure |
|---|---|
| ZFX-C-126 | 3-hydroxy-6-methoxy-5-formyl-7-((4-(trifluoromethyl)benzyl)oxy)isochroman-1-one |
| ZFX-C-140 | 3-hydroxy-6-methoxy-5-formyl-7-((4-(trifluoromethoxy)benzyl)oxy)isochroman-1-one |
| ZFX-C-147 | 3-hydroxy-6-methoxy-5-formyl-7-((4-fluorobenzyl)oxy)isochroman-1-one |
| ZFX-C-149 | 3-hydroxy-6-methoxy-5-formyl-7-((4-iodobenzyl)oxy)isochroman-1-one |
| ZFX-C-114 | 3-hydroxy-6-methoxy-5-formyl-7-((4-chlorobenzyl)oxy)isochroman-1-one |
| ZFX-C-141 | 3-hydroxy-6-methoxy-5-formyl-7-((4-bromobenzyl)oxy)isochroman-1-one |

TABLE 1-continued

| EXAMPLE COMPOUNDS | |
|---|---|
| Identifier | Structure |
| ZFX-C-154 | (structure) |
| ZFX-C-113 | (structure) |
| ZFX-C-155 | (structure) |
| ZFX-C-135 | (structure) |
| ZFX-D-66 | (structure) |

TABLE 1-continued

EXAMPLE COMPOUNDS

| Identifier | Structure |
| --- | --- |
| ZFX-D-111 | 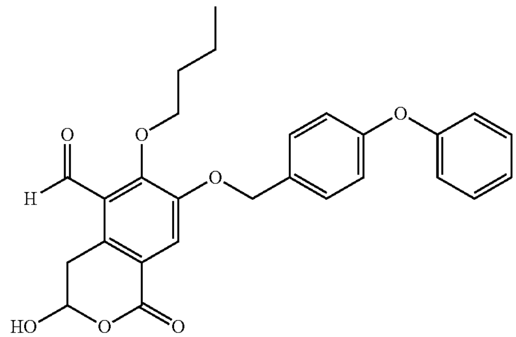 [SMILES: CCCCOc1c(OCc2ccc(Oc3ccccc3)cc2)cc2c(c1C=O)CC(O)OC2=O] |
| ZFX-C-172 | 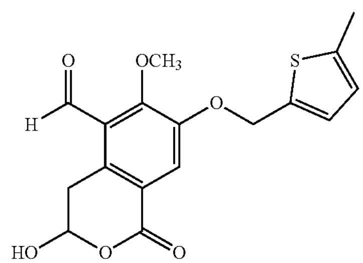 [SMILES: COc1c(OCc2ccc(C)s2)cc2c(c1C=O)CC(O)OC2=O] |
| ZFX-C-186 | 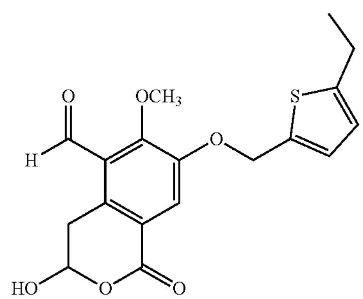 [SMILES: CCc1ccc(COc2cc3c(c(C=O)c2OC)CC(O)OC3=O)s1] |
| ZFX-D-51 | 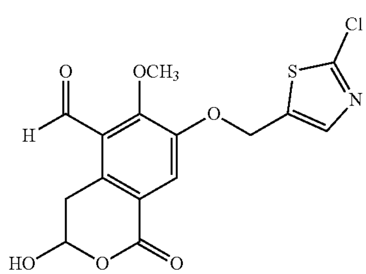 [SMILES: COc1c(OCc2cnc(Cl)s2)cc2c(c1C=O)CC(O)OC2=O] |
| ZFX-C-93 | 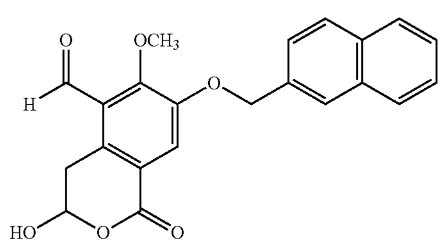 [SMILES: COc1c(OCc2ccc3ccccc3c2)cc2c(c1C=O)CC(O)OC2=O] |

TABLE 1-continued

EXAMPLE COMPOUNDS

| Identifier | Structure |
|---|---|
| NHB-1078 | 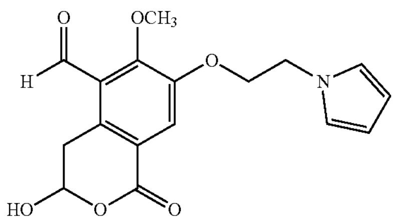 [SMILES: COc1c(OCCn2cccc2)cc2c(c1C=O)CC(O)OC2=O] |
| ZFX-C-86 | 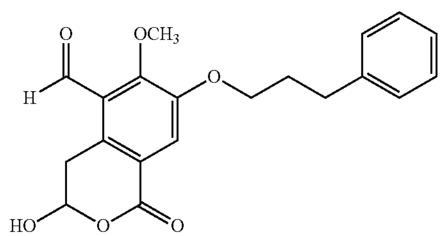 [SMILES: COc1c(OCCCc2ccccc2)cc2c(c1C=O)CC(O)OC2=O] |
| ZFX-C-181 | 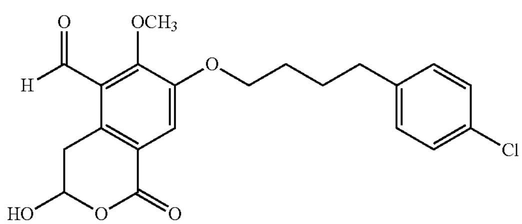 [SMILES: COc1c(OCCCCc2ccc(Cl)cc2)cc2c(c1C=O)CC(O)OC2=O] |
| ZFX-C-182 | 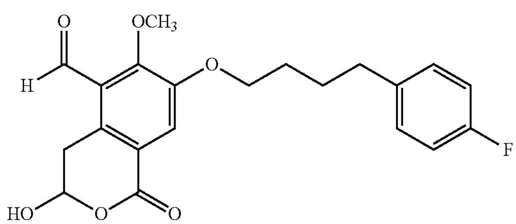 [SMILES: COc1c(OCCCCc2ccc(F)cc2)cc2c(c1C=O)CC(O)OC2=O] |
| ZFX-C-30 | 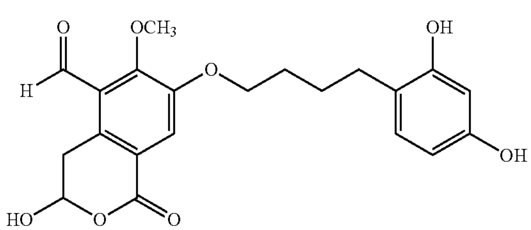 [SMILES: COc1c(OCCCCc2ccc(O)cc2O)cc2c(c1C=O)CC(O)OC2=O] |
| ZFX-C-32 | 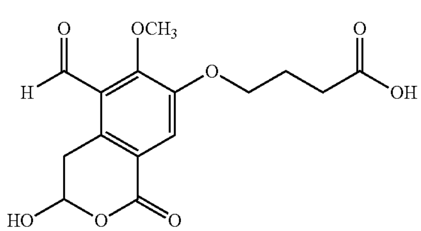 [SMILES: COc1c(OCCCC(=O)O)cc2c(c1C=O)CC(O)OC2=O] |

TABLE 1-continued

EXAMPLE COMPOUNDS

| Identifier | Structure |
|---|---|
| ZFX-C-104 | (structure) |
| ZFX-C-150 | (structure) |
| NHB-1074 | (structure) |
| ZFX-D-76 | (structure) |
| ZFX-D-88 | (structure) |
| ZFX-D-87 | (structure) |
| NHB-1093 | (structure) |

TABLE 1-continued

| EXAMPLE COMPOUNDS | |
|---|---|
| Identifier | Structure |
| NHB-1094 | *(structure: isochromanone with CHO, OCH₃, and OCH₂-cyclobutyl substituents, 3-OH)* |
| NHB-1109 | *(structure: isochromanone with CHO, OCH₃, and OCH₂-cyclopentyl substituents, 3-OH)* |
| ZFX-D-50 | *(structure: isochromanone with CHO, OCH₃, and O-CH₂-C(=O)-benzofuran-2-yl substituents, 3-OH)* |
| SCB-P426 | *(structure: isochromanone with CHO, OCH₃, and OCH₂-cycloheptyl substituents, 3-OH)* |
| NHB-1119 | *(structure: isochromanone with CHO, OCH₃, and OCH₂-cyclobutenyl substituents, 3-OH)* |

5. Methods of Making the Compounds

The disclosed compounds can be prepared through a variety of methods. It should be understood that the disclosed compounds are not limited by their method of preparation and that the methods described herein are purely exemplarily. In one aspect, the compounds can be prepared according to Scheme 1.

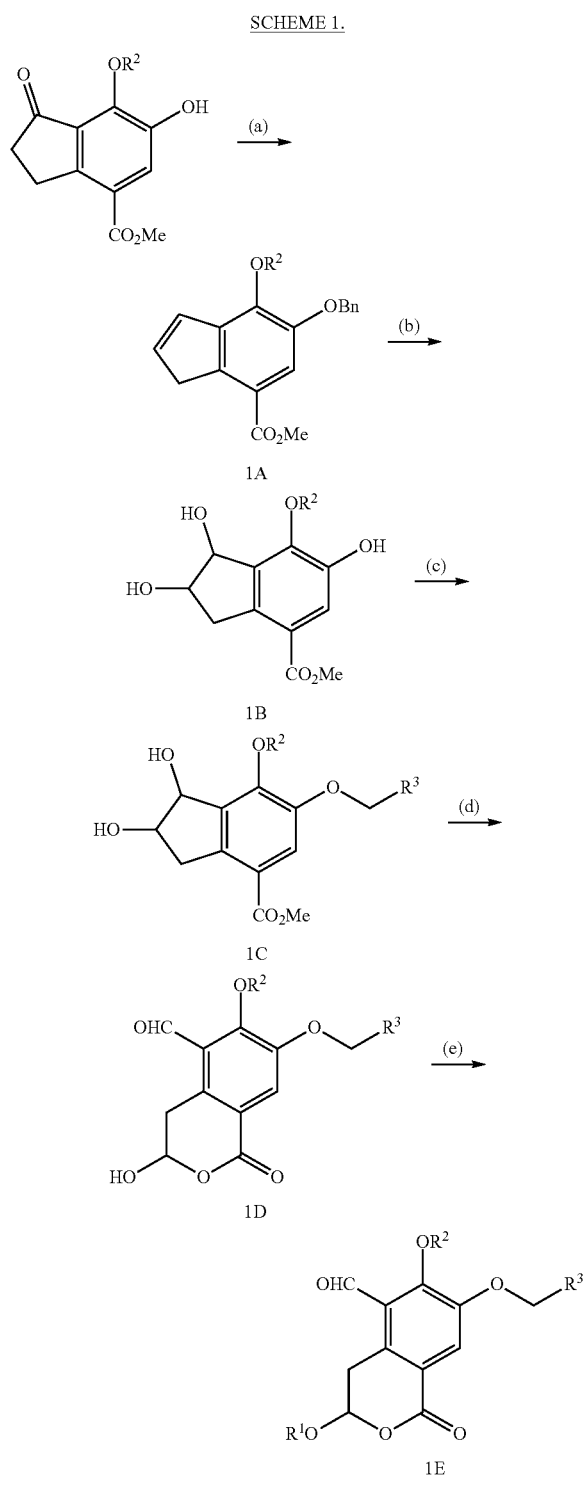

A variety of compounds represented by the general structure 1E can be prepared starting from commercially available indanone and derivatives thereof. In one aspect, in step (a), treatment of the indanone or derivative thereof with benzyl bromide or another suitable protecting group under basic conditions followed by reduction with sodium borohydride or another suitable reducing agent can provide the corresponding alcohol intermediate. Dehydration of the alcohol intermediate in the presence of p-toluenesulfonic acid or another suitable acid can provide alkenes corresponding to the general structure 1A.

In one aspect, in step (b), dihydroxylation of the olefin corresponding to general structure 1A with AD-mix-α in the presence of methanesulfonamide followed by hydrogenolysis can provide triols corresponding to general structure 1B. In one aspect, in step (c), alkylation of compounds corresponding to general structure 1B with an appropriate halide (i.e., $XCH_2R^3$) under basic conditions can provide ethers of general structure 1C.

In one aspect, in step (d), saponification of compounds of general structure 1C followed by oxidation with sodium periodate ($NaIO_4$) or another suitable oxidant can provide lactols corresponding to general structure 1D. Optionally, when $R^1$ is a substituent other than hydrogen, step (e) can be performed to alkylate the hydroxyl group on compounds of general structure 1D to provide compounds corresponding to general structure 1E. Such alkylation reactions can be performed, for example, using a suitable alkyl halide (i.e., $XR^1$), with a suitable base such as $K_2CO_3$ in a solvent such as DMF.

In a further aspect, the compounds can be prepared according to Scheme 2.

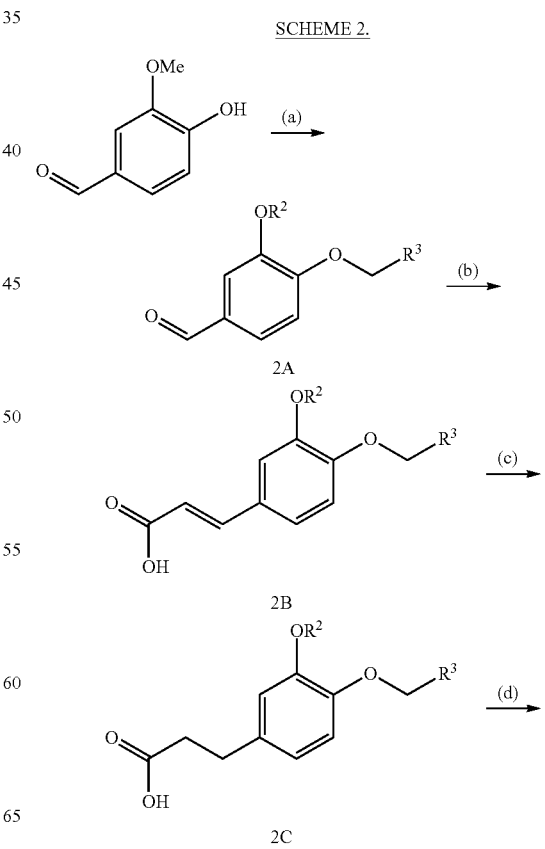

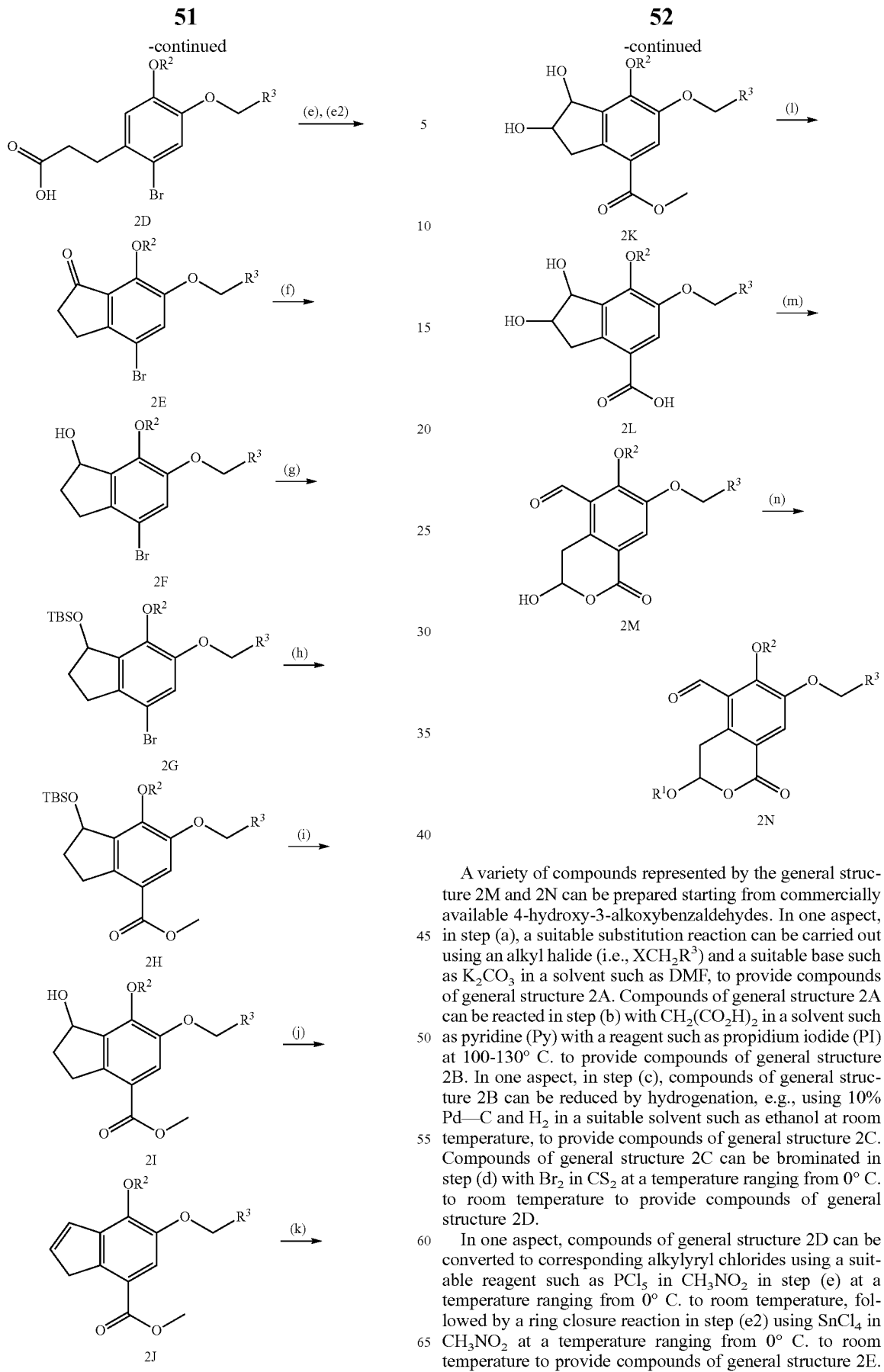

A variety of compounds represented by the general structure 2M and 2N can be prepared starting from commercially available 4-hydroxy-3-alkoxybenzaldehydes. In one aspect, in step (a), a suitable substitution reaction can be carried out using an alkyl halide (i.e., $XCH_2R^3$) and a suitable base such as $K_2CO_3$ in a solvent such as DMF, to provide compounds of general structure 2A. Compounds of general structure 2A can be reacted in step (b) with $CH_2(CO_2H)_2$ in a solvent such as pyridine (Py) with a reagent such as propidium iodide (PI) at 100-130° C. to provide compounds of general structure 2B. In one aspect, in step (c), compounds of general structure 2B can be reduced by hydrogenation, e.g., using 10% Pd—C and $H_2$ in a suitable solvent such as ethanol at room temperature, to provide compounds of general structure 2C. Compounds of general structure 2C can be brominated in step (d) with $Br_2$ in $CS_2$ at a temperature ranging from 0° C. to room temperature to provide compounds of general structure 2D.

In one aspect, compounds of general structure 2D can be converted to corresponding alkylyryl chlorides using a suitable reagent such as $PCl_5$ in $CH_3NO_2$ in step (e) at a temperature ranging from 0° C. to room temperature, followed by a ring closure reaction in step (e2) using $SnCl_4$ in $CH_3NO_2$ at a temperature ranging from 0° C. to room temperature to provide compounds of general structure 2E. In one aspect, compounds of general structure 2E can be reduced in step (f) using a suitable reducing agent such as NaBH$_4$ in methanol at 0° C. to provide compounds of general structure 2F. The alcohol on compounds of general structure 2F can be protected in step (g) with a suitable protecting group such as TBS using TBSCl and imidazole, with DMAP in methylene chloride at room temperature to provide compounds of general structure 2G. Compounds of general structure 2G can be converted in step (h) to compounds of general structure 2H using a strong base such as n-BuLi, with ClCO$_2$CH$_3$ in THE at reduced temperature (e.g., −78° C. to room temperature).

The protecting group, e.g., TBS, on compounds of general structure 2H can be removed in step (i) with a suitable reagent such as HIO$_4$ in THE and water at room temperature to provide compounds of general structure 21. Compounds of general structure 21 can be reduced in step (j) using a suitable reagent such a sp-TSOH in methylene chloride at 80° C. to provide compounds of general structure 2J. Compounds of general structure 2J can then be hydroxylated in step (k) using a suitable reagent such as AD-mix-α in CH$_3$SO$_2$NH$_2$ with t-BuOH—H$_2$O at a temperature ranging from 0° C. to room temperature to provide compounds of general structure 2K. Compounds of general structure 2K can be converted to corresponding carboxylic acids of general structure 2L in step (1) using a suitable base such as KOH (e.g., 2 mol/L) in a solvent such as C$_2$H$_5$OH at 80° C.

Compounds of general structure 2L can be converted into compounds corresponding to general structure 2M in step (m) using a suitable reagent such as NaIO$_4$ in a solvent such as 1,4-dioxane-H$_2$O at room temperature. Optionally, when R$^1$ is not hydrogen, step (n) can be performed to alkylate the hydroxyl group on compounds of general structure 2M to provide compounds corresponding to general structure 2N. Such alkylation reactions can be performed, for example, using a suitable alkyl halide (i.e., XR$^1$), with a suitable base such as K$_2$CO$_3$ in a solvent such as DMF.

6. Pharmaceutically-Acceptable Carriers and Dosage Forms

In various aspects, the compounds can be administered to a subject as a composition or formulation comprising a pharmaceutically-acceptable carrier. Non-limiting examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants.

Pharmaceutically-acceptable carries can also comprise adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms can be made by forming microencapsule matrices of the compounds in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations can also be prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

In some aspects, the pharmaceutically-acceptable carrier can include an excipient. Suitable excipients include, without limitation, saccharides, for example, glucose, lactose, or sucrose, mannitol, or sorbitol, cellulose derivatives, and/or calcium phosphate, for example, tricalcium phosphate or acidic calcium phosphate.

In further aspects, the pharmaceutically-acceptable carrier can include a binder. Suitable binders include, without limitation, tare compounds such as starch paste, for example, corn, wheat, rice, and potato starch, gelatin, tragacanth, methylcellulose, hydroxypropyl methylcellulose, carboxymethylcellulose, and/or polyvinylpyrrolidone. In still further aspects, there can be a disintegrating agent, such as the aforementioned starches and carboxymethyl starch, crosslinked polyvinylpyrrolidone, agar, or alginic acid or a salt thereof, such as sodium alginate.

In some aspects, the pharmaceutically-acceptable carrier can include an additive. Examples of additives include, but are not limited to, diluents, buffers, binders, surface-active agents, lubricants, humectants, pH adjusting agents, preservatives (including anti-oxidants), emulsifiers, occlusive agents, opacifiers, antioxidants, colorants, flavoring agents, gelling agents, thickening agents, stabilizers, and surfactants, among others. Thus, in various further aspects, the additive is vitamin E, gum acacia, citric acid, *stevia* extract powder, Luo Han Gou, Monoammonium Glycyrhizinate, Ammonium Glycyrrhizinate, honey, or combinations thereof. In a still further aspect, the additive is a flavoring agent, a binder, a disintegrant, a bulking agent, or silica. In a further aspect, the additive can include flowability-control agents and lubricants, such as silicon dioxide, talc, stearic acid and salts thereof, such as magnesium stearate or calcium stearate, and/or propylene glycol.

In various aspects, when the compounds are formulated for oral use, such as for example, a tablet, pill, or capsule, the composition can include a coating layer that is resistant to gastric acid. Such a layer, in various aspects, can include a concentrated solution of saccharides that can comprise gum arabic, talc, polyvinylpyrrolidone, polyethylene glycol, and/or titanium dioxide, and suitable organic solvents or salts thereof.

Dosage forms can comprise the compounds or a pharmaceutically-acceptable salt or prodrug thereof, together in combination with a pharmaceutically acceptable excipient, such as a preservative, buffer, saline, or phosphate buffered saline. Dosage forms can be made using conventional pharmaceutical manufacturing and compounding techniques. Dosage forms can comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol). A dosage form formulated for injectable use can have a disclosed composition or a product of a disclosed method of making, suspended in sterile saline solution for injection together with a preservative.

C. METHODS

1. Methods of Treating, Preventing, or Delaying Progression of Disorders Responsive to PTPRD Inhibition In one aspect, the compounds can be useful in treating, preventing, or delaying the progression of a variety of disorders. In one aspect, the compounds are useful for treating, preventing, or delaying the progression of a disorder responsive to inhibition of receptor-type tyrosine-protein phosphatase delta (PTPRD). Thus, in one aspect, disclosed is a method for treating, preventing, or delaying the progression of a disorder responsive to inhibition of receptor-type tyrosine-protein phosphatase delta (PTPRD), the method comprising administering to a subject in need thereof an effective amount of a compound represented by Formula (I):

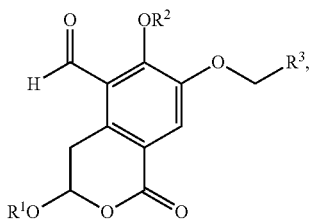

wherein $R^1$ is hydrogen, C1-C4 alkyl, C2-C4 alkenyl, C1-C4 haloalkyl, C1-C4 cyanoalkyl, C1-C4 hydroxyalkyl, C2-C4 alkoxy, C2-C4 haloalkoxy, C1-C4 alkylamino, C1-C4 acetyl, or (C1-C4)(C1-C4) dialkylamino; $R^2$ is C1-C4 alkyl, C2-C4 alkenyl, C1-C4 haloalkyl, C1-C4 cyanoalkyl, C1-C4 hydroxyalkyl, C2-C4 alkoxy, C2-C4 haloalkoxy, C1-C4 alkylamino, or (C1-C4)(C1-C4) dialkylamino;
$R^3$ is hydrogen, C1-C9 alkyl, C2-C9 alkenyl, C2-C9 haloalkyl, C2-C9 cyanoalkyl, C2-C9 hydroxyalkyl, C2-C9 alkoxy, C2-C9 haloalkoxy, C2-C9 alkylamino, —(C1-C9 alkyl)NR⁴R⁵, C3-C8 cycloalkyl, C3-C8 cycloalkenyl, C3-C7 heterocyclyl, C3-C7 heterocycloalkenyl, C6-C10 aryl, C4-C9 heteroaryl, —(C1-C9 alkyl)(C3-C8 cycloalkyl), —(C1-C9 alkyl)(C3-C8 cycloalkenyl), —(C1-C9 alkyl)(C3-C7 heterocyclyl), —(C1-C9 alkyl)(C3-C7 heterocycloalkenyl), —(C1-C9 alkyl)(C6-C10 aryl), —(C1-C9 alkyl)(C4-C9 heteroaryl), —(C1-C9 alkyl)COR⁶, —(C0-C9 alkyl)(C₆H₄)OR⁷, or —(CO)R⁸;
wherein $R^4$ and $R^5$, when present, are independently C1-C9 alkyl;
$R^6$, when present, is hydrogen, C1-C4 alkyl, C2-C4 alkenyl, C1-C4 haloalkyl, C1-C4 cyanoalkyl, C1-C4 hydroxyalkyl, C1-C4 alkoxy, C1-C4 haloalkoxy, C1-C4 alkylamino, C1-C4 aminoalkyl, or (C1-C4)(C1-C4) dialkylamino;
$R^7$, when present, is hydrogen, C1-C9 alkyl, C2-C9 alkenyl, C2-C9 haloalkyl, C2-C9 cyanoalkyl, C2-C9 hydroxyalkyl, C2-C9 haloalkoxy, C2-C9 alkoxy, C2-C9 alkylamino, C3-C8 cycloalkyl, C3-C8 cycloalkenyl, C3-C7 heterocyclyl, C3-C7 heterocycloalkenyl, C6-C10 aryl, or C4-C9 heteroaryl;
$R^8$, when present, is hydrogen, C1-C9 alkyl, C2-C9 alkenyl, C2-C9 haloalkyl, C2-C9 cyanoalkyl, C2-C9 hydroxyalkyl, C2-C9 haloalkoxy, C2-C9 alkoxy, C2-C9 alkylamino, C3-C8 cycloalkyl, C3-C8 cycloalkenyl, C3-C7 heterocyclyl, C3-C7 heterocycloalkenyl, C6-C10 aryl, or C4-C9 heteroaryl;
or a pharmaceutically-acceptable salt or prodrug thereof.

In a further aspect, disclosed is a method for treating, preventing, or delaying the progression of a disorder responsive to inhibition of receptor-type tyrosine-protein phosphatase delta (PTPRD), the method comprising administering to a subject in need thereof an effective amount of a compound represented by Formula (I), wherein $R^1$ is hydrogen or C1-C2 alkyl; $R^2$ is C1-C2 alkyl; and $R^3$ is hydrogen, C1-C4 alkyl, C2-C4 alkenyl, C2-C4 haloalkyl, C2-C4 alkoxy, —(C1-C4 alkyl)NR⁴R⁵, —(C1-C4 alkyl)COR⁶, C3-C8 cycloalkyl, C3-C7 heterocyclyl, C6-C10 aryl, C4-C9 heteroaryl, —(C1-C4 alkyl)(C6-C10 aryl), —(C1-C4 alkyl)(C4-C9 heteroaryl), —(CO—C4 alkyl)(C₆H₄)OR⁷, or —(CO)R⁸; wherein $R^4$ and $R^5$, when present, are independently C1-C4 alkyl; $R^6$, when present, is hydrogen or C1-C4 alkyl; $R^7$, when present, is hydrogen or C1-C4 alkyl; and $R^8$, when present, is hydrogen, C1-C4 alkyl, C2-C4 alkenyl, C2-C4 haloalkyl, C2-C4 cyanoalkyl, C2-C4 hydroxyalkyl, C2-C4 haloalkoxy, C2-C4 alkoxy, C2-C9 alkylamino, C3-C8 cycloalkyl, C3-C8 cycloalkenyl, C3-C7 heterocyclyl, C3-C7 heterocycloalkenyl, C6-C10 aryl, or C4-C9 heteroaryl.

In a further aspect, disclosed is a method for treating, preventing, or delaying the progression of a disorder responsive to inhibition of receptor-type tyrosine-protein phosphatase delta (PTPRD), the method comprising administering to a subject in need thereof an effective amount of a compound represented by Formula (II):

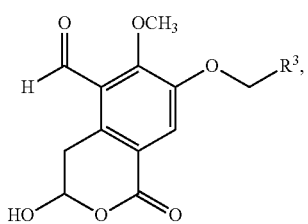

wherein $R^3$ is hydrogen, C1-C4 alkyl, C2-C4 alkenyl, C2-C4 haloalkyl, C2-C4 alkoxy, —(C1-C4 alkyl)NR⁴R⁵, C3-C8 cycloalkyl, C3-C7 heterocyclyl, C6-C10 aryl, C4-C9 heteroaryl, —(C1-C4 alkyl)(C6-C10 aryl), —(C1-C4 alkyl)(C4-C9 heteroaryl), —(CO—C4 alkyl)(C₆H₄)OR⁷, or —(CO)R⁸;
wherein $R^4$ and $R^5$, when present, are independently C1-C4 alkyl;
$R^7$, when present, is hydrogen or C1-C4 alkyl; and
$R^8$, when present, is hydrogen, C1-C4 alkyl, C2-C4 haloalkyl, C2-C4 hydroxyalkyl, C2-C4 haloalkoxy, C2-C4 alkoxy, C3-C8 cycloalkyl, C3-C7 heterocyclyl, C3-C7 heterocycloalkenyl, C6-C10 aryl, or C4-C9 heteroaryl.

In a further aspect, disclosed is a method for treating, preventing, or delaying the progression of a disorder responsive to inhibition of receptor-type tyrosine-protein phosphatase delta (PTPRD), the method comprising administering to a subject in need thereof an effective amount of a compound represented by Formula (II), wherein $R^3$ is C4-C5 cycloalkyl, C6 aryl, or C4-C5 heteroaryl.

In a further aspect, disclosed is a method for treating, preventing, or delaying the progression of a disorder responsive to inhibition of receptor-type tyrosine-protein phosphatase delta (PTPRD), the method comprising administering to a subject in need thereof an effective amount of a compound represented by Formula (I) or Formula (II), wherein $R^3$ is hydrogen or has a structure represented by the formula:

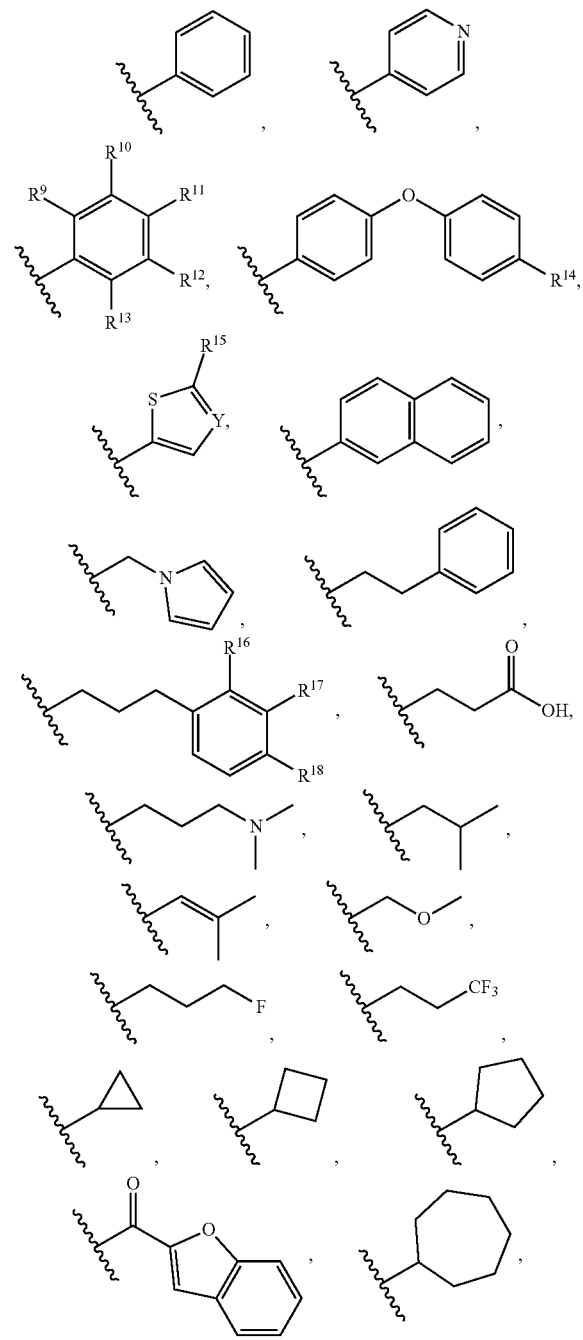

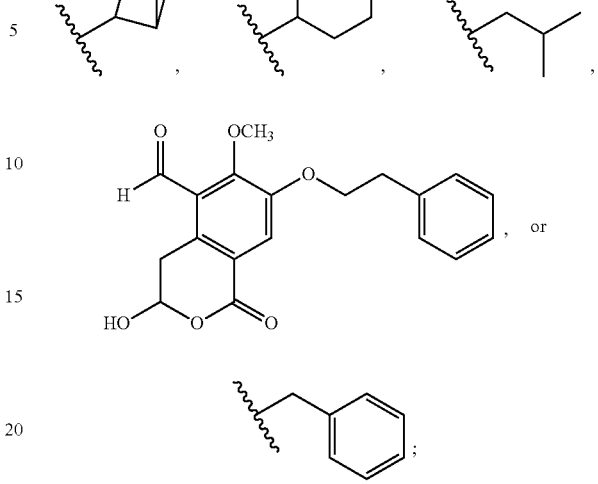

wherein $R^9$-$R^{13}$, when present, are independently hydrogen, methyl, —OCH$_3$, —CN, —CF$_3$, —OCF$_3$, or halide; $R^{14}$, when present, is hydrogen or halide; $R^{15}$, when present, is methyl or halide; Y, when present, is CH or N; and $R^{16-18}$, when present, are independently hydrogen, hydroxyl, or halide.

In a further aspect, disclosed is a method for treating, preventing, or delaying the progression of a disorder responsive to inhibition of receptor-type tyrosine-protein phosphatase delta (PTPRD), the method comprising administering to a subject in need thereof an effective amount of a compound represented by Formula (I) or Formula (II), wherein $R^3$ has a structure represented by the formula:

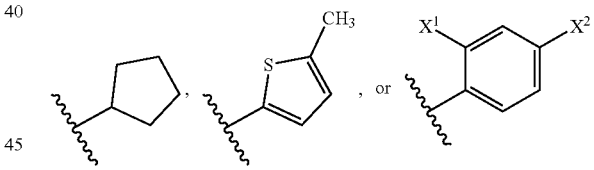

wherein $X^1$ and $X^2$, when present, are independently —Cl, —Br, —I, or —F.

In a further aspect, disclosed is a method for treating, preventing, or delaying the progression of a disorder responsive to inhibition of receptor-type tyrosine-protein phosphatase delta (PTPRD), the method comprising administering to a subject in need thereof an effective amount of a compound represented by the following formulae:

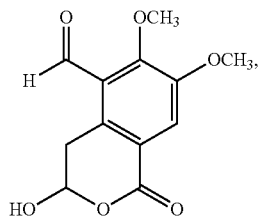

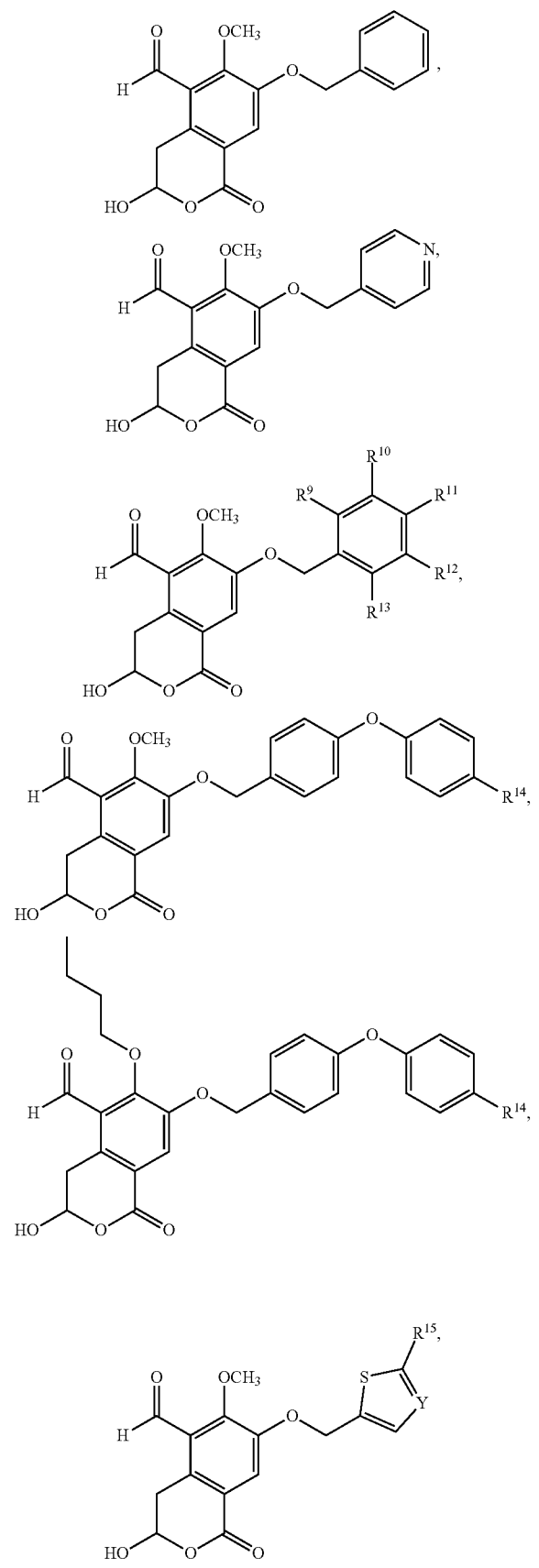
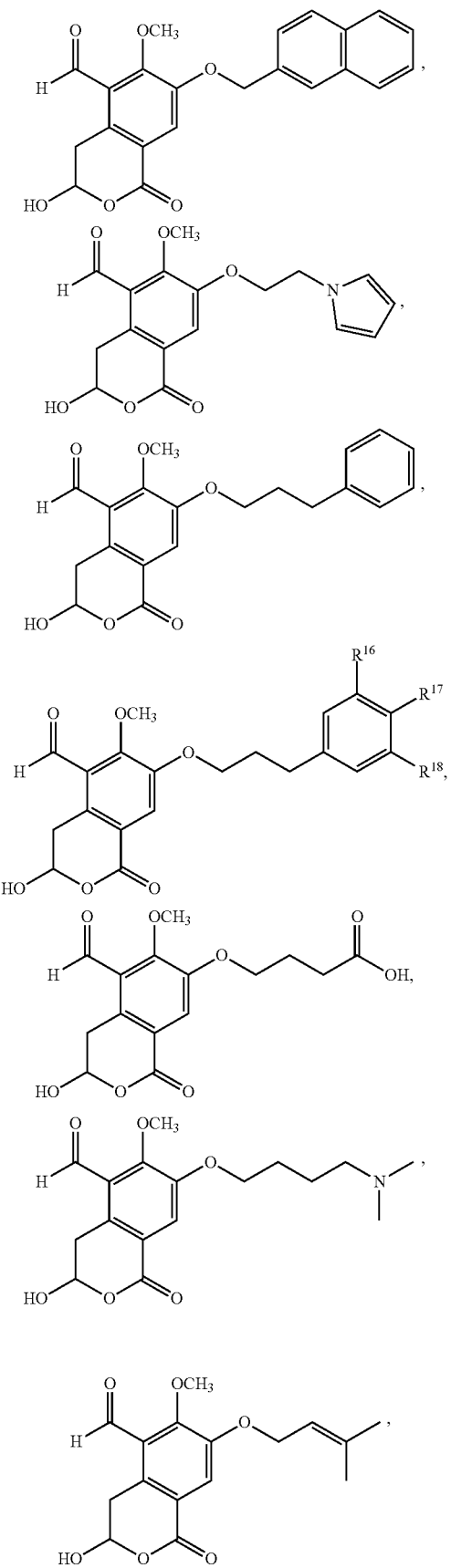

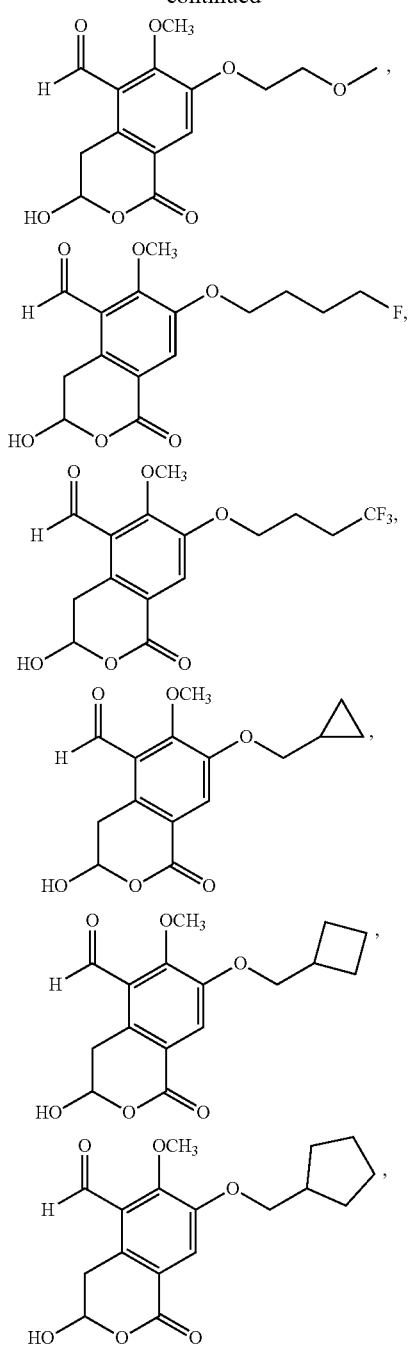

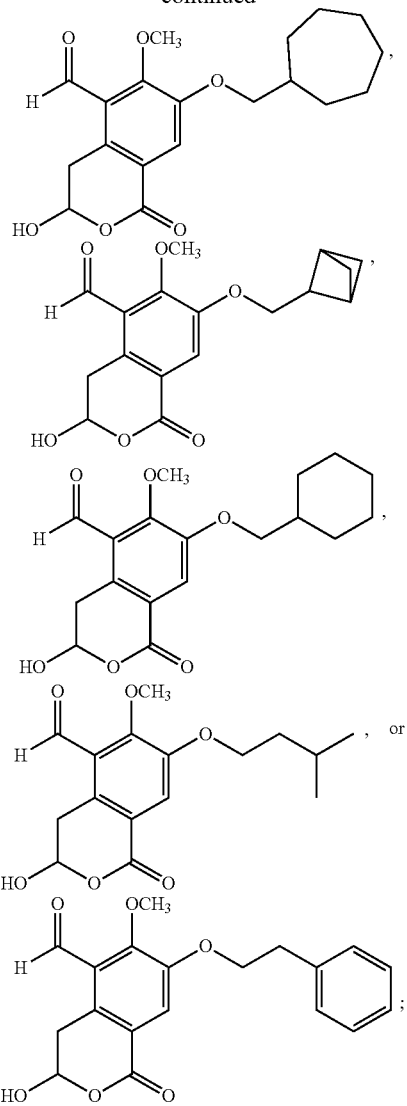

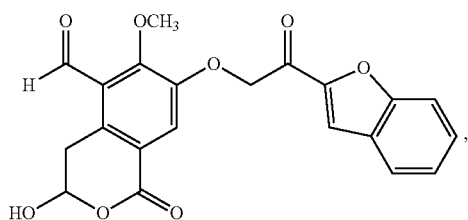

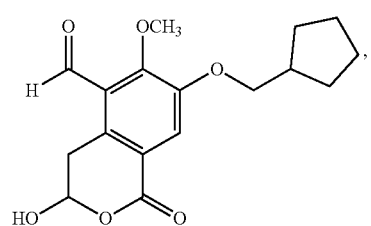

wherein $R^9$-$R^{13}$, when present, are independently hydrogen, methyl, —OCH$_3$, —CN, —CF$_3$, —OCF$_3$, or halide; $R^{14}$, when present, is hydrogen or halide; $R^{15}$, when present, is methyl or halide; Y, when present, is CH or N; and $R^{16-18}$, when present, are independently hydrogen, hydroxyl, or halide.

In a further aspect, disclosed is a method for treating, preventing, or delaying the progression of a disorder responsive to inhibition of receptor-type tyrosine-protein phosphatase delta (PTPRD), the method comprising administering to a subject in need thereof an effective amount of a compound represented by the following formulae:

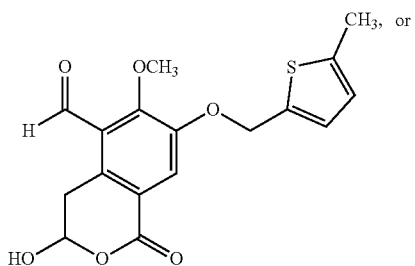

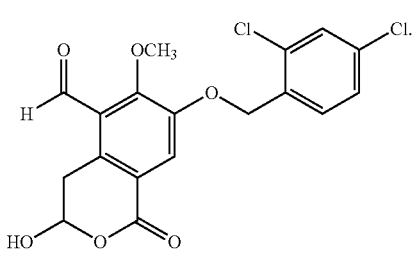

In a further aspect, disclosed is a method for treating, preventing, or delaying the progression of a disorder responsive to inhibition of receptor-type tyrosine-protein phosphatase delta (PTPRD), the method comprising administering to a subject in need thereof an effective amount of a compound represented by the following formula:

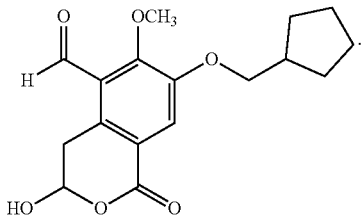

A variety of disorders can be responsive to inhibition of PTPRD activity. Non-limiting examples include nicotine dependence and substance-use disorder, e.g., stimulant-use disorder or opioid-use disorder. Without wishing to be bound by theory, it is believed that the disclosed compounds, when administered to a subject in need thereof, inhibit PTPRD and thus reduce the reward associated with certain addictive substances. For example, the disclosed compounds can inhibit PTPRD effects on phosphorylation of conserved tyrosines in human proteins that include the addiction-associated kinase cyclin-dependent protein kinase 5 (Cdk5). The disclosed compounds are also useful for treating obesity and metabolic syndrome.

2. Methods of Treating, Preventing, or Delaying Progression of Substance-Use Disorders, Nicotine Dependence, Obesity, or Metabolic Syndrome In a further aspect, disclosed is a method for treating, preventing, or delaying the progression of a substance-use disorder, nicotine dependence, obesity, or metabolic syndrome, the method comprising administering to a subject in need thereof an effective amount of a compound represented by Formula (I):

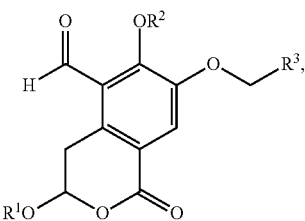

wherein $R^1$ is hydrogen, C1-C4 alkyl, C2-C4 alkenyl, C1-C4 haloalkyl, C1-C4 cyanoalkyl, C1-C4 hydroxyalkyl, C2-C4 alkoxy, C2-C4 haloalkoxy, C1-C4 alkylamino, C1-C4 acetyl, or (C1-C4)(C1-C4) dialkylamino;

$R^2$ is C1-C4 alkyl, C2-C4 alkenyl, C1-C4 haloalkyl, C1-C4 cyanoalkyl, C1-C4 hydroxyalkyl, C2-C4 alkoxy, C2-C4 haloalkoxy, C1-C4 alkylamino, or (C1-C4)(C1-C4) dialkylamino;

$R^3$ is hydrogen, C1-C9 alkyl, C2-C9 alkenyl, C2-C9 haloalkyl, C2-C9 cyanoalkyl, C2-C9 hydroxyalkyl, C2-C9 alkoxy, C2-C9 haloalkoxy, C2-C9 alkylamino, —(C1-C9 alkyl)$NR^4R^5$, C3-C8 cycloalkyl, C3-C8 cycloalkenyl, C3-C7 heterocyclyl, C3-C7 heterocycloalkenyl, C6-C10 aryl, C4-C9 heteroaryl, —(C1-C9 alkyl)(C3-C8 cycloalkyl), —(C1-C9 alkyl)(C3-C8 cycloalkenyl), —(C1-C9 alkyl)(C3-C7 heterocyclyl), —(C1-C9 alkyl)(C3-C7 heterocycloalkenyl), —(C1-C9 alkyl)(C6-C10 aryl), —(C1-C9 alkyl)(C4-C9 heteroaryl), —(C1-C9 alkyl)$COR^6$, —(C0-C9 alkyl)($C_6H_4$)$OR^7$, or —(CO)$R^8$;

wherein $R^4$ and $R^5$, when present, are independently C1-C9 alkyl; $R^6$, when present, is hydrogen, C1-C4 alkyl, C2-C4 alkenyl, C1-C4 haloalkyl, C1-C4 cyanoalkyl, C1-C4 hydroxyalkyl, C1-C4 alkoxy, C1-C4 haloalkoxy, C1-C4 alkylamino, C1-C4 aminoalkyl, or (C1-C4)(C1-C4) dialkylamino;

$R^7$, when present, is hydrogen, C1-C9 alkyl, C2-C9 alkenyl, C2-C9 haloalkyl, C2-C9 cyanoalkyl, C2-C9 hydroxyalkyl, C2-C9 haloalkoxy, C2-C9 alkoxy, C2-C9 alkylamino, C3-C8 cycloalkyl, C3-C8 cycloalkenyl, C3-C7 heterocyclyl, C3-C7 heterocycloalkenyl, C6-C10 aryl, or C4-C9 heteroaryl;

$R^8$, when present, is hydrogen, C1-C9 alkyl, C2-C9 alkenyl, C2-C9 haloalkyl, C2-C9 cyanoalkyl, C2-C9 hydroxyalkyl, C2-C9 haloalkoxy, C2-C9 alkoxy, C2-C9 alkylamino, C3-C8 cycloalkyl, C3-C8 cycloalkenyl, C3-C7 heterocyclyl, C3-C7 heterocycloalkenyl, C6-C10 aryl, or C4-C9 heteroaryl;

or a pharmaceutically-acceptable salt or prodrug thereof.

In a further aspect, disclosed is a method for treating, preventing, or delaying the progression of a substance-use disorder, nicotine dependence, obesity, or metabolic syndrome, the method comprising administering to a subject in need thereof an effective amount of a compound represented by Formula (I), wherein $R^1$ is hydrogen or C1-C2 alkyl; $R^2$ is C1-C2 alkyl; and $R^3$ is hydrogen, C1-C4 alkyl, C2-C4 alkenyl, C2-C4 haloalkyl, C2-C4 alkoxy, —(C1-C4 alkyl)$NR^4R^5$, —(C1-C4 alkyl)$COR^6$, C3-C8 cycloalkyl, C3-C7 heterocyclyl, C6-C10 aryl, C4-C9 heteroaryl, —(C1-C4 alkyl)(C6-C10 aryl), —(C1-C4 alkyl)(C4-C9 heteroaryl), —(CO—C4 alkyl)($C_6H_4$)$OR^7$, or —(CO)$R^8$; wherein $R^4$ and $R^5$, when present, are independently C1-C4 alkyl; $R^6$, when present, is C1-C4 alkyl; $R^7$, when present, is hydrogen or C1-C4 alkyl; and $R^8$, when present, is hydrogen, C1-C4 alkyl, C2-C4 alkenyl, C2-C4 haloalkyl, C2-C4 cyanoalkyl, C2-C4 hydroxyalkyl, C2-C4 haloalkoxy, C2-C4 alkoxy, C2-C9 alkylamino, C3-C8 cycloalkyl, C3-C8 cycloalkenyl, C3-C7 heterocyclyl, C3-C7 heterocycloalkenyl, C6-C10 aryl, or C4-C9 heteroaryl.

In a further aspect, disclosed is a method for treating, preventing, or delaying the progression of a substance-use disorder, nicotine dependence, obesity, or metabolic syndrome, the method comprising administering to a subject in need thereof an effective amount of a compound represented by Formula (II):

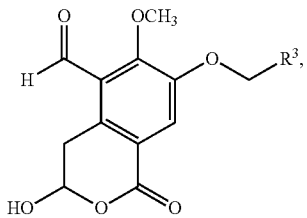

wherein $R^3$ is hydrogen, C1-C4 alkyl, C2-C4 alkenyl, C2-C4 haloalkyl, C2-C4 alkoxy, —(C1-C4 alkyl)NR$^4$R$^5$, C3-C8 cycloalkyl, C3-C7 heterocyclyl, C6-C10 aryl, C4-C9 heteroaryl, —(C1-C4 alkyl)(C6-C10 aryl), —(C1-C4 alkyl)(C4-C9 heteroaryl), —(CO—C4 alkyl)(C$_6$H$_4$)OR$^7$, or —(CO)R$^8$;

wherein $R^4$ and $R^5$, when present, are independently C1-C4 alkyl;

$R^7$, when present, is hydrogen or C1-C4 alkyl; and $R^8$, when present, is hydrogen, C1-C4 alkyl, C2-C4 haloalkyl, C2-C4 hydroxyalkyl, C2-C4 haloalkoxy, C2-C4 alkoxy, C3-C8 cycloalkyl, C3-C7 heterocyclyl, C3-C7 heterocycloalkenyl, C6-C10 aryl, or C4-C9 heteroaryl.

In a further aspect, disclosed is a method for treating, preventing, or delaying the progression of a substance-use disorder, nicotine dependence, obesity, or metabolic syndrome, the method comprising administering to a subject in need thereof an effective amount of a compound represented by Formula (II), wherein $R^3$ is C4-C5 cycloalkyl, C6 aryl, or C4-C5 heteroaryl.

In a further aspect, disclosed is a method for treating, preventing, or delaying the progression of a substance-use disorder, nicotine dependence, obesity, or metabolic syndrome, the method comprising administering to a subject in need thereof an effective amount of a compound represented by Formula (I) or Formula (II), wherein $R^3$ is hydrogen or has a structure represented by the formula:

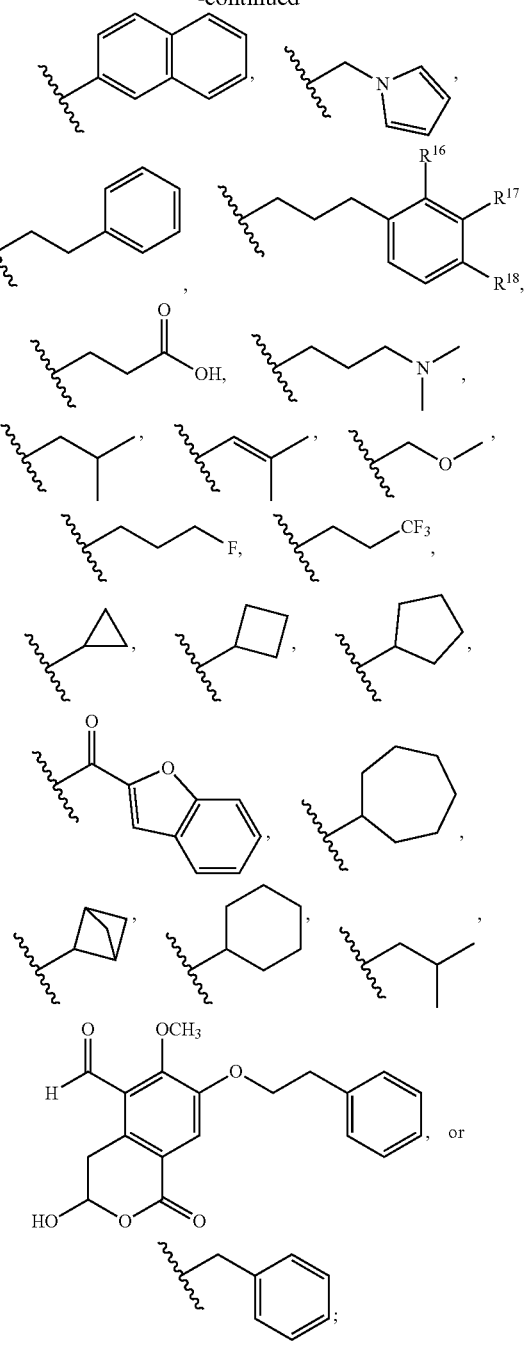

wherein $R^9$-$R^{13}$, when present, are independently hydrogen, methyl, —OCH$_3$, —CN, —CF$_3$, —OCF$_3$, or halide; $R^{14}$, when present, is hydrogen or halide; $R^{15}$, when present, is methyl or halide; Y, when present, is CH or N; and $R^{16-18}$, when present, are independently hydrogen, hydroxyl, or halide.

In a further aspect, disclosed is a method for treating, preventing, or delaying the progression of a substance-use disorder, nicotine dependence, obesity, or metabolic syndrome, the method comprising administering to a subject in need thereof an effective amount of a compound represented by Formula (I) or Formula (II), wherein $R^3$ has a structure represented by the formula:

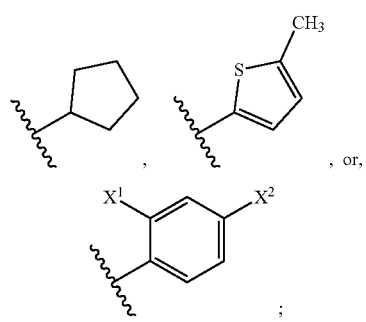

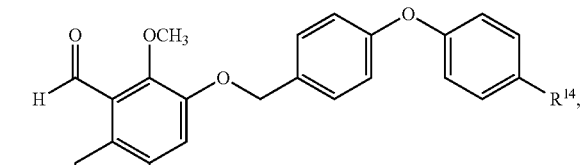

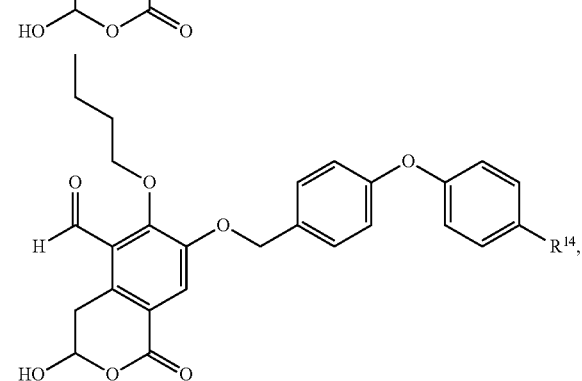

wherein $X^1$ and $X^2$, when present, are independently —Cl, —Br, —I, or —F.

In a further aspect, disclosed is a method for treating, preventing, or delaying the progression of a substance-use disorder, nicotine dependence, obesity, or metabolic syndrome, the method comprising administering to a subject in need thereof an effective amount of a compound represented by the formula:

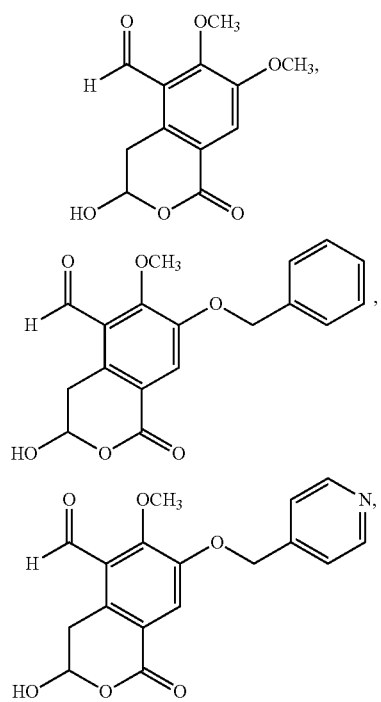

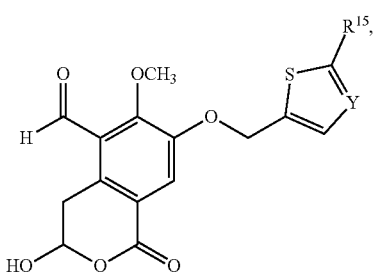

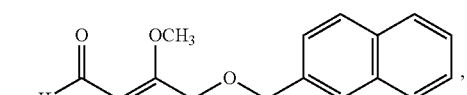

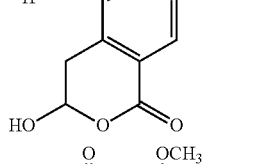

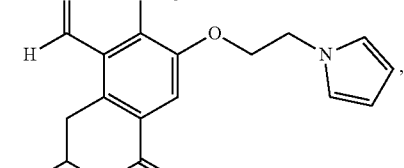

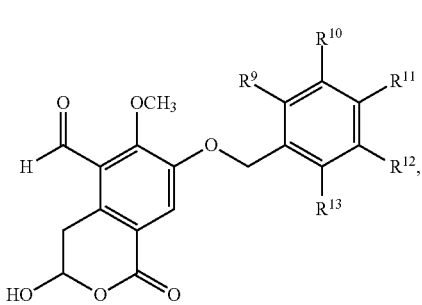

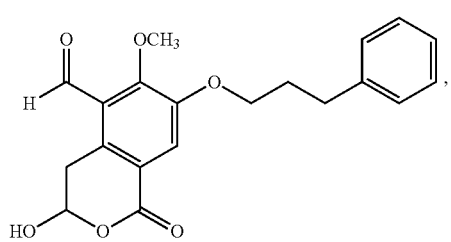

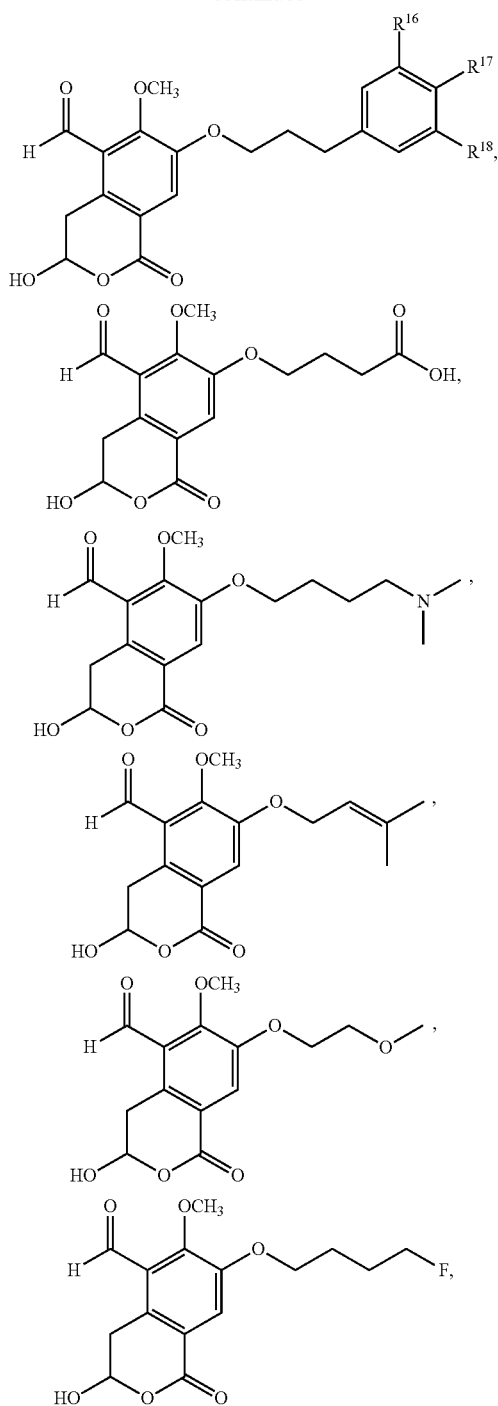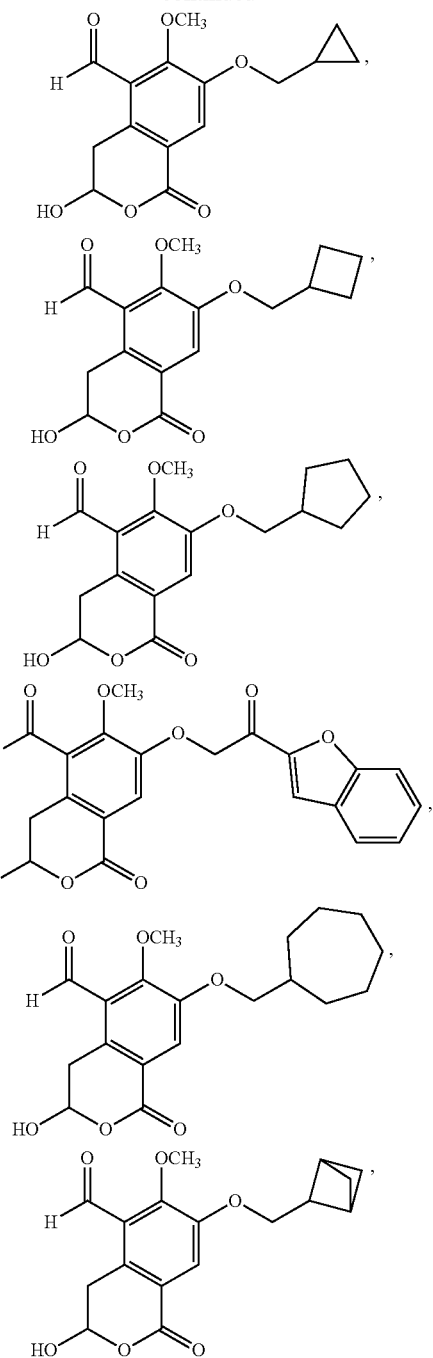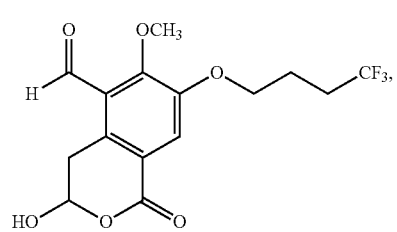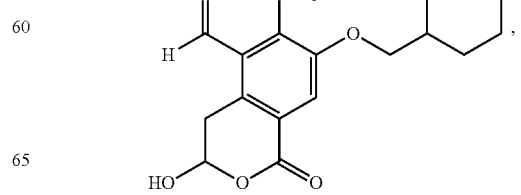

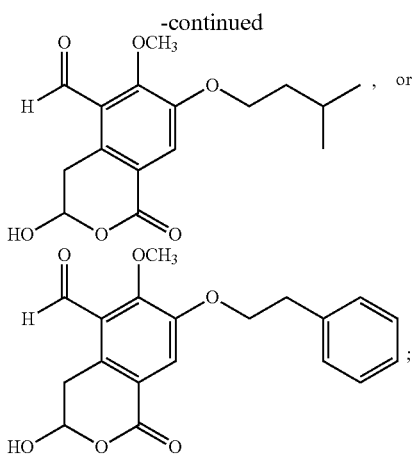
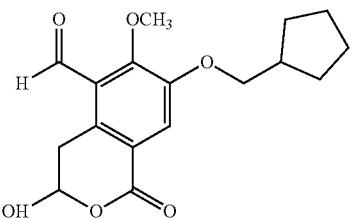 [SMILES: COc1c(OCC2CCCC2)cc2c(c1C=O)CC(O)OC2=O]

wherein $R^9$-$R^{13}$, when present, are independently hydrogen, methyl, —OCH$_3$, —CN, —CF$_3$, —OCF$_3$, or halide; $R^{14}$, when present, is hydrogen or halide; $R^{15}$, when present, is methyl or halide; Y, when present, is CH or N; and $R^{16\text{-}18}$, when present, are independently hydrogen, hydroxyl, or halide.

In a further aspect, disclosed is a method for treating, preventing, or delaying the progression of a substance-use disorder, nicotine dependence, obesity, or metabolic syndrome, the method comprising administering to a subject in need thereof an effective amount of a compound represented by the formula:

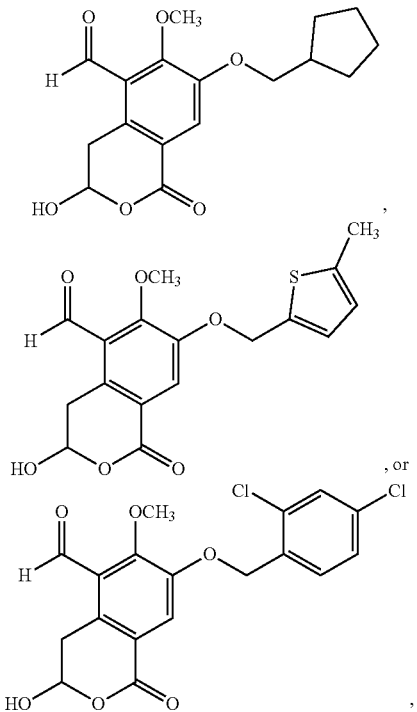

In a further aspect, disclosed is a method for treating, preventing, or delaying the progression of a substance-use disorder, nicotine dependence, obesity, or metabolic syndrome, the method comprising administering to a subject in need thereof an effective amount of a compound represented by the formula:

In one aspect, the disclosed compounds are useful for treating, preventing, or delaying the progression of a variety of substance-use disorder, nicotine dependence, obesity, or metabolic syndrome. Examples of substance-use disorders that can be treated with a disclosed compound include without limitation opioid-use disorders and stimulant-use disorders. Examples of opioid-use disorders that can be treated, prevented, or delayed in progression including without limitation disorders associated with illegal opioid use, e.g., heroin use, as well as disorders associated with synthetic opioids such fentanyl, oxycodone, hydrocodone, codeine, morphine, among others. Examples of stimulant-use disorders that can be treated with a disclosed compound include without limitation disorders associated with illegal or prescription stimulants, e.g., cocaine, amphetamines, methamphetamines, crack-cocaine, dextroamphetamine, lisdexamfetamine, stimulants prescribed for ADHD or ADD, stimulants prescribed for narcolepsy, among others.

Some patients receive opioids for the treatment of acute, temporary, or chronic pain. The disclosed compounds can prevent, in some aspects, such a subject's dependence or addiction to the opioid by reducing the reward associated with the opioid. Thus, in some aspects, the compound can be administered to a subject that is concurrently being treated with an opioid for acute or chronic pain.

In other aspects, the subject may be attempting to recover from a substance-use disorder such as opioid-use disorder. Certain subjects in recovery from such disorders are often administered an opioid-receptor agonist, such as buprenorphine or methadone, to aid in recovery and reduce withdrawal symptoms. Thus, in some aspects, the disclosed compound can be administered to a subject that is concurrently being treated with an opioid-receptor agonist such as buprenorphine or methadone.

The DSM-V (the Diagnostic and Statistical Manual of Mental Disorders). includes criteria for classifying a substance-use disorder as mild, moderate or severe. In some aspects of the methods disclosed herein, the substance-use disorder is selected from a mild substance use disorder, a moderate substance use disorder, or a severe substance use disorder. In some aspects, the substance use disorder is a mild substance use disorder. In some aspects, the substance-use disorder is a moderate substance-use disorder. In some aspects, the substance-use disorder is a severe substance-use disorder.

Similarly, in some aspects, when the subject has a nicotine dependence, the subject may have also been prescribed a nicotine withdrawal aid and taking that withdrawal aid concurrently with the administration of a disclosed compound. Likewise, the subject may be taking over-the-counter nicotine withdrawal aids, such as gums or lozenges, which deliver an amount of nicotine sufficient to reduce nicotine cravings and withdrawal leading up to an eventual nicotine-cessation period. The disclosed compounds can be continued after the subject has ceased taking the nicotine withdrawal aid, which can effectively result in reducing the reward associated with nicotine.

Without wishing to be bound by theory, it is believed that the disclosed compounds inhibit PTPRD dephosphorylation of certain substrates including those associated with addiction or dependence through an irreversible or pseudo-irreversible mechanism. Accordingly, in some aspects, the interval at which the compound is administered to the subject can range from once per day to once per week, or longer. In one aspect, the compound can be administered to the subject once every two days, once every three days, once every four days, once every five days, once every six days, once every seven days, or a longer interval.

In some aspects, the amount of the compound administered to the subject is a therapeutically-effective amount. In other aspects, the compounds are useful in preventing the development of a dependence or substance-use disorder, for example in patients being prescribed an opioid for acute or chronic paid, and thus the amount of the compound administered can be a prophylactically-effective amount, i.e., an amount sufficient to prevent the development of a nicotine dependence or substance use disorder.

The subject, in some aspects, can be a mammal. In other aspects, the subject can be a human. In a further aspect, the subject has been diagnosed with a need for treatment, prevention, or delayed progression of the disorder prior to the administering step. In a still further aspect, the method further comprises identifying a subject in need of treatment, prevention, or delayed progression of the disorder.

The compounds and pharmaceutically acceptable salts thereof can be administered to the subject having an injury to the nervous system via a variety of routes. Non-limiting examples include oral administration (e.g., as a tablet, capsule, lozenge, or troche) or intravenous administration of the compound together with a pharmaceutically-acceptable carrier.

The effective amount or dosage of the composition or an ingredient thereof can vary within wide limits. Such a dosage is adjusted to the individual requirements in each particular case including the specific composition(s) being administered and the condition being treated, as well as the subject being treated. In general, single dose compositions can contain such amounts or submultiples thereof of the composition to make up the daily dose. The dosage can be adjusted by the individual physician in the event of any contraindications. Dosage can vary, and can be administered in one or more dose administrations daily, for one or several days. In some aspects, the effective amount is a therapeutically effective amount. In a further aspect, the effective amount is a prophylactically effective amount.

In one aspect, the compounds can be administered to the subject having an injury to the nervous system in an amount generally up to about 10,000 mg per dose. In other aspects, the dose can range from about 1 mg/kg body weight to about 500 mg/kg body weight, using a 75 kg human as the subject. Dosages can be adjusted accordingly depending on the body weight of the subject. In a further aspect, the compounds can be administered to the subject in an amount ranging from about 1 mg/kg body weight to about 200 mg/kg body weight, using a 75 kg human as the subject.

3. Methods of Inhibiting PTPRD

In a further aspect, disclosed is a method for inhibiting PTPRD activity, the method comprising contacting the PTPRD or causing the PTPRD to be contacted with an effective amount of a compound represented by Formula (I):

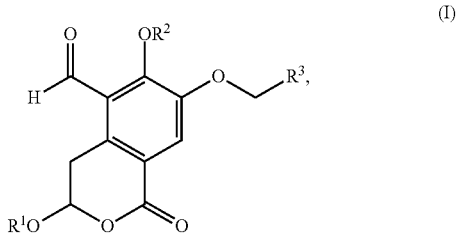

(I)

wherein $R^1$ is hydrogen, C1-C4 alkyl, C2-C4 alkenyl, C1-C4 haloalkyl, C1-C4 cyanoalkyl, C1-C4 hydroxyalkyl, C2-C4 alkoxy, C2-C4 haloalkoxy, C1-C4 alkylamino, C1-C4 acetyl, or (C1-C4)(C1-C4) dialkylamino;

$R^2$ is C1-C4 alkyl, C2-C4 alkenyl, C1-C4 haloalkyl, C1-C4 cyanoalkyl, C1-C4 hydroxyalkyl, C2-C4 alkoxy, C2-C4 haloalkoxy, C1-C4 alkylamino, or (C1-C4)(C1-C4) dialkylamino;

$R^3$ is hydrogen, C1-C9 alkyl, C2-C9 alkenyl, C2-C9 haloalkyl, C2-C9 cyanoalkyl, C2-C9 hydroxyalkyl, C2-C9 alkoxy, C2-C9 haloalkoxy, C2-C9 alkylamino, —(C1-C9 alkyl)$NR^4R^5$, C3-C8 cycloalkyl, C3-C8 cycloalkenyl, C3-C7 heterocyclyl, C3-C7 heterocycloalkenyl, C6-C10 aryl, C4-C9 heteroaryl, —(C1-C9 alkyl)(C3-C8 cycloalkyl), —(C1-C9 alkyl)(C3-C8 cycloalkenyl), —(C1-C9 alkyl)(C3-C7 heterocyclyl), —(C1-C9 alkyl)(C3-C7 heterocycloalkenyl), —(C1-C9 alkyl)(C6-C10 aryl), —(C1-C9 alkyl)(C4-C9 heteroaryl), —(C1-C9 alkyl)$COR^6$, —(C0-C9 alkyl)($C_6H_4$)$OR^7$, or —(CO)$R^8$;

wherein $R^4$ and $R^5$, when present, are independently C1-C9 alkyl;

$R^6$, when present, is hydrogen, C1-C4 alkyl, C2-C4 alkenyl, C1-C4 haloalkyl, C1-C4 cyanoalkyl, C1-C4 hydroxyalkyl, C1-C4 alkoxy, C1-C4 haloalkoxy, C1-C4 alkylamino, C1-C4 aminoalkyl, or (C1-C4)(C1-C4) dialkylamino;

$R^7$, when present, is hydrogen, C1-C9 alkyl, C2-C9 alkenyl, C2-C9 haloalkyl, C2-C9 cyanoalkyl, C2-C9 hydroxyalkyl, C2-C9 haloalkoxy, C2-C9 alkoxy, C2-C9 alkylamino, C3-C8 cycloalkyl, C3-C8 cycloalkenyl, C3-C7 heterocyclyl, C3-C7 heterocycloalkenyl, C6-C10 aryl, or C4-C9 heteroaryl;

$R^8$, when present, is hydrogen, C1-C9 alkyl, C2-C9 alkenyl, C2-C9 haloalkyl, C2-C9 cyanoalkyl, C2-C9 hydroxyalkyl, C2-C9 haloalkoxy, C2-C9 alkoxy, C2-C9 alkylamino, C3-C8 cycloalkyl, C3-C8 cycloalkenyl, C3-C7 heterocyclyl, C3-C7 heterocycloalkenyl, C6-C10 aryl, or C4-C9 heteroaryl;

or a pharmaceutically-acceptable salt or prodrug thereof.

In a further aspect, disclosed is a method for inhibiting PTPRD activity, the method comprising contacting the PTPRD or causing the PTPRD to be contacted with an effective amount of a compound represented by Formula (I), wherein $R^1$ is hydrogen or C1-C2 alkyl; $R^2$ is C1-C2 alkyl; and $R^3$ is hydrogen, C1-C4 alkyl, C2-C4 alkenyl, C2-C4 haloalkyl, C2-C4 alkoxy, —(C1-C4 alkyl)$NR^4R^5$, —(C1-C4 alkyl)$COR^6$, C3-C8 cycloalkyl, C3-C7 heterocyclyl, C6-C10 aryl, C4-C9 heteroaryl, —(C1-C4 alkyl)(C6-C10 aryl), —(C1-C4 alkyl)(C4-C9 heteroaryl), —(CO—C4 alkyl)($C_6H_4$)$OR^7$, or —(CO)$R^8$; wherein $R^4$ and $R^5$, when present, are independently C1-C4 alkyl; $R^6$, when present, is hydrogen or C1-C4 alkyl; $R^7$, when present, is hydrogen or C1-C4 alkyl; and $R^8$, when present, is hydrogen, C1-C4 alkyl, C2-C4 alkenyl, C2-C4 haloalkyl, C2-C4 cyanoalkyl, C2-C4 hydroxyalkyl, C2-C4 haloalkoxy, C2-C4 alkoxy, C2-C9 alkylamino, C3-C8 cycloalkyl, C3-C8 cycloalkenyl, C3-C7 heterocyclyl, C3-C7 heterocycloalkenyl, C6-C10 aryl, or C4-C9 heteroaryl.

In a further aspect, disclosed is a method for inhibiting PTPRD activity, the method comprising contacting the PTPRD or causing the PTPRD to be contacted with an effective amount of a compound represented by Formula (II):

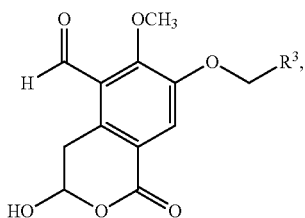

(II)

wherein R³ is hydrogen, C1-C4 alkyl, C2-C4 alkenyl, C2-C4 haloalkyl, C2-C4 alkoxy, —(C1-C4 alkyl) NR⁴R⁵, C3-C8 cycloalkyl, C3-C7 heterocyclyl, C6-C10 aryl, C4-C9 heteroaryl, —(C1-C4 alkyl)(C6-C10 aryl), —(C1-C4 alkyl)(C4-C9 heteroaryl), —(CO—C4 alkyl)(C₆H₄)OR⁷, or —(CO)R⁸;

wherein R⁴ and R⁵, when present, are independently C1-C4 alkyl;

R⁷, when present, is hydrogen or C1-C4 alkyl; and

R⁸, when present, is hydrogen, C1-C4 alkyl, C2-C4 haloalkyl, C2-C4 hydroxyalkyl, C2-C4 haloalkoxy, C2-C4 alkoxy, C3-C8 cycloalkyl, C3-C7 heterocyclyl, C3-C7 heterocycloalkenyl, C6-C10 aryl, or C4-C9 heteroaryl.

In a further aspect, disclosed is a method for inhibiting PTPRD activity, the method comprising contacting the PTPRD or causing the PTPRD to be contacted with an effective amount of a compound represented by Formula (II), wherein R³ is C4-C5 cycloalkyl, C6 aryl, or C4-C5 heteroaryl.

In a further aspect, disclosed is a method for inhibiting PTPRD activity, the method comprising contacting the PTPRD or causing the PTPRD to be contacted with an effective amount of a compound represented by Formula (I) or Formula (II), wherein R³ is hydrogen or has a structure represented by the formula:

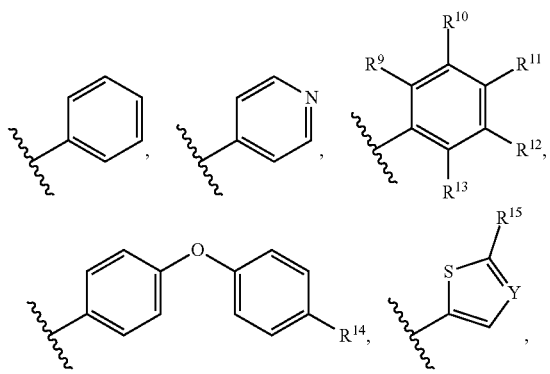

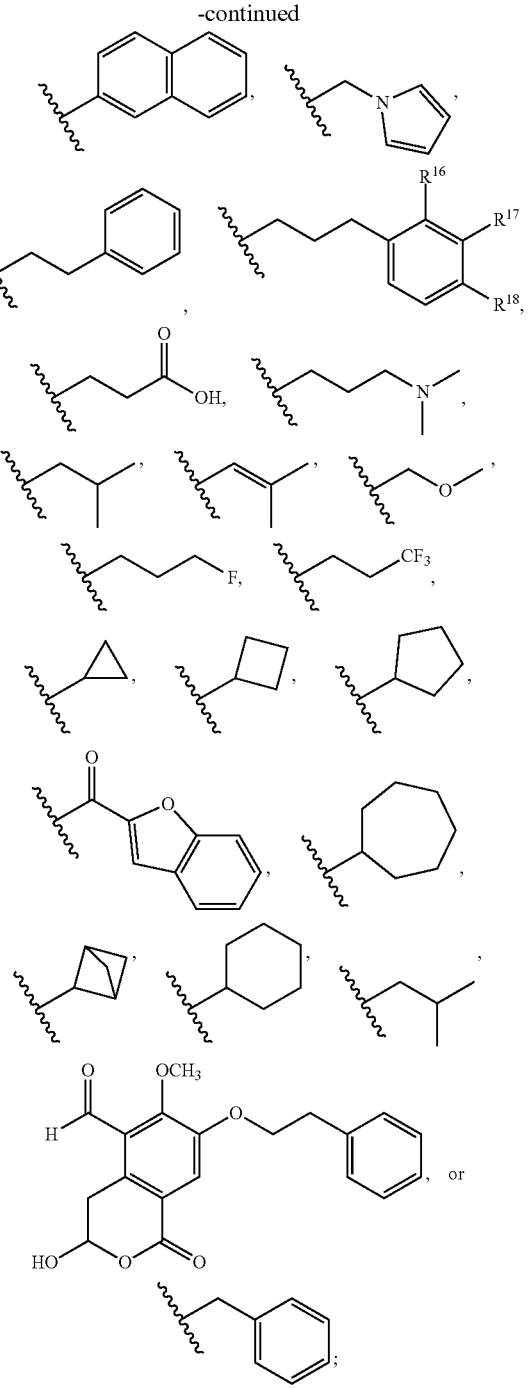

wherein R⁹-R¹³, when present, are independently hydrogen, methyl, —OCH₃, —CN, —CF₃, —OCF₃, or halide; R¹⁴, when present, is hydrogen or halide; R¹⁵, when present, is methyl or halide; Y, when present, is CH or N; and R¹⁶⁻¹⁸, when present, are independently hydrogen, hydroxyl, or halide.

In a further aspect, disclosed is a method for inhibiting PTPRD activity, the method comprising contacting the PTPRD or causing the PTPRD to be contacted with an effective amount of a compound represented by Formula (I) or Formula (II), wherein R³ has a structure represented by the formula:

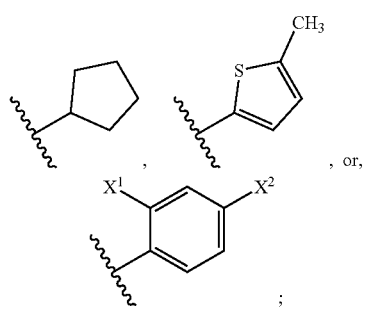
wherein $X^1$ and $X^2$, when present, are independently —Cl, —Br, —I, or —F.
In a further aspect, disclosed is a method for inhibiting PTPRD activity, the method comprising contacting the PTPRD or causing the PTPRD to be contacted with an effective amount of a compound represented by the formula:
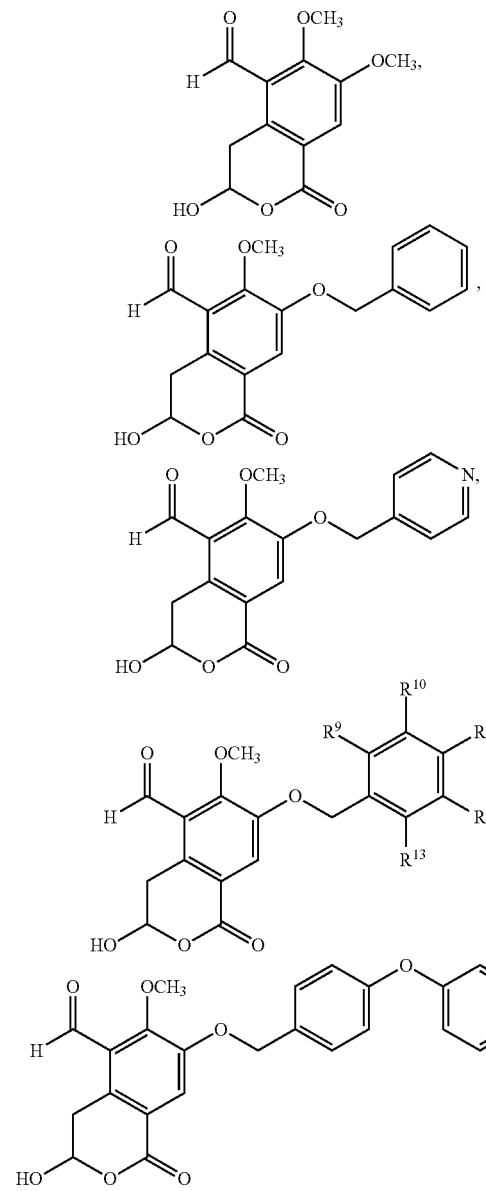
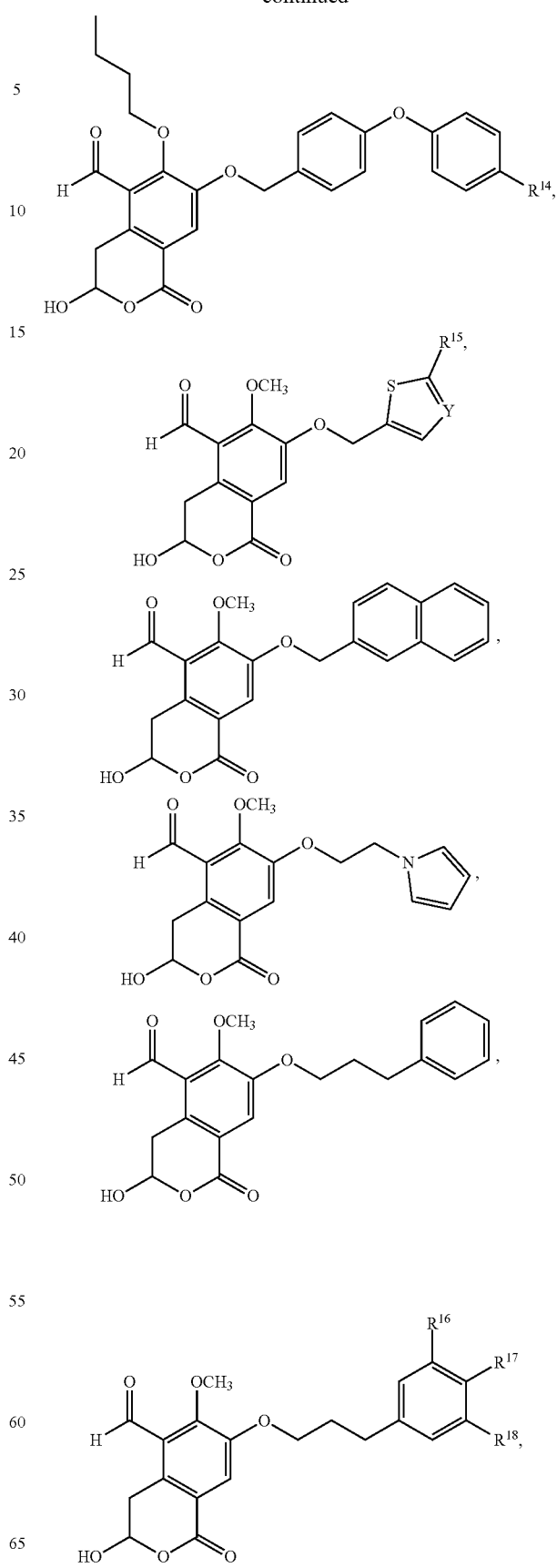

-continued
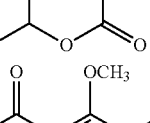
wherein $R^9$-$R^{13}$, when present, are independently hydrogen, methyl, —OCH$_3$, —CN, —CF$_3$, —OCF$_3$, or halide; $R^{14}$, when present, is hydrogen or halide; $R^{15}$, when present, is methyl or halide; Y, when present, is CH or N; and $R^{16-18}$, when present, are independently hydrogen, hydroxyl, or halide.

In a further aspect, disclosed is a method for inhibiting PTPRD activity, the method comprising contacting the PTPRD or causing the PTPRD to be contacted with an effective amount of a compound represented by the formula:

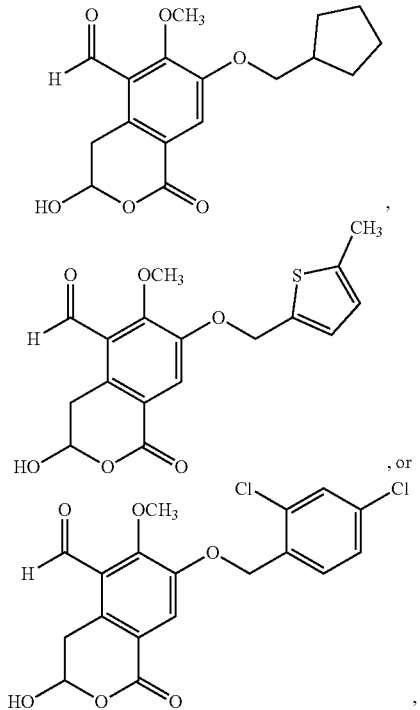

In a further aspect, disclosed is a method for inhibiting PTPRD activity, the method comprising contacting the PTPRD or causing the PTPRD to be contacted with an effective amount of a compound represented by the formula:

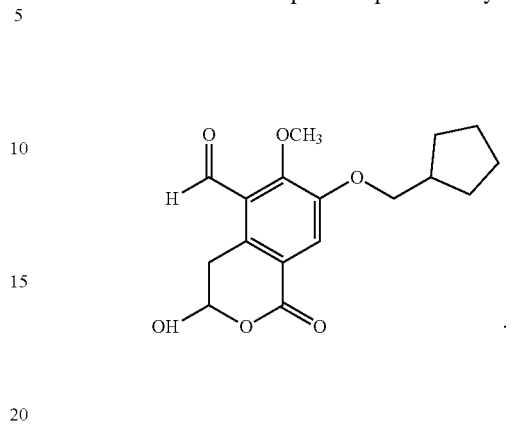

In one aspect, by contacting or causing PTPRD to be contacted with a disclosed compound, the ability of the PTPRD to dephosphorylate a substrate can be inhibited. In some aspects, the compound can inhibit the ability of PTPRD to dephosphorylate a tyrosine residue of a variety of proteins, including proteins associated with addiction related responses and reward mechanisms. Non-limiting examples include paranitrophenol phosphate (pNPP), phosphotyrosine (pY) glycogen synthase kinase 3 (pYGSK3) phosphopeptides, as well as other kinases including addiction-associated kinase cyclin-dependent protein kinase 5 (Cdk5).

Non-limiting examples of compounds that can be used with the disclosed methods include those listed in Table 2.

TABLE 2

EXAMPLE COMPOUNDS FOR METHODS

| Identifier | Structure |
|---|---|
| ZFX-C-25 | 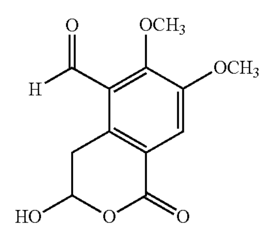 [SMILES: COc1cc2c(c(C=O)c1OC)CC(O)OC2=O] |
| ZFX-C-16 | 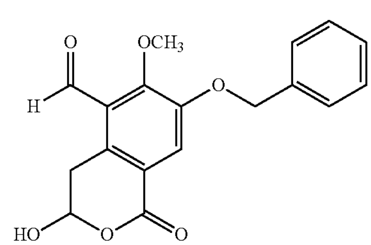 [SMILES: COc1c(OCc2ccccc2)cc2c(c1C=O)CC(O)OC2=O] |

TABLE 2-continued
EXAMPLE COMPOUNDS FOR METHODS
| Identifier | Structure |
|---|---|
| ZFX-C-100 | 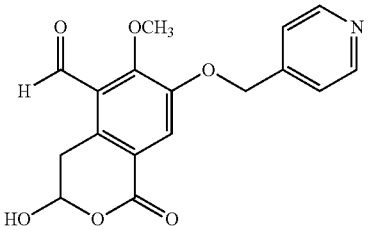 [SMILES: COc1c(OCc2ccncc2)cc2c(c1C=O)CC(O)OC2=O] |
| ZFX-C-90 | 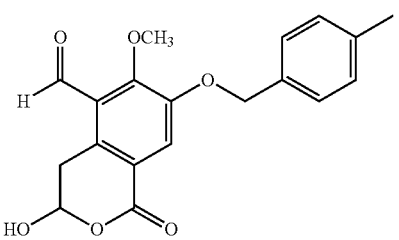 [SMILES: COc1c(OCc2ccc(C)cc2)cc2c(c1C=O)CC(O)OC2=O] |
| ZFX-C-99 | 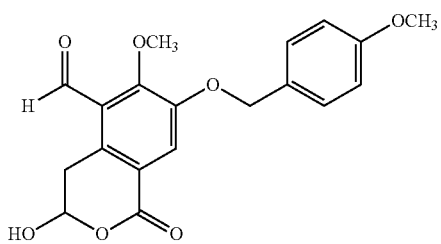 [SMILES: COc1ccc(COc2cc3c(c(C=O)c2OC)CC(O)OC3=O)cc1] |
| ZFX-C-125 | 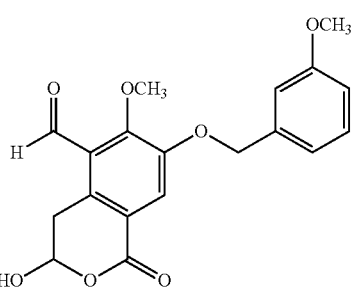 |
| ZFX-C-127 | 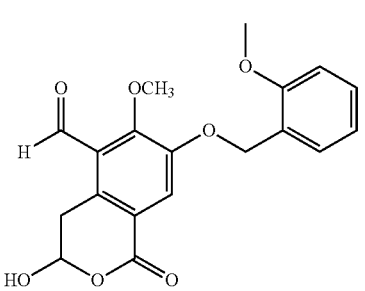 [SMILES: COc1ccccc1COc1cc2c(c(C=O)c1OC)CC(O)OC2=O] |
| ZFX-C-92 | 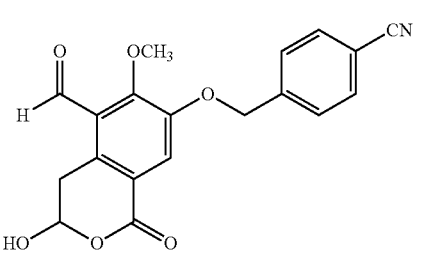 [SMILES: COc1c(OCc2ccc(C#N)cc2)cc2c(c1C=O)CC(O)OC2=O] |

TABLE 2-continued

| EXAMPLE COMPOUNDS FOR METHODS | |
| --- | --- |
| Identifier | Structure |
| ZFX-C-126 | 3-hydroxy-6-methoxy-7-((4-(trifluoromethyl)benzyl)oxy)-1-oxo-3,4-dihydro-1H-isochromene-5-carbaldehyde |
| ZFX-C-140 | 3-hydroxy-6-methoxy-7-((4-(trifluoromethoxy)benzyl)oxy)-1-oxo-3,4-dihydro-1H-isochromene-5-carbaldehyde |
| ZFX-C-147 | 7-((4-fluorobenzyl)oxy)-3-hydroxy-6-methoxy-1-oxo-3,4-dihydro-1H-isochromene-5-carbaldehyde |
| ZFX-C-149 | 3-hydroxy-7-((4-iodobenzyl)oxy)-6-methoxy-1-oxo-3,4-dihydro-1H-isochromene-5-carbaldehyde |
| ZFX-C-114 | 7-((4-chlorobenzyl)oxy)-3-hydroxy-6-methoxy-1-oxo-3,4-dihydro-1H-isochromene-5-carbaldehyde |
| ZFX-C-141 | 7-((4-bromobenzyl)oxy)-3-hydroxy-6-methoxy-1-oxo-3,4-dihydro-1H-isochromene-5-carbaldehyde |

TABLE 2-continued

EXAMPLE COMPOUNDS FOR METHODS

| Identifier | Structure |
| --- | --- |
| ZFX-C-154 | 3-hydroxy-7-((2,4-dichlorobenzyl)oxy)-8-methoxy-5-formyl-isochroman-1-one |
| ZFX-C-113 | 3-hydroxy-7-((3,4-dichlorobenzyl)oxy)-8-methoxy-5-formyl-isochroman-1-one |
| ZFX-C-155 | 3-hydroxy-7-((2,4,6-trichlorobenzyl)oxy)-8-methoxy-5-formyl-isochroman-1-one |
| ZFX-C-135 | 3-hydroxy-7-((4-phenoxybenzyl)oxy)-8-methoxy-5-formyl-isochroman-1-one |
| ZFX-D-66 | 3-hydroxy-7-((4-(4-fluorophenoxy)benzyl)oxy)-8-methoxy-5-formyl-isochroman-1-one |

TABLE 2-continued

EXAMPLE COMPOUNDS FOR METHODS

| Identifier | Structure |
| --- | --- |
| ZFX-D-111 | *3-hydroxy-6-butoxy-7-((4-phenoxybenzyl)oxy)-5-formyl-isochroman-1-one* |
| ZFX-C-172 | *3-hydroxy-6-methoxy-7-((5-methylthiophen-2-yl)methoxy)-5-formyl-isochroman-1-one* |
| ZFX-C-186 | *3-hydroxy-6-methoxy-7-((5-ethylthiophen-2-yl)methoxy)-5-formyl-isochroman-1-one* |
| ZFX-D-51 | *3-hydroxy-6-methoxy-7-((2-chlorothiazol-5-yl)methoxy)-5-formyl-isochroman-1-one* |
| ZFX-C-93 | *3-hydroxy-6-methoxy-7-(naphthalen-2-ylmethoxy)-5-formyl-isochroman-1-one* |

TABLE 2-continued

EXAMPLE COMPOUNDS FOR METHODS

| Identifier | Structure |
|---|---|
| ZFX-C-98 | 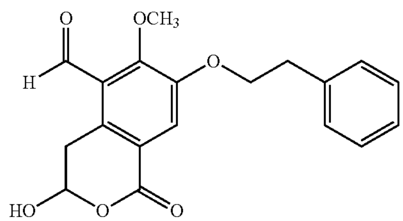 [SMILES: COc1c(OCCc2ccccc2)cc2c(c1C=O)CC(O)OC2=O] |
| NHB-1078 | 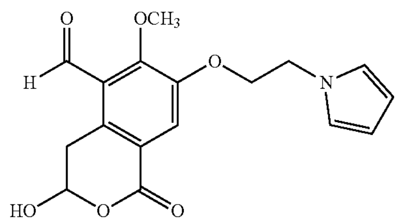 [SMILES: COc1c(OCCn2cccc2)cc2c(c1C=O)CC(O)OC2=O] |
| ZFX-C-86 | 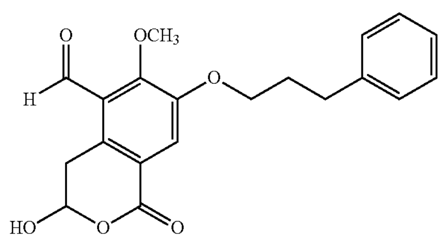 [SMILES: COc1c(OCCCc2ccccc2)cc2c(c1C=O)CC(O)OC2=O] |
| ZFX-C-181 | 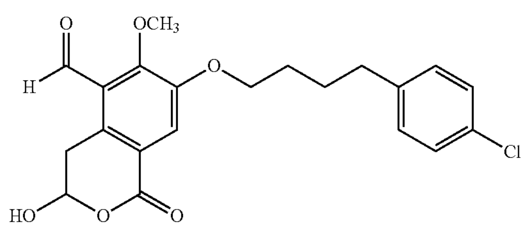 [SMILES: COc1c(OCCCCc2ccc(Cl)cc2)cc2c(c1C=O)CC(O)OC2=O] |
| ZFX-C-182 | 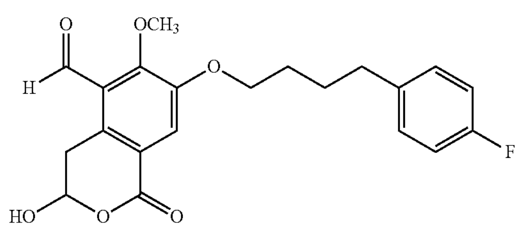 [SMILES: COc1c(OCCCCc2ccc(F)cc2)cc2c(c1C=O)CC(O)OC2=O] |
| ZFX-C-30 | 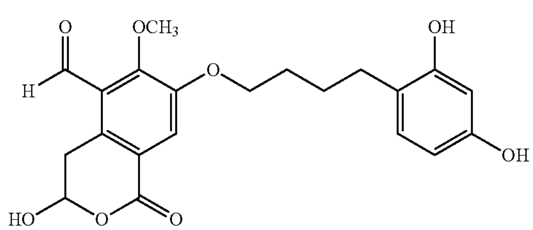 [SMILES: COc1c(OCCCCc2ccc(O)cc2O)cc2c(c1C=O)CC(O)OC2=O] |

TABLE 2-continued
EXAMPLE COMPOUNDS FOR METHODS
| Identifier | Structure |
|---|---|
| ZFX-C-32 | 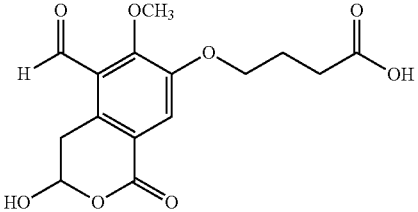 [SMILES: COc1c(OCCCC(=O)O)cc2c(c1C=O)CC(O)OC2=O] |
| ZFX-C-104 | 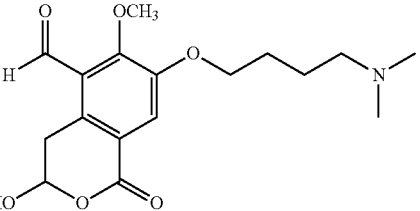 |
| ZFX-C-150 | 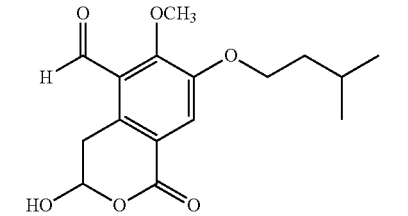 [SMILES: COc1c(OCCC(C)C)cc2c(c1C=O)CC(O)OC2=O] |
| NHB-1074 | 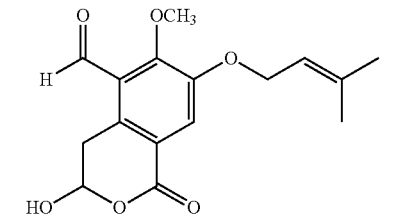 [SMILES: COc1c(OCC=C(C)C)cc2c(c1C=O)CC(O)OC2=O] |
| ZFX-D-76 | 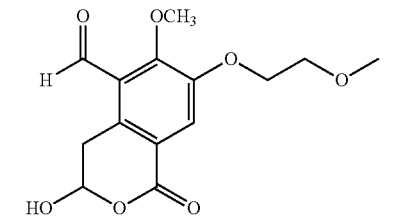 [SMILES: COCCOc1cc2c(c(C=O)c1OC)CC(O)OC2=O] |
| ZFX-D-88 | 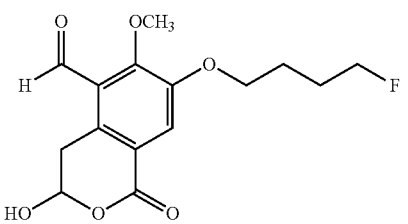 [SMILES: COc1c(OCCCCF)cc2c(c1C=O)CC(O)OC2=O] |
| ZFX-D-87 | 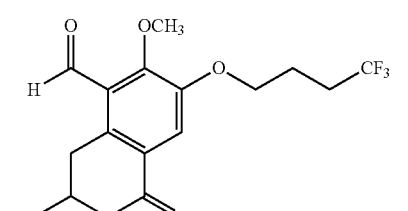 |

TABLE 2-continued

EXAMPLE COMPOUNDS FOR METHODS

| Identifier | Structure |
|---|---|
| NHB-1093 | *(structure)* |
| NHB-1094 | *(structure)* |
| NHB-1109 | *(structure)* |
| ZFX-D-50 | *(structure)* |
| NHB-1128 | *(structure)* |
| SCB-P426 | *(structure)* |

TABLE 2-continued

EXAMPLE COMPOUNDS FOR METHODS

| Identifier | Structure |
|---|---|
| NHB-1119 | 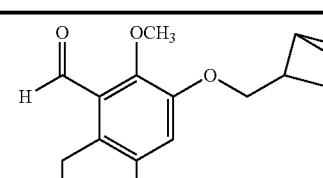 |

D. MANUFACTURE OF A MEDICAMENT

In one aspect, disclosed is the use of a compound represented by Formula (I) in the manufacture of a medicament for the treatment, prevention, or delayed progression of nicotine dependence, a substance-use disorder (e.g., a stimulant-use disorder or an opioid-use disorder), obesity, metabolic syndrome, or a disorder responsive to inhibition of PTPRD activity:

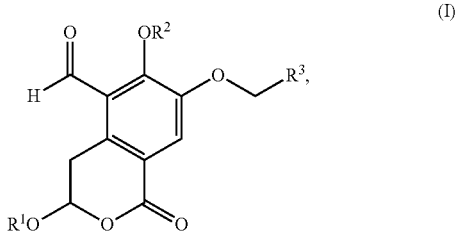

(I)

wherein $R^1$ is hydrogen, C1-C4 alkyl, C2-C4 alkenyl, C1-C4 haloalkyl, C1-C4 cyanoalkyl, C1-C4 hydroxyalkyl, C2-C4 alkoxy, C2-C4 haloalkoxy, C1-C4 alkylamino, C1-C4 acetyl, or (C1-C4)(C1-C4) dialkylamino;

$R^2$ is C1-C4 alkyl, C2-C4 alkenyl, C1-C4 haloalkyl, C1-C4 cyanoalkyl, C1-C4 hydroxyalkyl, C2-C4 alkoxy, C2-C4 haloalkoxy, C1-C4 alkylamino, or (C1-C4)(C1-C4) dialkylamino;

$R^3$ is hydrogen, C1-C9 alkyl, C2-C9 alkenyl, C2-C9 haloalkyl, C2-C9 cyanoalkyl, C2-C9 hydroxyalkyl, C2-C9 alkoxy, C2-C9 haloalkoxy, C2-C9 alkylamino, —(C1-C9 alkyl)$NR^4R^5$, C3-C8 cycloalkyl, C3-C8 cycloalkenyl, C3-C7 heterocyclyl, C3-C7 heterocycloalkenyl, C6-C10 aryl, C4-C9 heteroaryl, —(C1-C9 alkyl)(C3-C8 cycloalkyl), —(C1-C9 alkyl)(C3-C8 cycloalkenyl), —(C1-C9 alkyl)(C3-C7 heterocyclyl), —(C1-C9 alkyl)(C3-C7 heterocycloalkenyl), —(C1-C9 alkyl)(C6-C10 aryl), —(C1-C9 alkyl)(C4-C9 heteroaryl), —(C1-C9 alkyl)$COR^6$, —(C0-C9 alkyl)($C_6H_4$)$OR^7$, or —(CO)$R^8$;

wherein $R^4$ and $R^5$, when present, are independently C1-C9 alkyl;

$R^6$, when present, is hydrogen, C1-C4 alkyl, C2-C4 alkenyl, C1-C4 haloalkyl, C1-C4 cyanoalkyl, C1-C4 hydroxyalkyl, C1-C4 alkoxy, C1-C4 haloalkoxy, C1-C4 alkylamino, C1-C4 aminoalkyl, or (C1-C4)(C1-C4) dialkylamino;

$R^7$, when present, is hydrogen, C1-C9 alkyl, C2-C9 alkenyl, C2-C9 haloalkyl, C2-C9 cyanoalkyl, C2-C9 hydroxyalkyl, C2-C9 haloalkoxy, C2-C9 alkoxy, C2-C9 alkylamino, C3-C8 cycloalkyl, C3-C8 cycloalkenyl, C3-C7 heterocyclyl, C3-C7 heterocycloalkenyl, C6-C10 aryl, or C4-C9 heteroaryl;

$R^8$, when present, is hydrogen, C1-C9 alkyl, C2-C9 alkenyl, C2-C9 haloalkyl, C2-C9 cyanoalkyl, C2-C9 hydroxyalkyl, C2-C9 haloalkoxy, C2-C9 alkoxy, C2-C9 alkylamino, C3-C8 cycloalkyl, C3-C8 cycloalkenyl, C3-C7 heterocyclyl, C3-C7 heterocycloalkenyl, C6-C10 aryl, or C4-C9 heteroaryl;

or a pharmaceutically-acceptable salt or prodrug thereof.

In a further aspect, disclosed is the use of a compound represented by Formula (I) in the manufacture of a medicament for the treatment, prevention, or delayed progression of nicotine dependence, a substance-use disorder (e.g., a stimulant-use disorder or an opioid-use disorder), obesity, metabolic syndrome, or a disorder responsive to inhibition of PTPRD activity, wherein $R^1$ is hydrogen or C1-C2 alkyl; $R^2$ is C1-C2 alkyl; and $R^3$ is hydrogen, C1-C4 alkyl, C2-C4 alkenyl, C2-C4 haloalkyl, C2-C4 alkoxy, —(C1-C4 alkyl)$NR^4R^5$, —(C1-C4 alkyl)$COR^6$, C3-C8 cycloalkyl, C3-C7 heterocyclyl, C6-C10 aryl, C4-C9 heteroaryl, —(C1-C4 alkyl)(C6-C10 aryl), —(C1-C4 alkyl)(C4-C9 heteroaryl), —(CO—C4 alkyl)($C_6H_4$)$OR^7$, or —(CO)$R^8$; wherein $R^4$ and $R^5$, when present, are independently C1-C4 alkyl; $R^6$, when present, is hydrogen or C1-C4 alkyl; $R^7$, when present, is hydrogen or C1-C4 alkyl; and $R^8$, when present, is hydrogen, C1-C4 alkyl, C2-C4 alkenyl, C2-C4 haloalkyl, C2-C4 cyanoalkyl, C2-C4 hydroxyalkyl, C2-C4 haloalkoxy, C2-C4 alkoxy, C2-C9 alkylamino, C3-C8 cycloalkyl, C3-C8 cycloalkenyl, C3-C7 heterocyclyl, C3-C7 heterocycloalkenyl, C6-C10 aryl, or C4-C9 heteroaryl.

In a further aspect, disclosed is the use of a compound represented by Formula (II) in the manufacture of a medicament for the treatment, prevention, or delayed progression of nicotine dependence, a substance-use disorder (e.g., a stimulant-use disorder or an opioid-use disorder), obesity, metabolic syndrome, or a disorder responsive to inhibition of PTPRD activity:

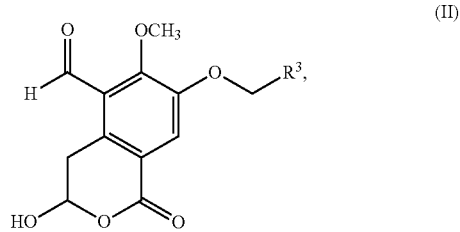

(II)

wherein R³ is hydrogen, C1-C4 alkyl, C2-C4 alkenyl, C2-C4 haloalkyl, C2-C4 alkoxy, —(C1-C4 alkyl)NR⁴R⁵, C3-C8 cycloalkyl, C3-C7 heterocyclyl, C6-C10 aryl, C4-C9 heteroaryl, —(C1-C4 alkyl)(C6-C10 aryl), —(C1-C4 alkyl)(C4-C9 heteroaryl), —(CO—C4 alkyl)(C₆H₄)OR⁷, or —(CO)R⁸;

wherein R⁴ and R⁵, when present, are independently C1-C4 alkyl;

R⁷, when present, is hydrogen or C1-C4 alkyl; and

R⁸, when present, is hydrogen, C1-C4 alkyl, C2-C4 haloalkyl, C2-C4 hydroxyalkyl, C2-C4 haloalkoxy, C2-C4 alkoxy, C3-C8 cycloalkyl, C3-C7 heterocyclyl, C3-C7 heterocycloalkenyl, C6-C10 aryl, or C4-C9 heteroaryl.

In a further aspect, disclosed is the use of a compound represented by Formula (II) in the manufacture of a medicament for the treatment, prevention, or delayed progression of nicotine dependence, a substance-use disorder (e.g., a stimulant-use disorder or an opioid-use disorder), obesity, metabolic syndrome, or a disorder responsive to inhibition of PTPRD activity, wherein R³ is C4-C5 cycloalkyl, C6 aryl, or C4-C5 heteroaryl.

In a further aspect, disclosed is the use of a compound represented by Formula (I) or Formula (II) in the manufacture of a medicament for the treatment, prevention, or delayed progression of nicotine dependence, a substance-use disorder (e.g., a stimulant-use disorder or an opioid-use disorder), obesity, metabolic syndrome, or a disorder responsive to inhibition of PTPRD activity, wherein R³ is hydrogen or has a structure represented by the formula:

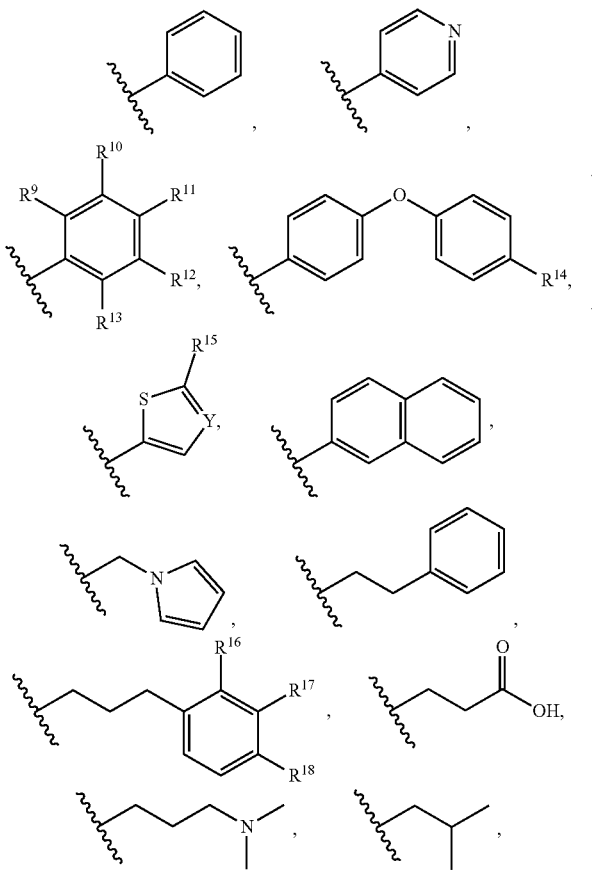

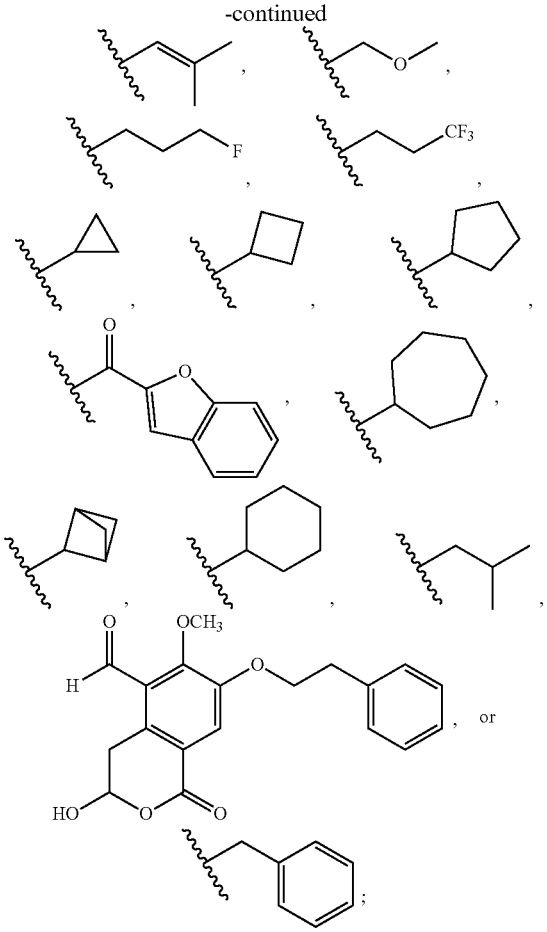

wherein R⁹-R¹³, when present, are independently hydrogen, methyl, —OCH₃, —CN, —CF₃, —OCF₃, or halide; R¹⁴, when present, is hydrogen or halide; R¹⁵, when present, is methyl or halide; Y, when present, is CH or N; and R¹⁶⁻¹⁸, when present, are independently hydrogen, hydroxyl, or halide.

In a further aspect, disclosed is the use of a compound represented by Formula (I) or Formula (II) in the manufacture of a medicament for the treatment, prevention, or delayed progression of nicotine dependence, a substance-use disorder (e.g., a stimulant-use disorder or an opioid-use disorder), obesity, metabolic syndrome, or a disorder responsive to inhibition of PTPRD activity, wherein R³ has a structure represented by the formula:

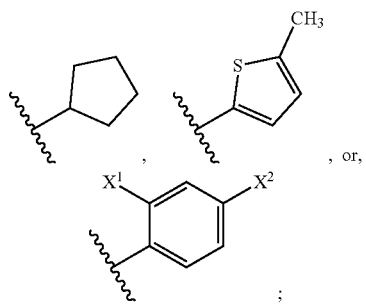

wherein X¹ and X², when present, are independently —Cl, —Br, —I, or —F.

In a further aspect, disclosed is the use of a compound represented by the following formula in the manufacture of a medicament for the treatment, prevention, or delayed progression of nicotine dependence, a substance-use disorder (e.g., a stimulant-use disorder or an opioid-use disorder), obesity, metabolic syndrome, or a disorder responsive to inhibition of PTPRD activity:

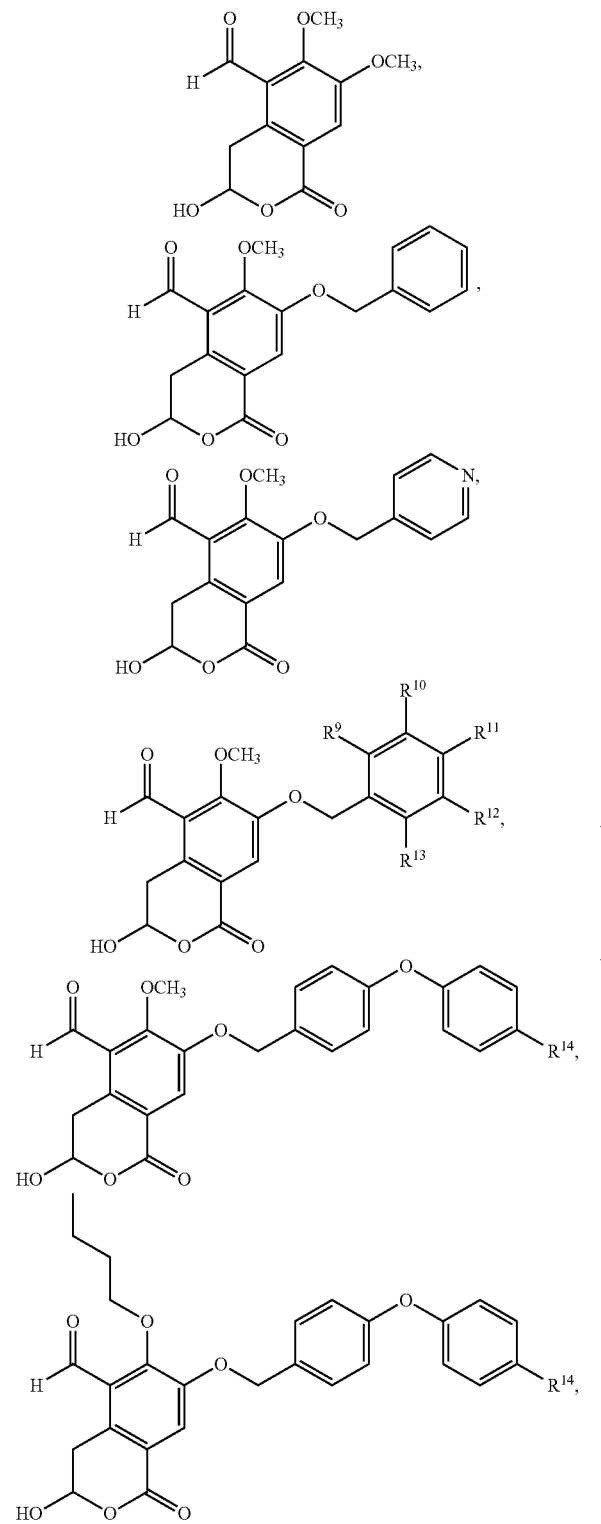

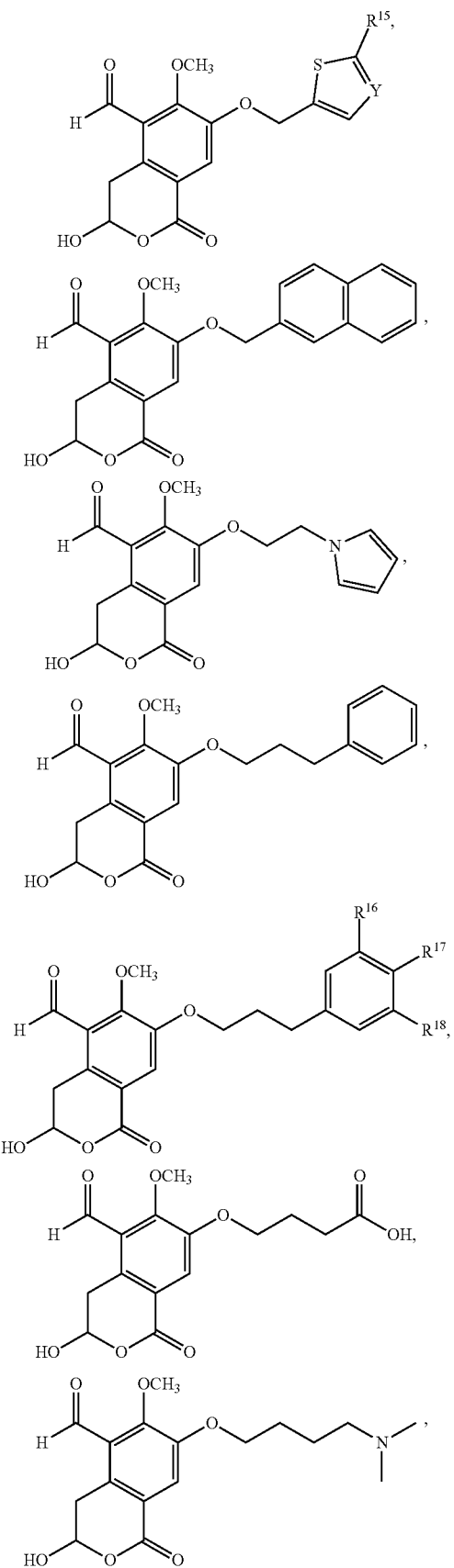

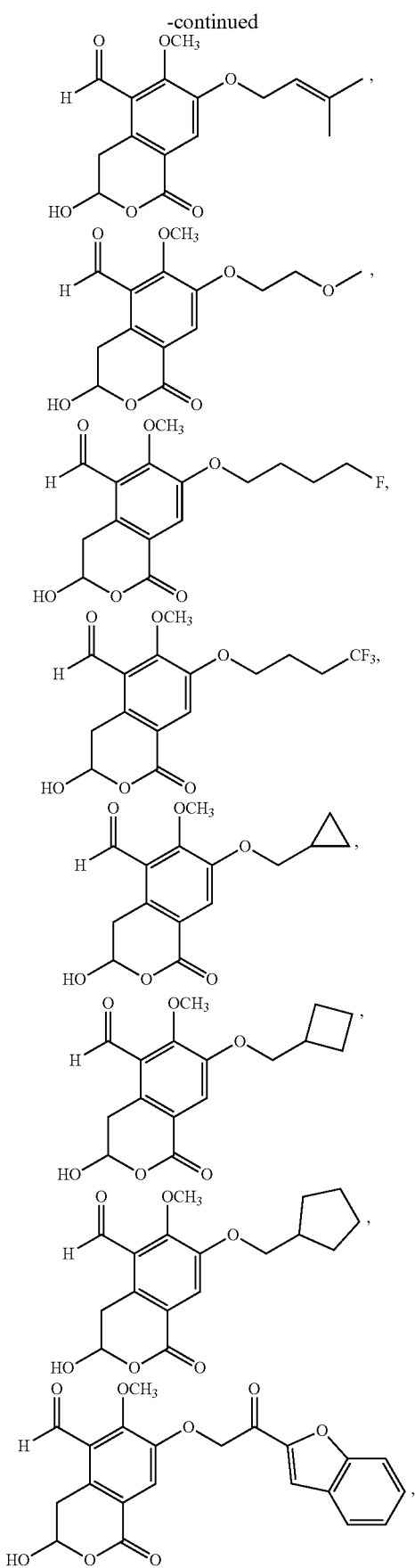

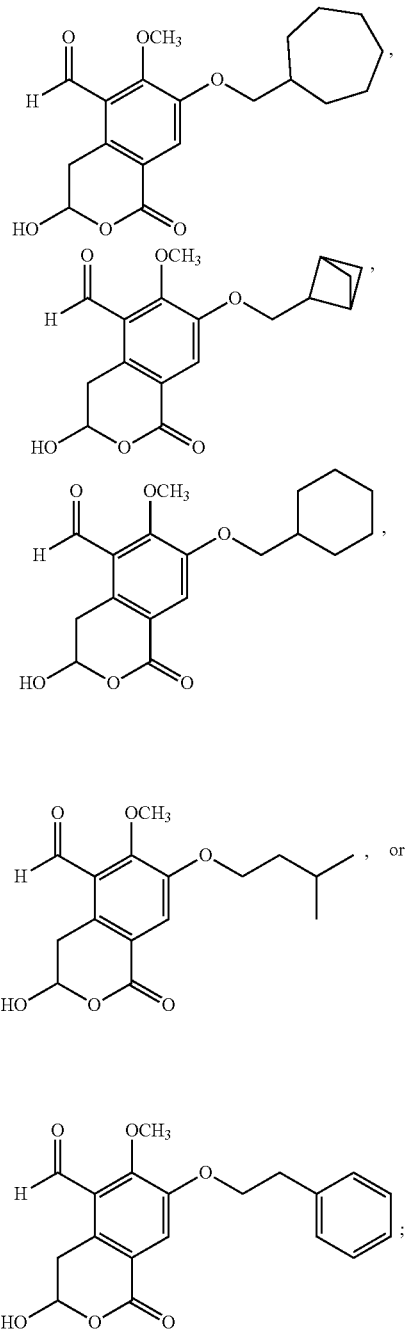

wherein $R^9$-$R^{13}$, when present, are independently hydrogen, methyl, —OCH$_3$, —CN, —CF$_3$, —OCF$_3$, or halide; $R^{14}$, when present, is hydrogen or halide; $R^{15}$, when present, is methyl or halide; Y, when present, is CH or N; and $R^{16-18}$, when present, are independently hydrogen, hydroxyl, or halide.

In a further aspect, disclosed is the use of a compound represented by the following formula in the manufacture of a medicament for the treatment, prevention, or delayed progression of nicotine dependence, a substance-use disorder (e.g., a stimulant-use disorder or an opioid-use disorder), obesity, metabolic syndrome, or a disorder responsive to inhibition of PTPRD activity:

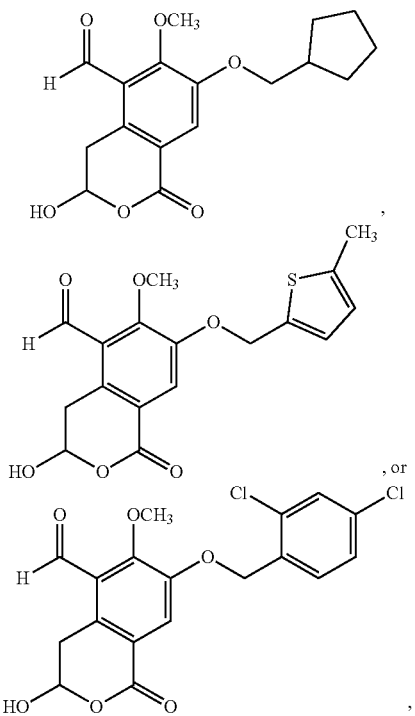

In a further aspect, disclosed is the use of a compound represented by the following formula in the manufacture of a medicament for the treatment, prevention, or delayed progression of nicotine dependence, a substance-use disorder (e.g., a stimulant-use disorder or an opioid-use disorder), obesity, metabolic syndrome, or a disorder responsive to inhibition of PTPRD activity:

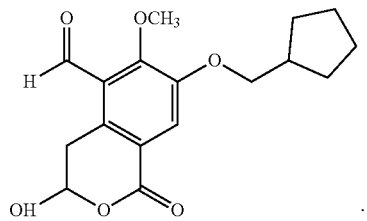 [SMILES: COc1c(OCC2CCCC2)cc2c(c1C=O)CC(O)OC2=O]

In some aspects, the manufacture of the medicament can further comprise copackaging or coformulating a disclosed compound with another therapeutic agent useful for treating nicotine dependence, a substance-use disorder, obesity, metabolic syndrome, or another disorder responsive to inhibition of PTPRD activity.

E. KITS

In a further aspect, disclosed is a kit comprising a compound represented by Formula (I) together with another therapeutic agent useful for treating nicotine dependence, a substance-use disorder, obesity, metabolic syndrome, or another disorder responsive to inhibition of PTPRD activity; and optionally, instructions for the use thereof for the treatment, prevention, or delayed progression of the disorder:

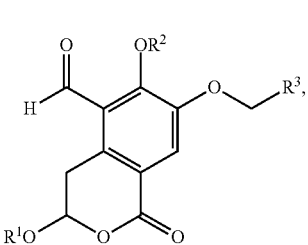

(I)

wherein $R^1$ is hydrogen, C1-C4 alkyl, C2-C4 alkenyl, C1-C4 haloalkyl, C1-C4 cyanoalkyl, C1-C4 hydroxyalkyl, C2-C4 alkoxy, C2-C4 haloalkoxy, C1-C4 alkylamino, C1-C4 acetyl, or (C1-C4)(C1-C4) dialkylamino;

$R^2$ is C1-C4 alkyl, C2-C4 alkenyl, C1-C4 haloalkyl, C1-C4 cyanoalkyl, C1-C4 hydroxyalkyl, C2-C4 alkoxy, C2-C4 haloalkoxy, C1-C4 alkylamino, or (C1-C4)(C1-C4) dialkylamino;

$R^3$ is hydrogen, C1-C9 alkyl, C2-C9 alkenyl, C2-C9 haloalkyl, C2-C9 cyanoalkyl, C2-C9 hydroxyalkyl, C2-C9 alkoxy, C2-C9 haloalkoxy, C2-C9 alkylamino, —(C1-C9 alkyl)$NR^4R^5$, C3-C8 cycloalkyl, C3-C8 cycloalkenyl, C3-C7 heterocyclyl, C3-C7 heterocycloalkenyl, C6-C10 aryl, C4-C9 heteroaryl, —(C1-C9 alkyl)(C3-C8 cycloalkyl), —(C1-C9 alkyl)(C3-C8 cycloalkenyl), —(C1-C9 alkyl)(C3-C7 heterocyclyl), —(C1-C9 alkyl)(C3-C7 heterocycloalkenyl), —(C1-C9 alkyl)(C6-C10 aryl), —(C1-C9 alkyl)(C4-C9 heteroaryl), —(C1-C9 alkyl)$COR^6$, —(C0-C9 alkyl)$(C_6H_4)OR^7$, or —(CO)$R^8$;

wherein $R^4$ and $R^5$, when present, are independently C1-C9 alkyl;

$R^6$, when present, is hydrogen, C1-C4 alkyl, C2-C4 alkenyl, C1-C4 haloalkyl, C1-C4 cyanoalkyl, C1-C4 hydroxyalkyl, C1-C4 alkoxy, C1-C4 haloalkoxy, C1-C4 alkylamino, C1-C4 aminoalkyl, or (C1-C4)(C1-C4) dialkylamino;

$R^7$, when present, is hydrogen, C1-C9 alkyl, C2-C9 alkenyl, C2-C9 haloalkyl, C2-C9 cyanoalkyl, C2-C9 hydroxyalkyl, C2-C9 haloalkoxy, C2-C9 alkoxy, C2-C9 alkylamino, C3-C8 cycloalkyl, C3-C8 cycloalkenyl, C3-C7 heterocyclyl, C3-C7 heterocycloalkenyl, C6-C10 aryl, or C4-C9 heteroaryl;

$R^8$, when present, is hydrogen, C1-C9 alkyl, C2-C9 alkenyl, C2-C9 haloalkyl, C2-C9 cyanoalkyl, C2-C9 hydroxyalkyl, C2-C9 haloalkoxy, C2-C9 alkoxy, C2-C9 alkylamino, C3-C8 cycloalkyl, C3-C8 cycloalkenyl, C3-C7 heterocyclyl, C3-C7 heterocycloalkenyl, C6-C10 aryl, or C4-C9 heteroaryl;

or a pharmaceutically-acceptable salt or prodrug thereof.

In a further aspect, disclosed is a kit comprising a compound represented by Formula (I) together with another therapeutic agent useful for treating nicotine dependence, a substance-use disorder, obesity, metabolic syndrome, or another disorder responsive to inhibition of PTPRD activity; and optionally, instructions for the use thereof for the treatment, prevention, or delayed progression of the disorder, wherein $R^1$ is hydrogen or C1-C2 alkyl; $R^2$ is C1-C2 alkyl; and $R^3$ is hydrogen, C1-C4 alkyl, C2-C4 alkenyl, C2-C4 haloalkyl, C2-C4 alkoxy, —(C1-C4 alkyl)$NR^4R^5$, —(C1-C4 alkyl)$COR^6$, C3-C8 cycloalkyl, C3-C7 heterocyclyl, C6-C10 aryl, C4-C9 heteroaryl, —(C1-C4 alkyl)(C6-C10 aryl), —(C1-C4 alkyl)(C4-C9 heteroaryl), —(CO—C4 alkyl)$(C_6H_4)OR^7$, or —(CO)$R^8$; wherein $R^4$ and $R^5$, when present, are independently C1-C4 alkyl; $R^6$, when present, is hydrogen or C1-C4 alkyl; $R^7$, when present, is hydrogen or C1-C4 alkyl; and $R^8$, when present, is hydrogen, C1-C4 alkyl, C2-C4 alkenyl, C2-C4 haloalkyl, C2-C4 cyanoalkyl, C2-C4 hydroxyalkyl, C2-C4 haloalkoxy, C2-C4 alkoxy, C2-C9 alkylamino, C3-C8 cycloalkyl, C3-C8 cycloalkenyl, C3-C7 heterocyclyl, C3-C7 heterocycloalkenyl, C6-C10 aryl, or C4-C9 heteroaryl.

In a further aspect, disclosed is a kit comprising a compound represented by Formula (II) together with another therapeutic agent useful for treating nicotine dependence, a substance-use disorder, obesity, metabolic syndrome, or another disorder responsive to inhibition of PTPRD activity; and optionally, instructions for the use thereof for the treatment, prevention, or delayed progression of the disorder:

(II)

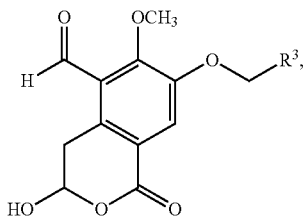

wherein $R^3$ is hydrogen, C1-C4 alkyl, C2-C4 alkenyl, C2-C4 haloalkyl, C2-C4 alkoxy, —(C1-C4 alkyl)$NR^4R^5$, C3-C8 cycloalkyl, C3-C7 heterocyclyl, C6-C10 aryl, C4-C9 heteroaryl, —(C1-C4 alkyl)(C6-C10 aryl), —(C1-C4 alkyl)(C4-C9 heteroaryl), —(CO—C4 alkyl)($C_6H_4$)$OR^7$, or —(CO)$R^8$;

wherein $R^4$ and $R^5$, when present, are independently C1-C4 alkyl;

$R^7$, when present, is hydrogen or C1-C4 alkyl; and $R^8$, when present, is hydrogen, C1-C4 alkyl, C2-C4 haloalkyl, C2-C4 hydroxyalkyl, C2-C4 haloalkoxy, C2-C4 alkoxy, C3-C8 cycloalkyl, C3-C7 heterocyclyl, C3-C7 heterocycloalkenyl, C6-C10 aryl, or C4-C9 heteroaryl.

In a further aspect, disclosed is a kit comprising a compound represented by Formula (II) together with another therapeutic agent useful for treating nicotine dependence, a substance-use disorder, obesity, metabolic syndrome, or another disorder responsive to inhibition of PTPRD activity; and optionally, instructions for the use thereof for the treatment, prevention, or delayed progression of the disorder, wherein $R^3$ is C4-C5 cycloalkyl, C6 aryl, or C4-C5 heteroaryl.

In a further aspect, disclosed is a kit comprising a compound represented by Formula (I) or Formula (II) together with another therapeutic agent useful for treating nicotine dependence, a substance-use disorder, obesity, metabolic syndrome, or another disorder responsive to inhibition of PTPRD activity; and optionally, instructions for the use thereof for the treatment, prevention, or delayed progression of the disorder, wherein $R^3$ is hydrogen or has a structure represented by the formula:

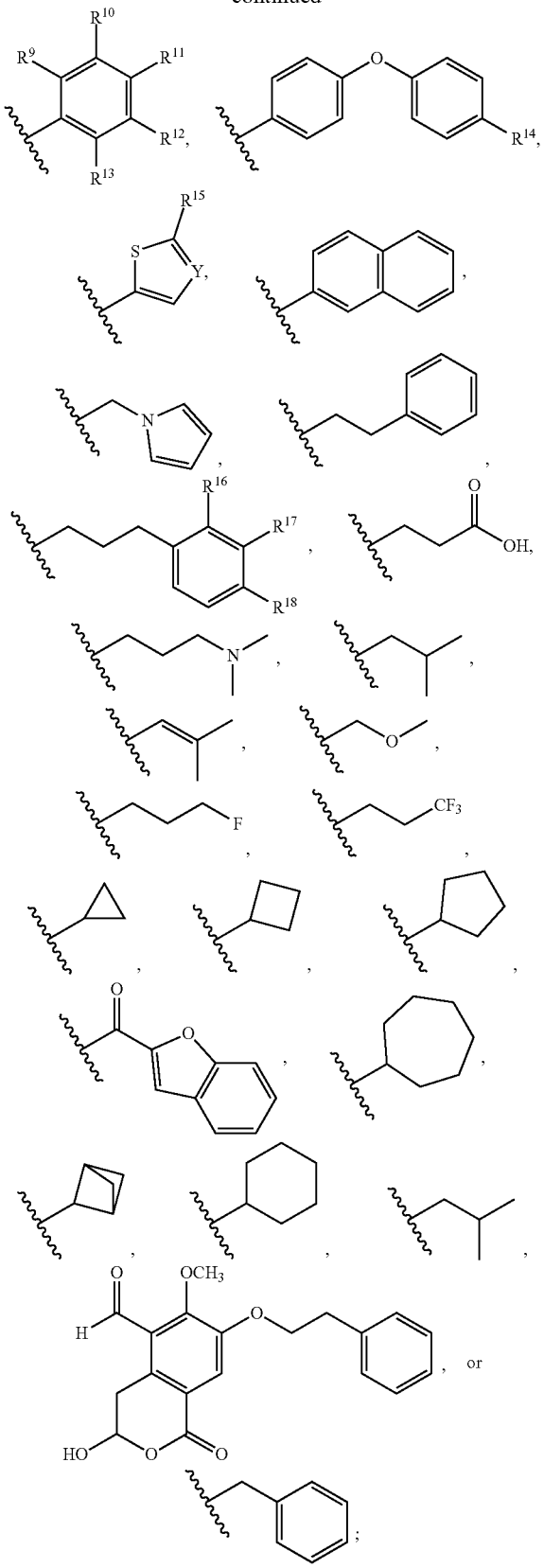

wherein $R^9$-$R^{13}$, when present, are independently hydrogen, methyl, —$OCH_3$, —CN, —$CF_3$, —$OCF_3$, or halide; $R^{14}$, when present, is hydrogen or halide; $R^{15}$, when present, is methyl or halide; Y, when present, is CH or N; and $R^{16-18}$, when present, are independently hydrogen, hydroxyl, or halide.

In a further aspect, disclosed is a kit comprising a compound represented by Formula (I) or Formula (II) together with another therapeutic agent useful for treating nicotine dependence, a substance-use disorder, obesity, metabolic syndrome, or another disorder responsive to inhibition of PTPRD activity; and optionally, instructions for the use thereof for the treatment, prevention, or delayed progression of the disorder, wherein $R^3$ has a structure represented by the formula:

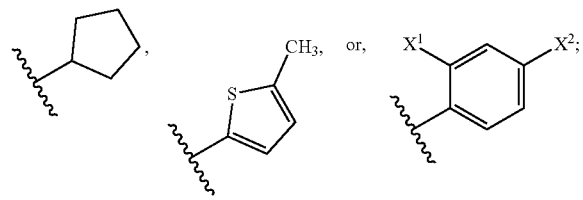

wherein $X^1$ and $X^2$, when present, are independently —Cl, —Br, —I, or —F.

In a further aspect, disclosed is a kit comprising a compound represented by the following formula together with another therapeutic agent useful for treating nicotine dependence, a substance-use disorder, obesity, metabolic syndrome, or another disorder responsive to inhibition of PTPRD activity; and optionally, instructions for the use thereof for the treatment, prevention, or delayed progression of the disorder:

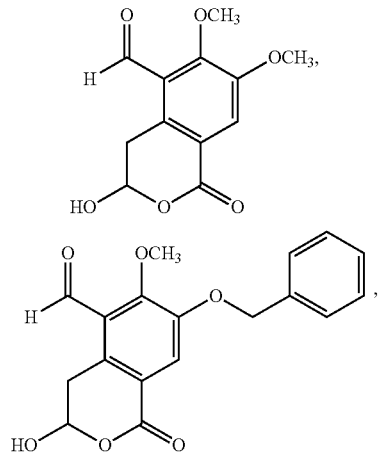

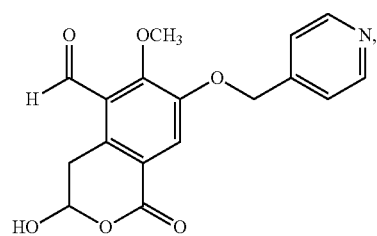

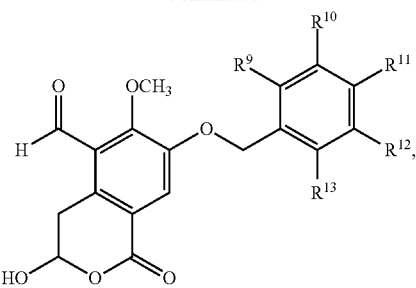

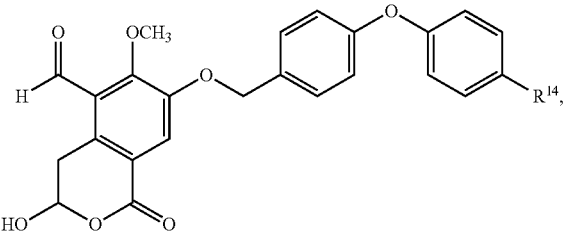

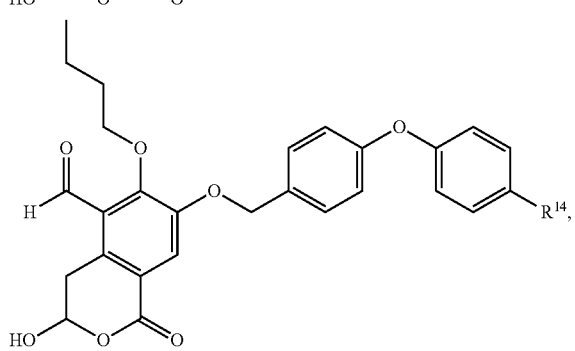

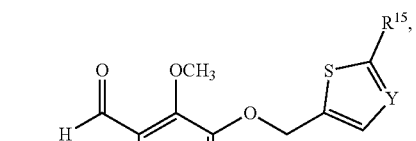

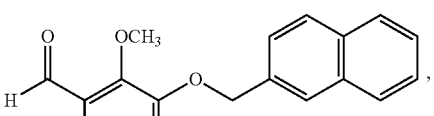

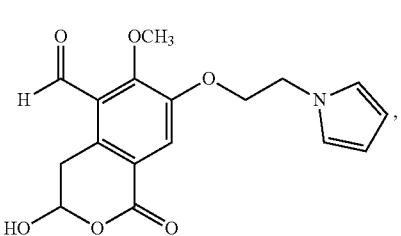

111
-continued
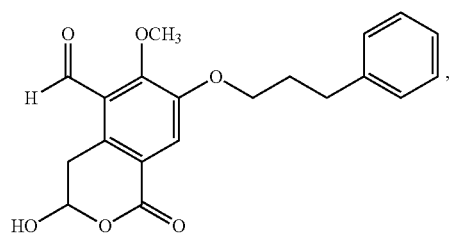
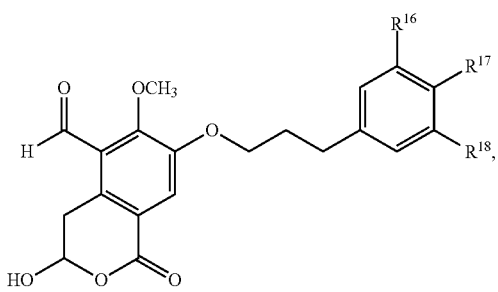
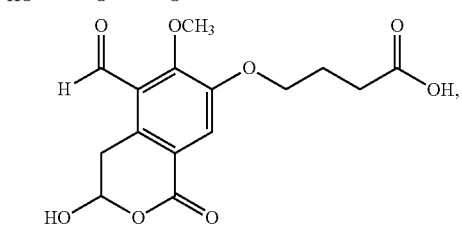
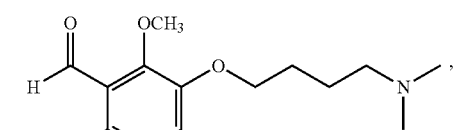
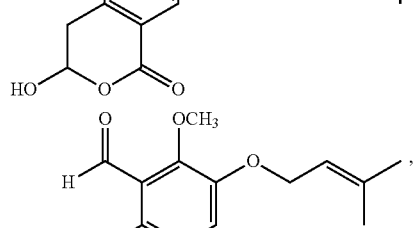
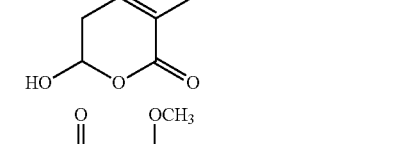
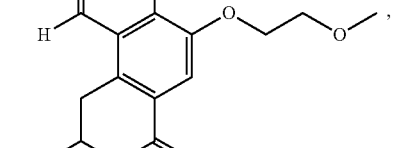
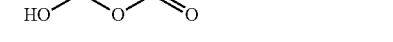
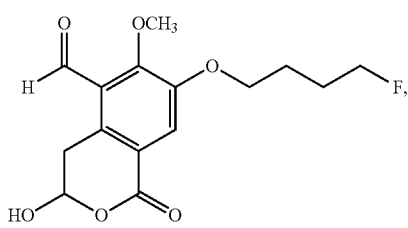
112
-continued
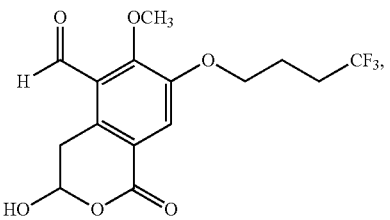
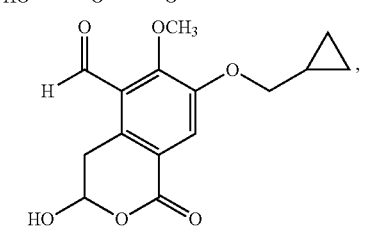
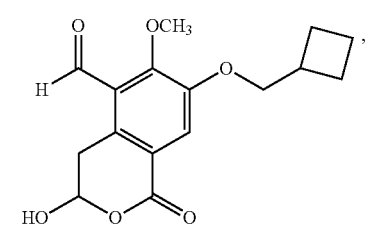
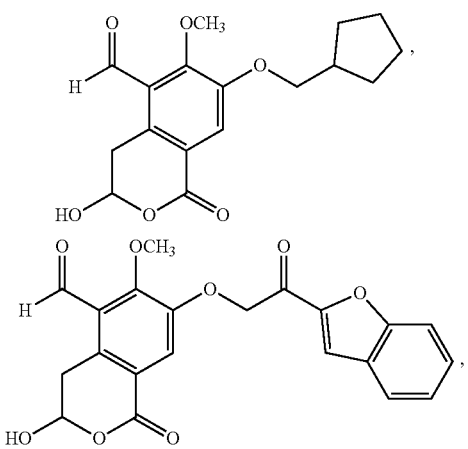
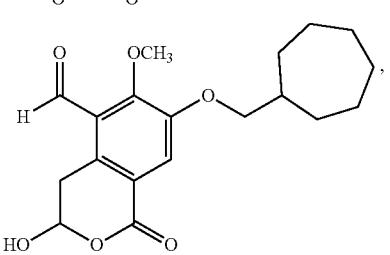
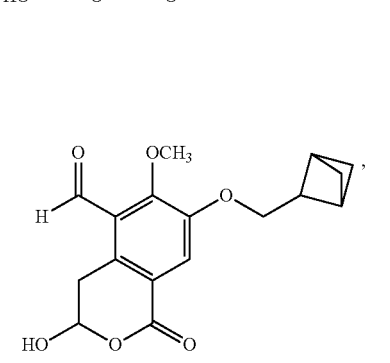

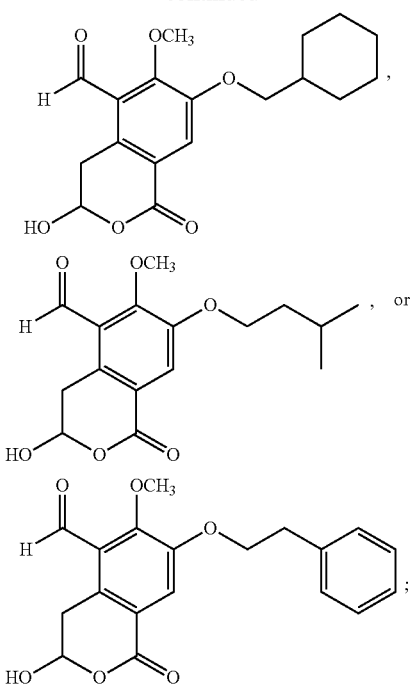

wherein $R^9$-$R^{13}$, when present, are independently hydrogen, methyl, —OCH$_3$, —CN, —CF$_3$, —OCF$_3$, or halide; $R^{14}$, when present, is hydrogen or halide; $R^{15}$, when present, is methyl or halide; Y, when present, is CH or N; and $R^{16-18}$, when present, are independently hydrogen, hydroxyl, or halide.

In a further aspect, disclosed is a kit comprising a compound represented by the following formula together with another therapeutic agent useful for treating nicotine dependence, a substance-use disorder, obesity, metabolic syndrome, or another disorder responsive to inhibition of PTPRD activity; and optionally, instructions for the use thereof for the treatment, prevention, or delayed progression of the disorder:

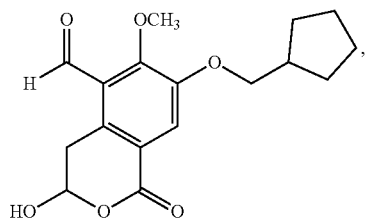 [SMILES: COc1c(OCC2CCCC2)cc2c(c1C=O)CC(O)OC2=O]

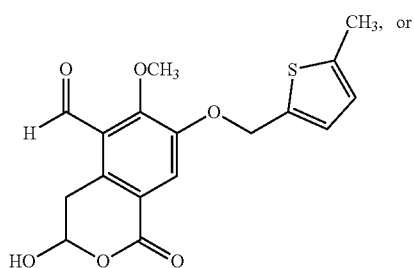

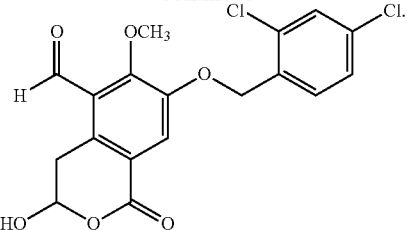

In a further aspect, disclosed is a kit comprising a compound represented by the following formula together with another therapeutic agent useful for treating nicotine dependence, a substance-use disorder, obesity, metabolic syndrome, or another disorder responsive to inhibition of PTPRD activity; and optionally, instructions for the use thereof for the treatment, prevention, or delayed progression of the disorder:

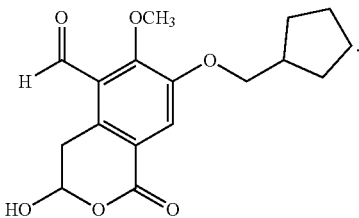

In some aspects, the kit can comprise a disclosed compound together with an opioid prescribed for the treatment of acute or chronic pain. In a further aspect, the kit can comprise a disclosed compound together with a stimulant prescribed for a variety disorders, including for example ADHD, ADD, narcolepsy, among others.

In a further aspect, the kit can comprise a disclosed compound together with a compound used for treating, preventing, or delaying the progression of nicotine dependence, a substance-use disorder, obesity, metabolic syndrome, or another disorder responsive to inhibition of PTPRD activity. Non limiting examples, such as in the case of opioid-use disorders, including certain opioid agonists such as buprenorphine or methadone.

Similarly, in some aspects, when the subject has a nicotine dependence, the subject may have also been prescribed a nicotine withdrawal aid and taking that withdrawal aid concurrently with the administration of a disclosed compound. Such a withdrawal aid can be present together in a kit with a disclosed compound. In some aspects, the kit comprises a disclosed compound and another therapeutic or other agent that is co-packaged and/or coformulated. In other aspects, the disclosed compound and another therapeutic or other agent are not copackaged or coformulated.

F. EXAMPLES

The following examples are put forth so as to provide those of ordinary skill in the art with a complete disclosure and description of how the methods and products claimed herein are made and evaluated, and are intended to be purely exemplary and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. The Examples are provided herein to illustrate the invention, and should not be construed as limiting the invention in any way.

1. Synthesis

Exemplary compounds were prepared according to Scheme 3:

Structures of Compounds 26-56:

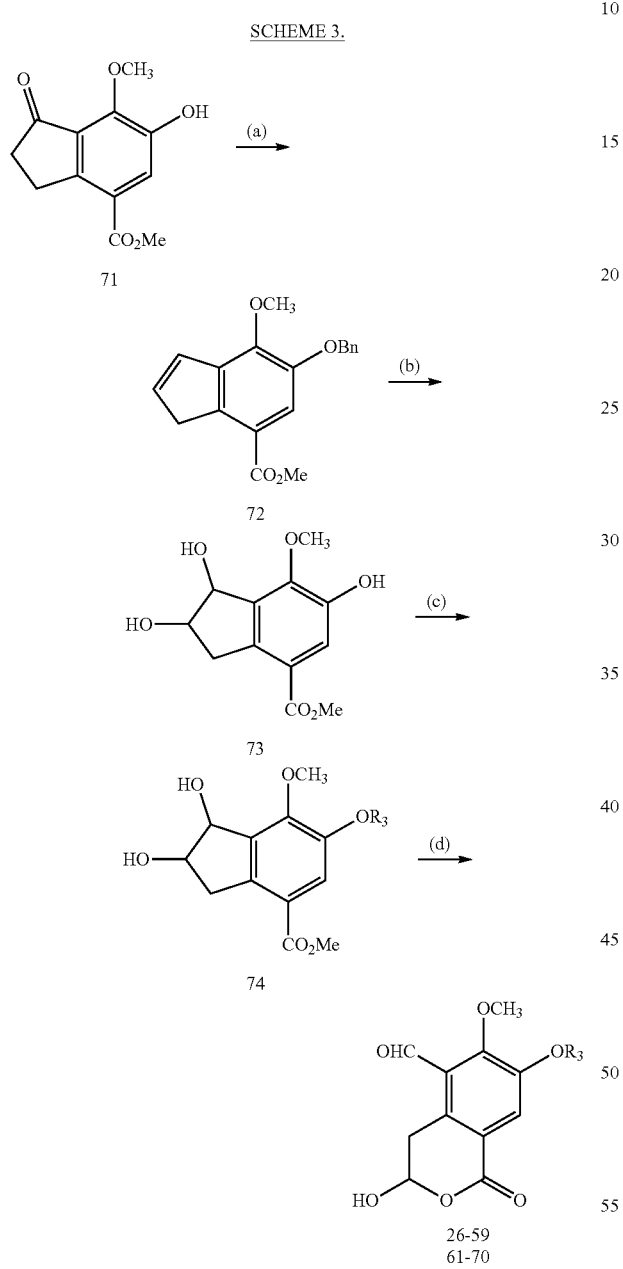

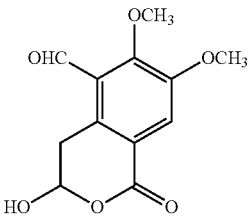

26

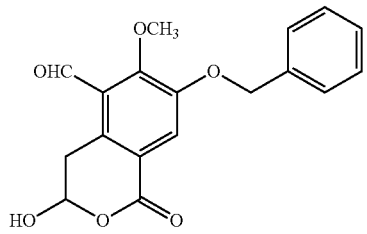

27

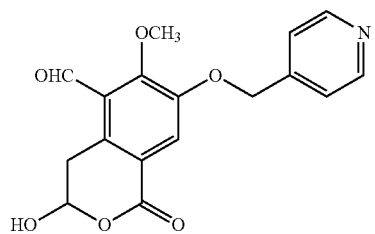

28

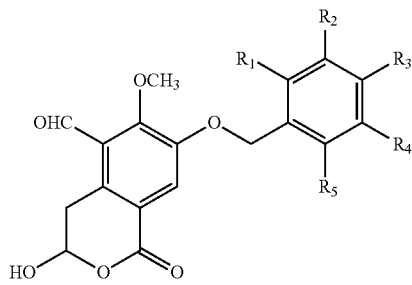

29-42

29: $R_1 = H$; $R_2 = H$; $R_3 = CH_3$; $R_4 = H$; $R_5 = H$
30: $R_1 = H$; $R_2 = H$; $R_3 = OCH_3$; $R_4 = H$; $R_5 = H$
31: $R_1 = H$; $R_2 = OCH_3$; $R_3 = H$; $R_4 = H$; $R_5 = H$
32: $R_1 = OCH_3$; $R_2 = H$; $R_3 = H$; $R_4 = H$; $R_5 = H$
33: $R_1 = H$; $R_2 = H$; $R_3 = CN$; $R_4 = H$; $R_5 = H$
34: $R_1 = H$; $R_2 = H$; $R_3 = CF_3$; $R_4 = H$; $R_5 = H$
35: $R_1 = H$; $R_2 = H$; $R_3 = OCF_3$; $R_4 = H$; $R_5 = H$
36: $R_1 = H$; $R_2 = H$; $R_3 = F$; $R_4 = H$; $R_5 = H$
37: $R_1 = H$; $R_2 = H$; $R_3 = I$; $R_4 = H$; $R_5 = H$
38: $R_1 = H$; $R_2 = H$; $R_3 = Cl$; $R_4 = H$; $R_5 = H$
39: $R_1 = H$; $R_2 = H$; $R_3 = Br$; $R_4 = H$; $R_5 = H$
40: $R_1 = Cl$; $R_2 = H$; $R_3 = Cl$; $R_4 = H$; $R_5 = H$
41: $R_1 = H$; $R_2 = Cl$; $R_3 = Cl$; $R_4 = H$; $R_5 = H$
42: $R_1 = Cl$; $R_2 = H$; $R_3 = Cl$; $R_4 = H$; $R_5 = Cl$

Reagents and conditions: (a) (i) BnBr, $K_2CO_3$, $CH_3CN$, reflux; (ii) $NaBH_4$, THF, MeOH; (iii) TsOH—$H_2O$, PhMe, 80° C.; (b) (i) AD-mix-α, $CH_3SO_2NH_2$, $H_2O$, t-BuOH; (ii) $H_2$, MeOH, Pd/C; (c) appropriate halide, $CH_3CN$, $K_2CO_3$, reflux; (d) (i) NaOH (2 mol/L), MeOH, THF; (ii) $NaIO_4$, t-BuOH, $H_2O$; (e) $PhNTf_2$, $Net_3$, $CH_2Cl_2$; trans-1-penten-1-ylboronic acid pinacol ester, $Pd(PPh_3)_4$, $Na_2CO_3$, $H_2O$, Toluene; (g) (i) 2N KOH, MeOH; (ii) $NaIO_4$, t-BuOH, $H_2O$.

-continued
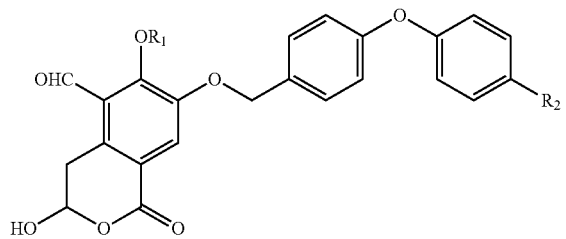
43: $R_1 = CH_3$; $R_2 = H$
44: $R_1 = CH_3$; $R_2 = F$
45: $R_1 = n\text{-}C_4H_9$; $R_2 = H$
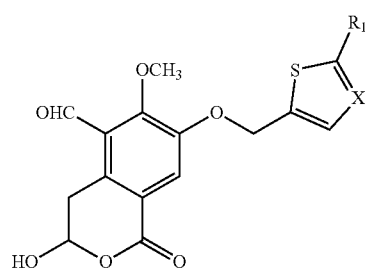
46: $R_1 = CH_3$; $X = CH$
47: $R_1 = CH_2CH_3$; $X = CH$
48: $R_1 = Cl$; $X = N$
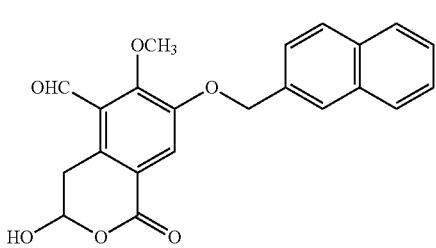
49
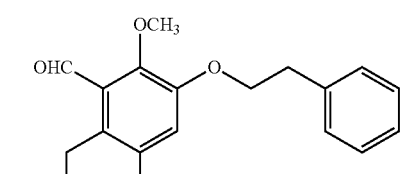
50
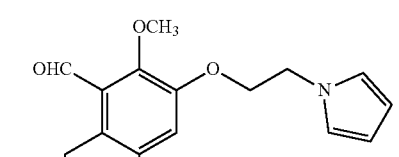
51
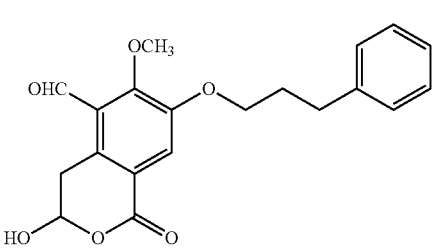
52
-continued
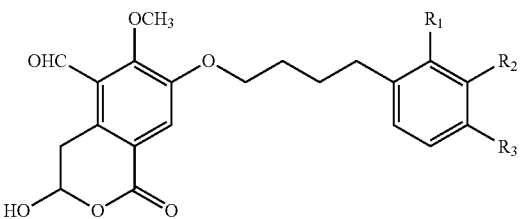
53: $R_1 = H$; $R_2 = H$; $R_3 = Cl$
54: $R_1 = H$; $R_2 = H$; $R_3 = F$
55: $R_1 = OH$; $R_2 = H$; $R_3 = OH$
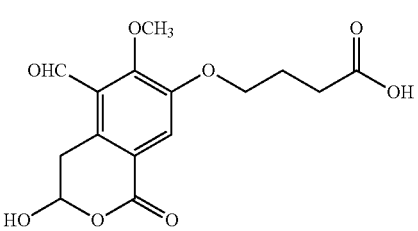
56
Structures of Compounds 57-70:
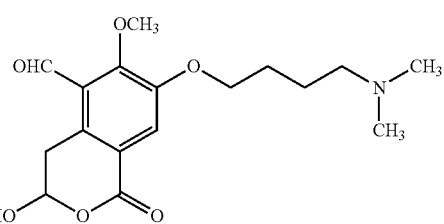
57
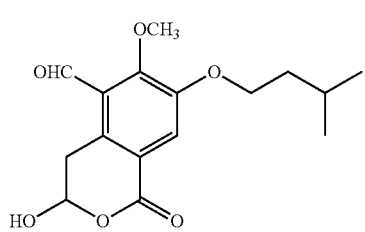
58
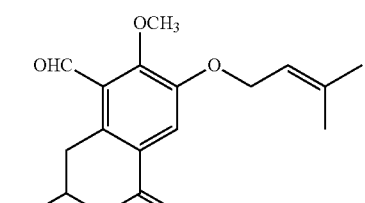
59
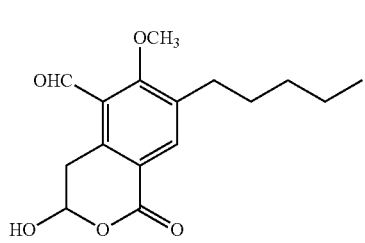
60

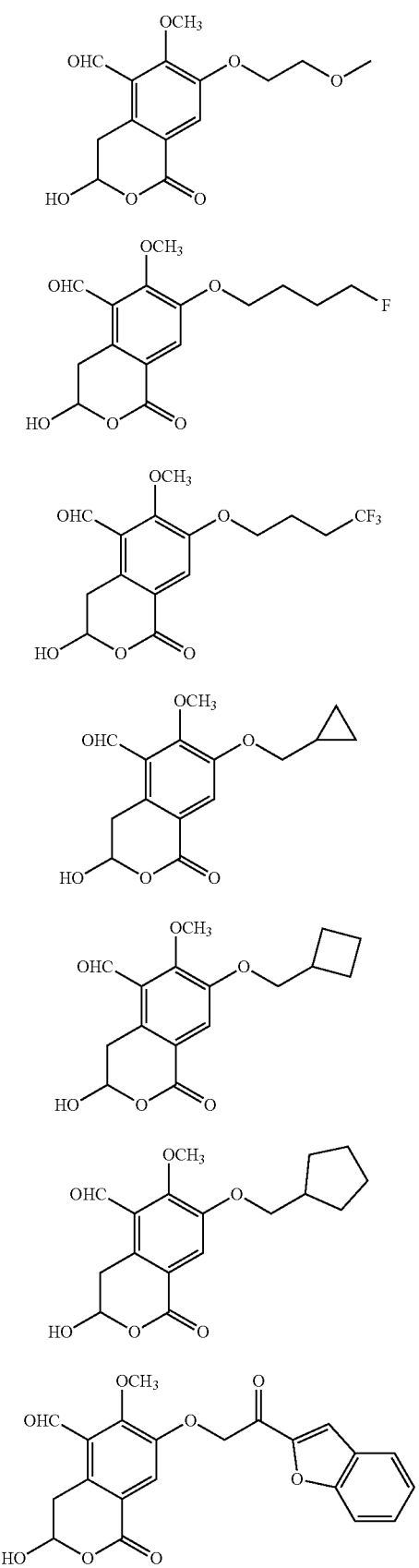

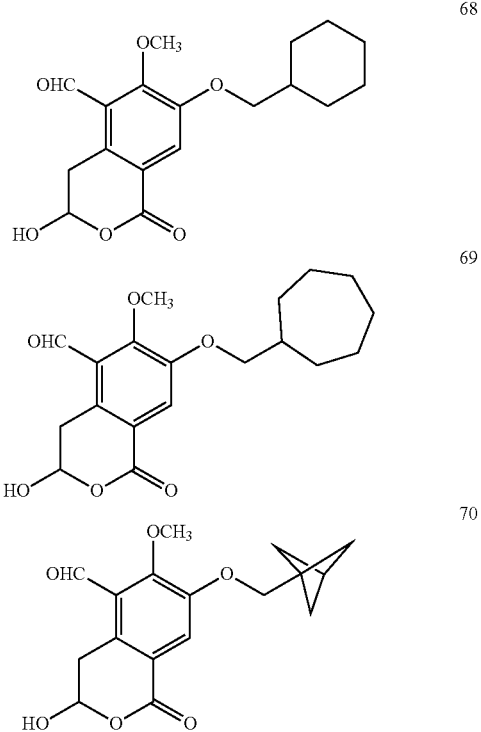

Analogues 26-70 were prepared from commercially available indanone 71 (Scheme 1). Treatment of indanone 71 with benzyl bromide under basic conditions followed by reduction with sodium borohydride to give the corresponding alcohol and dehydration in the presence of p-toluenesulfonic acid gave alkene 72. Dihydroxylation of the olefin with AD-mix-α in the presence of methanesulfonamide followed by hydrogenolysis gave triol 73. See Ling, Q.; Huang, Y.; Zhou, Y.; Cai, Z.; Xiong, B.; Zhang, Y.; Ma, L.; Wang, X.; Li, X.; Li, J.; Shen, J., Illudalic acid as a potential LAR inhibitor: synthesis, SAR, and preliminary studies on the mechanism of action. *Bioorg Med Chem* 2008, 16 (15), 7399-409. Alkylation of 73 with the appropriate halide under basic conditions gave ethers of general structure 74. Saponification of 74 followed by oxidation with sodium periodate (NaIO$_4$) gave lactols 26-59 and 61-70. Treatment of triol 73 with phenyl triflimide (PhNTf$_2$) gave triflate 75 which was then treated with trans-1-penten-1-ylboronic acid pinacol ester in presence of palladium tetrakis to afford alkene 76. Saponification, metal catalyzed hydrogenation, and oxidation with NaIO$_4$ provided the pentyl analogue 60.

All reagents and solvents were purchased from commercial sources and used without further purification. All reactions in nonaqueous solvents were conducted in flame-dried glassware under a positive pressure of argon and with magnetic stirring. All NMR spectra were obtained at 400 MHz for $^1$H, 100 MHz for $^{13}$C with internal standards of (CH$_3$)$_4$Si ($^1$H, 0.00), CHCl$_3$ ($^1$H, 7.27; $^{13}$C, 77.2 ppm), and MeOH ($^1$H, 3.34; $^{13}$C, 49.86) for non-aqueous samples or H$_2$O ($^1$H, 4.80) unless mentioned otherwise. Elemental analyses were obtained from the Atlantic Microlab Inc., GA and are within 0.4%. Silica gel (60 Å, 0.040-0.063 mm) was used for flash chromatography in an ISCO combi-flash instrument. The purity of all final compounds was determined to be >95% by analytical high-performance liquid chromatography (HPLC) analysis or combustion analysis.

6-Benzyloxy-7-methoxy-3H-indene-4-carboxylic acid methyl ester (72). A mixture of 6-hydroxy-7-methoxy-1-oxo-indan-4-carboxylic acid methyl ester (5.00 g, 21.2 mmol) and $K_2CO_3$ (4.40 g, 32 mmol) in DMF (80 mL) was stirred for 30 minutes at room temperature. Benzyl bromide (4.4 g, 25.5 mmol) was added and the combined mixture was stirred for 14 h at room temperature. The mixture was poured into $H_2O$ (50 mL) and extracted with EtOAc (100 mL). The organic layer was collected, washed with $H_2O$ (2×50 mL) and brine (30 mL), dried ($Na_2SO_4$), and concentrated under reduced pressure. The resulting solid was dissolved in MeOH (100 mL), cooled to 0° C., and treated with $NaBH_4$ (1.09 g, 29 mmol). The reaction mixture was allowed to reach room temperature and stirred for 2 h. After removal of the solvent, 2N aqueous HCl (50 mL) was added slowly. This aqueous layer was then extracted with EtOAc (3×80 mL). The combined extract was dried ($Na_2SO_4$) and evaporated to dryness under reduced pressure. Anhydrous toluene (10 mL) was then added to the resulting solid and removed under reduced pressure 3 times. The solid was dissolved in toluene (100 mL) followed by the addition of TsOH·$H_2O$ (0.217 g, 1.25 mmol). The reaction mixture was stirred for 4 h at 85° C., cooled to room temperature, diluted with EtOAc (100 mL), and washed with $H_2O$ (50 mL) and brine (30 mL). The organic layer was dried over $Na_2SO_4$, evaporated to dryness under reduced pressure, and subjected to flash column chromatography (10% EtOAc in hexane) to afford 72 (6.100 g, 78% over 3 steps): $^1H$ NMR (400 MHz, $CDCl_3$) δ 7.53 (s, 1H), 7.48-7.32 (m, 5H), 7.01 (m, 1H), 6.58 (m, 1H), 5.15 (s, 2H), 3.99 (s, 3H), 3.90 (s, 3H), 3.69 (m, 2H); $^{13}C$ NMR (100 MHz, $CDCl_3$) 166.9, 149.9, 146.8, 140.8, 138.8, 136.9, 135.5, 128.5, 128.0, 127.5, 127.5, 120.5, 113.0, 71.5, 61.2, 51.8, 41.0.

1,2,6-Trihydroxy-7-methoxy-indan-4-carboxylic acid methyl ester (73). A 250 mL flask was charged with AD-mix-α (28 g), $H_2O$ (45 mL), and t-BuOH (45 mL). The mixture was cooled to 0° C. followed by the addition of methanesulfonamide (2.00 g, 21 mmol) and 71 (5.70 g, 18.4 mmol). The reaction mixture was warmed to room temperature and stirred for 16 h. Upon disappearance of the starting material, sodium sulfite (29.50 g) was added and the reaction mixture was stirred for additional 30 minutes. The mixture was diluted by the addition of $H_2O$ (50 mL) and EtOAc (100 mL). The organic layer was collected, and the aqueous layer was extracted with EtOAc (3×100 mL). The combined organic layers were washed with 2N KOH (40 mL) and brine (50 mL), dried ($Na_2SO_4$), and concentrated under reduced pressure. The resulting solid was dissolved in MeOH (100 mL), charged with Pd/C (5% Pd on charcoal, 1.00 g) and a magnetic stirrer. A balloon filled with $H_2$ gas was connected to the reaction flask through a rubber septum and vigorously stirred for 14 h. The mixture was filtered through a pad of celite and concentrated under reduced pressure. The residue was then subjected to a column chromatography using EtOAc as the eluent to afford 73 (4.20 g, 81% overall 2 steps): $^1H$ NMR (400 MHz, $CD_3OD$) δ 7.39 (s, 1H), 5.00 (d, J=8.0 Hz, 1H), 4.26-4.21 (m, 1H), 3.99 (s, 3H), 3.81 (s, 3H), 3.41-3.34 (m, 1H), 3.04-2.98 (m, 1H); $^{13}C$ NMR (100 MHz, $CD_3OD$) 166.9, 149.3, 147.9, 136.2, 134.8, 121.1, 118.5, 72.8, 71.6, 59.9, 50.8, 37.9.

6-Cyclopentylmethoxy-1,2-dihydroxy-7-methoxy-indan-4-carboxylic acid methyl ester (74). A mixture of 73 (0.300 g, 1.2 mmol) and $K_2CO_3$ (0.196 g, 1.30 mmol) in DMF (10 mL) was stirred for 30 minutes. (Bromomethyl)cyclopentane (0.212 g, 1.30 mmol) was added and the reaction was heated at 80° C. for 6 h. The reaction mixture was then partitioned between EtOAc (30 mL) and $H_2O$ (15 mL). The organic layer was collected and the aqueous layer was extracted with EtOAc (2×20 mL). The combined organic extracts were washed with brine (15 mL), dried ($Na_2SO_4$), and concentrated under reduced pressure. The resulting material was subjected to a flash chromatography using hexane:EtOAc (1:1) as eluent to afford 74 (0.320 g, 81%): $^1H$ NMR (400 MHz, $CDCl_3$) δ 7.47 (s, 1H), 5.13 (m, 1H), 4.42 (m, 1H), 4.01 (s, 3H), 3.85-3.83 (m, 5H), 3.35-3.19 (m, 3H), 1.37 (m, 1H), 1.85 (d, J=4.0 Hz, 1H), 1.84-1.82 (m, 2H), 1.63-1.58 (m, 4H), 1.37-1.33 (m, 2H).

7-Cyclopentylmethoxy-3-hydroxy-6-methoxy-1-oxo-isochroman-5-carbaldehyde (66). A mixture of 74 (0.600 g, 1.8 mmol), methanolic 2N KOH (3 mL) was stirred at 75° C. for 2 h. After removal of the solvent under reduced pressure, aqueous 2N HCl was added until the pH lowered to 1-2. The aqueous mixture was then extracted with EtOAc (5×15 mL). The combined organic extracts were dried ($Na_2SO_4$) and concentrated under reduced pressure. The solid obtained (0.500 g) was dissolved in 50% aqueous solution of dioxane (5 mL), treated with $NaIO_4$ (0.500 g, 2.3 mmol) and the mixture was stirred at room temperature for 2.5 h. The mixture was partitioned between EtOAc (10 mL) and $H_2O$ (5 mL) and organic layer was collected. The aqueous layer was extracted with EtOAc (5×20 mL). The combined organic extracts were washed with brine (15 mL), dried ($Na_2SO_4$), and evaporated to dryness under reduced pressure. $CH_2Cl_2$ (5 mL) was added to the residue and the mixture was filtered. The $CH_2Cl_2$ solution was concentrated under reduced pressure, and the solid obtained was washed with dry $Et_2O$:hexane (1:1, 2×3 mL) to afford 66 (0.340 g, 68% over 2 steps): $^1H$ NMR (400 MHz, $CDCl_3$) δ 10.51 (s, 1H), 7.84 (s, 1H), 5.89 (m, 1H), 4.09 (s, 3H), 3.99-3.94 (m, 3H), 3.64-3.44 (m, 2H), 2.45-2.42 (m, 1H), 1.89-1.85 (m, 2H), 1.68-1.57 (m, 4H), 1.39-1.34 (m, 2H); $^{13}C$ NMR (100 MHz, $CDCl_3$) δ 191.8, 164.5, 158.3, 151.2, 130.4, 126.9, 120.4, 118.5, 95.5, 73.4, 62.2, 38.9, 30.7, 29.6, 25.4; Elemental analysis calcd (%) for $C_{17}H_{20}O_6$: C, 63.74, H, 6.29; found: C, 63.49, H, 6.37.

The following compounds were synthesized by a route similar to that described for 66: 27, 29, 31, 39, 40, 42, 43, 44, 46, 49, 50, 51, 52, 53, 55, 58, 59, 63, 64, 65, 68, and 69.

7-(Benzyloxy)-3-hydroxy-6-methoxy-1-oxoisochromane-5-carbaldehyde (27). $^1H$ NMR (400 MHz, DMSO-$d_6$) δ 10.37 (s, 1H), 7.86 (s, 1H), 7.74 (d, J=5.5 Hz, 1H), 7.51-7.44 (m, 2H), 7.40 (t, J=7.6 Hz, 2H), 7.36-7.29 (m, 1H), 5.74 (q, J=4.6 Hz, 1H), 5.27 (s, 2H), 3.99 (s, 3H), 3.38-3.31 (m, 1H), 3.27-3.22 (m, 1H); $^{13}C$ NMR (100 MHz, DMSO-$d_6$) δ 192.35, 163.60, 157.60, 150.66, 136.74, 131.34, 129.02, 128.55, 128.11, 127.58, 121.47, 119.11, 95.76, 70.81, 62.50, 31.51; HRMS (ESI): $C_{18}H_{17}O_6^+$ (M+H): 329.1020, found: 329.1021.

3-Hydroxy-6-methoxy-7-((4-methylbenzyl)oxy)-1-oxoisochromane-5-carbaldehyde (29). $^1H$ NMR (400 MHz, $CDCl_3$) δ 10.51 (s, 1H), 7.96 (s, 1H), 7.33 (d, J=7.6 Hz, 2H), 7.20 (d, J=7.6 Hz, 2H), 5.90 (t, J=3.8 Hz, 1H), 5.13 (s, 2H), 4.52 (br s, 1H), 4.06 (s, 3H), 3.67-3.57 (m, 1H), 3.52-3.43 (m, 1H), 2.36 (s, 3H); $^{13}C$ NMR (100 MHz, $CDCl_3$) δ 191.70, 163.91, 158.55, 150.75, 138.34, 132.50, 130.77, 129.42, 127.77, 127.08, 120.51, 119.31, 95.31, 71.21, 62.30, 30.72, 21.21; HRMS (ESI): $C_{19}H_{18}O_6Na^+$ (M+Na): 365.0996, found: 365.0998.

3-Hydroxy-6-methoxy-7-((3-methoxybenzyl)oxy)-1-oxoisochromane-5-carbaldehyde (31). $^1H$ NMR (400 MHz, Acetone-$d_6$) δ 10.49 (s, 1H), 7.97 (s, 1H), 7.52 (dd, J=7.6, 1.8 Hz, 1H), 7.35 (td, J=8.0, 1.8 Hz, 1H), 7.07 (d, J=8.4 Hz, 1H), 6.99 (t, J=7.4 Hz, 1H), 6.67 (d, J=6.8 Hz, 1H), 5.88-5.82 (m, 1H), 5.29 (s, 2H), 4.09 (s, 3H), 3.90 (s, 3H), 3.46-3.41 (m, 2H); $^{13}$C NMR (100 MHz, Acetone-d$_6$) δ 191.37, 162.81, 157.87, 157.48, 150.78, 130.78, 129.76, 129.39, 127.34, 124.24, 121.53, 120.44, 118.87, 110.71, 95.26, 65.99, 61.62, 55.01, 31.14; HRMS (ESI): C$_{19}$H$_{18}$O$_7$Na$^+$ (M+Na): 381.0945, found: 381.0945.

7-((4-Bromobenzyl)oxy)-3-hydroxy-6-methoxy-1-oxoisochromane-5-carbaldehyde (39). $^1$H NMR (400 MHz, CDCl$_3$) δ 10.51 (s, 1H), 7.92 (s, 1H), 7.53 (d, J=8.0 Hz, 2H), 7.32 (d, J=8.0 Hz, 2H), 5.90 (t, J=3.6 Hz, 1H), 5.12 (s, 2H), 4.60 (br s, 1H), 4.06 (s, 3H), 3.63 (dd, J=18.0, 3.6 Hz, 1H), 3.47 (dd, J=18.0, 3.6 Hz, 1H); $^{13}$C NMR (100 MHz, CDCl$_3$) δ 191.54, 163.89, 158.47, 150.51, 134.52, 131.95, 131.16, 129.25, 127.24, 122.51, 120.63, 119.23, 95.32, 70.54, 62.38, 30.71; HRMS (ESI): C$_{18}$H$_{15}$$^{79}$BrO$_6$Na$^+$ (M+Na): 428.9944, found: 428.9948; C$_{18}$H$_{15}$$^{81}$BrO$_6$Na$^+$ (M+Na): 430.9924, found: 430.9926.

7-((2,4-Dichlorobenzyl)oxy)-3-hydroxy-6-methoxy-1-oxoisochromane-5-carbaldehyde (40). $^1$H NMR (400 MHz, Acetone-d$_6$) δ 10.50 (s, 1H), 7.96 (s, 1H), 7.79-7.73 (m, 1H), 7.62-7.57 (m, 1H), 7.51-7.47 (m, 1H), 5.88 (s, 1H), 5.39 (s, 2H), 5.29 (s, 1H), 4.10 (s, 3H), 3.48-3.44 (m, 2H); $^{13}$C NMR (100 MHz, Acetone-d$_6$) δ 191.25, 162.69, 157.68, 150.45, 142.91, 134.51, 133.11, 131.42, 131.12, 129.18, 127.63, 121.70, 118.85, 117.37, 101.33, 67.81, 61.93, 31.15; HRMS (ESI): C$_{15}$H$_{14}$$^{35}$Cl$_2$O$_6$Na$^+$ (M+Na): 419.0060, found: 419.0066; C$_{18}$H$_{14}$$^{35}$Cl$^{37}$ClO$_6$Na$^+$ (M+Na): 421.0030, found: 421.0035; C$_{18}$H$_{14}$$^{37}$Cl$_2$O$_6$Na$^+$ (M+Na): 423.0001, found: 423.0005.

3-Hydroxy-6-methoxy-1-oxo-7-((4-phenoxybenzyl)oxy)isochromane-5-carbaldehyde (43). $^1$H NMR (400 MHz, CDCl$_3$) δ 10.51 (s, 1H), 7.96 (s, 1H) 7.40 (d, J=8.0 Hz, 2H), 7.34 (t, J=7.8 Hz, 2H), 7.12 (t, J=7.4 Hz, 1H), 7.05-6.99 (m, 4H), 5.91 (t, J=3.8 Hz, 1H), 5.13 (s, 2H), 4.65 (br s, 1H), 4.07 (s, 3H), 3.67-3.59 (m, 1H), 3.52-3.43 (m, 1H); $^{13}$C NMR (100 MHz, CDCl$_3$) δ 191.65, 163.97, 158.55, 157.68, 156.66, 150.69, 130.95, 130.08, 129.82, 129.40, 127.16, 123.65, 120.58, 119.34, 119.24, 118.71, 95.34, 70.91, 62.34, 30.73; HRMS (ESI): C$_{24}$H$_{20}$O$_7$Na$^+$ (M+Na): 443.1101, found: 443.1100.

7-((4-(4-Fluorophenoxy)benzyl)oxy)-3-hydroxy-6-methoxy-1-oxoisochromane-5-carbaldehyde (44). $^1$H NMR (400 MHz, Acetone-d$_6$) δ 10.49 (s, 1H), 7.93 (s, 1H), 7.58 (d, J=8.4 Hz, 2H), 7.16 (t, J=8.4 Hz, 2H), 7.10-7.05 (m, 2H), 7.03 (d, J=8.4 Hz, 2H), 6.68 (d, J=5.6 Hz, 1H), 5.87 (q, J=4.5 Hz, 1H), 5.28 (s, 2H), 4.10 (s, 3H), 3.44 (d, J=4.1 Hz, 2H); $^{13}$C NMR (100 MHz, Acetone-d$_6$) δ 191.33, 162.80, 158.92 (d, $^1$JCF=238.9 Hz), 157.86, 157.82, 152.82 (d, $^4$JCF=2.3 Hz), 150.69, 131.27, 130.95, 129.78, 127.37, 121.51, 120.94 (d, $^3$JCH=8.4 Hz), 118.88, 118.03, 116.35 (d, $^2$JCF=23.2 Hz), 95.26, 70.41, 61.76, 31.13; $^{19}$F NMR (376 MHz, Acetone-d$_6$) δ−121.21--121.29 (m, 1F); HRMS (ESI): C$_{24}$H$_{19}$FO$_7$Na$^+$ (M+Na): 461.1007, found: 461.1013.

3-Hydroxy-6-methoxy-7-((5-methylthiophen-2-yl)methoxy)-1-oxoisochromane-5-carbaldehyde (46). $^1$H NMR (400 MHz, CDCl$_3$) δ 10.50 (s, 1H), 7.96 (s, 1H), 6.93 (d, J=3.6 Hz, 1H), 6.64 (d, J=3.6 Hz, 1H), 5.89 (t, J=3.8 Hz, 1H), 5.25 (s, 2H), 4.22 (s, 1H), 4.08 (s, 3H), 3.62 (dd, J=18.0, 3.8 Hz, 1H), 3.47 (dd, J=18.0, 3.8 Hz, 1H), 2.47 (s, 3H); $^{13}$C NMR (100 MHz, CDCl$_3$) δ 191.65, 163.66, 158.65, 150.10, 141.80, 135.09, 130.98, 127.89, 127.09, 124.96, 120.39, 119.58, 95.22, 66.24, 62.38, 30.71, 15.42; HRMS (ESI): C$_{17}$H$_{16}$O$_6$SNa$^+$ (M+Na): 371.0560, found: 371.0561.

3-Hydroxy-6-methoxy-7-(naphthalen-2-ylmethoxy)-1-oxoisochromane-5-carbaldehyde (49). $^1$H NMR (400 MHz, CDCl$_3$) δ 10.53 (s, 1H), 8.03 (s, 1H), 7.92-7.82 (m, 4H), 7.58-7.47 (m, 3H), 5.89 (s, 1H), 5.33 (s, 2H), 4.09 (s, 3H), 3.66-3.44 (m, 2H); $^{13}$C NMR (100 MHz, CDCl$_3$) δ 191.61, 163.50, 158.54, 150.78, 133.21, 133.18, 132.90, 130.77, 128.68, 128.00, 127.75, 127.15, 126.88, 126.48, 126.44, 125.22, 120.64, 119.34, 95.17, 71.47, 62.38, 30.71; HRMS (ESI): C$_{22}$H$_{18}$O$_6$Na$^+$ (M+Na): 401.0996, found: 401.0996.

3-Hydroxy-6-methoxy-1-oxo-7-phenethoxyisochromane-5-carbaldehyde (50). $^1$H NMR (400 MHz, CDCl$_3$) δ 10.48 (s, 1H), 7.85 (s, 1H), 7.37-7.28 (m, 3H), 7.27-7.19 (m, 2H), 5.88 (t, J=3.8 Hz, 1H), 4.33 (t, J=6.6 Hz, 2H), 3.89 (s, 3H), 3.60 (d, J=17.6 Hz, 1H), 3.45 (d, J=17.6 Hz, 1H) 3.17 (t, J=6.6 Hz, 2H); $^{13}$C NMR (100 MHz, CDCl$_3$) δ 191.66, 163.81, 158.27, 150.88, 137.60, 130.53, 128.84, 128.58, 127.04, 126.74, 120.54, 118.69, 95.26, 69.84, 62.17, 35.51, 30.68; HRMS (ESI): C$_{19}$H$_{18}$O$_6$Na$^+$ (M+Na): 365.0996, found: 365.0991.

3-Hydroxy-6-methoxy-1-oxo-7-(2-pyrrol-1-yl-ethoxy)-isochroman-5-carbaldehyde (51). $^1$H NMR (400 MHz, CDCl$_3$) δ 10.48 (s, 1H), 7.82 (s, 1H), 6.75 (m, 2H), 6.15 (m, 2H), 5.88 (m, 1H), 4.35 (m, 4H), 3.90 (s, 3H), 3.59-3.45 (m, 3H); $^{13}$C NMR (100 MHz, CDCl$_3$) δ 191.8, 164.0, 158.6, 150.9, 131.3, 127.3, 120.8, 120.7, 118.8, 108.8, 95.4, 69.0, 62.3, 48.6, 30.7; Elemental analysis calcd (%) for C$_{17}$H$_{17}$NO$_6$·0.25H$_2$O: C, 60.96, H, 5.24, N, 4.23; found: C, 60.64, H, 5.11, N, 4.11.

3-Hydroxy-6-methoxy-1-oxo-7-(3-phenylpropoxy)isochromane-5-carbaldehyde (52). $^1$H NMR (400 MHz, CDCl$_3$) δ 10.52 (s, 1H), 7.82 (s, 1H), 7.29 (t, J=7.4 Hz, 2H), 7.24-7.16 (m, 3H), 5.90 (t, J=3.6 Hz, 1H), 4.13-3.99 (m, 5H), 3.68-3.40 (m, 2H), 2.83 (t, J=7.6 Hz, 2H), 2.19 (p, J=6.7 Hz, 2H); $^{13}$C NMR (100 MHz, CDCl$_3$) δ 191.72, 163.97, 158.28, 151.05, 140.81, 130.46, 128.55, 128.37, 127.01, 126.17, 120.55, 118.69, 95.31, 68.33, 62.25, 32.17, 30.70, 30.64; HRMS (ESI): C$_{20}$H$_{20}$O$_6$Na$^+$ (M+Na): 379.1152, found: 379.1156.

7-(4-(4-Chlorophenyl)butoxy)-3-hydroxy-6-methoxy-1-oxoisochromane-5-carbaldehyde (53). $^1$H NMR (400 MHz, CDCl$_3$) δ 10.50 (s, 1H), 7.83 (s, 1H), 7.24 (d, J=8.4 Hz, 2H), 7.11 (d, J=8.4 Hz, 2H), 5.90 (s, 1H), 4.36 (s, 1H), 4.09 (t, J=6.0 Hz, 2H), 4.04 (s, 3H), 3.61 (dd, J=18.0, 3.8 Hz, 1H), 3.46 (dd, J=18.0, 3.8 Hz, 1H), 2.67 (t, J=7.2 Hz, 2H), 1.92-1.76 (m, 4H); $^{13}$C NMR (100 MHz, CDCl$_3$) δ 191.67, 163.86, 158.26, 151.04, 140.17, 131.64, 130.40, 129.68, 128.48, 127.01, 120.57, 118.64, 95.27, 68.99, 62.22, 34.74, 30.68, 28.45, 27.68; HRMS (ESI): C$_{21}$H$_{21}$$^{35}$ClO$_6$Na$^+$ (M+Na): 427.0919, found: 427.0923; C$_{21}$H$_{21}$$^{37}$ClO$_6$Na$^+$ (M+Na): 429.0890, found: 429.0895.

3-Hydroxy-7-(isopentyloxy)-6-methoxy-1-oxoisochromane-5-carbaldehyde (58). $^1$H NMR (400 MHz, CDCl$_3$) δ 10.51 (s, 1H), 7.85 (s, 1H), 5.90 (t, J=3.8 Hz, 1H), 4.46 (br s, 1H), 4.10 (t, J=6.6 Hz, 2H), 4.07 (s, 3H), 3.61 (dd, J=18.0, 3.8 Hz, 1H), 3.47 (dd, J=18.0, 3.8 Hz, 1H), 1.91-1.79 (m, 1H), 1.75 (q, J=6.7 Hz, 2H), 0.98 (d, J=6.4 Hz, 6H); $^{13}$C NMR (100 MHz, CDCl$_3$) δ 191.77, 164.01, 158.31, 151.17, 130.27, 126.95, 120.50, 118.57, 95.31, 67.77, 62.17, 37.75, 30.69, 25.13, 22.50, 22.46; HRMS (ESI): C$_{16}$H$_{20}$O$_6$Na$^+$ (M+Na): 331.1152, found: 331.1151.

3-Hydroxy-6-methoxy-7-(3-methyl-but-2-enyloxy)-1-oxo-isochroman-5-carbaldehyde (59). $^1$H NMR (400 MHz, CDCl$_3$) δ 10.54 (s, 1H), 7.87 (s, 1H), 5.88 (m, 1H), 5.50-5.46 (m, 1H), 4.64 (m, 2H), 4.07 (s, 3H), 3.64-3.45 (m, 3H), 1.80 (s, 3H), 1.79 (s, 3H); $^{13}$C NMR (100 MHz, CDCl$_3$) δ 191.8, 164.0, 158.6, 150.9, 139.4, 130.4, 127.0, 120.5, 119.2, 118.5, 95.3, 66.1, 62.2, 30.7, 25.8, 18.3; Elemental analysis calcd (%) for C$_{16}$H$_{18}$O$_6$: C, 62.74, H, 5.92; found: C, 62.70, H, 5.94.

3-Hydroxy-6-methoxy-1-oxo-7-(4,4,4-trifluorobutoxy)isochromane-5-carbaldehyde (63). $^1$H NMR (400 MHz, CDCl$_3$) δ 10.55 (s, 1H), 7.89 (s, 1H), 5.97-5.92 (m, 1H), 4.20 (t, J=6.0 Hz, 2H), 4.01-3.95 (m, 1H), 3.68 (dd, J=18.0, 3.8 Hz, 1H), 3.52 (dd, J=18.0, 3.8 Hz, 1H), 2.45-2.30 (m, 2H), 2.24-2.14 (m, 2H); $^{13}$C NMR (100 MHz, CDCl$_3$) δ 191.51, 163.46, 158.27, 150.74, 130.87, 127.28, 126.86 (q, $^1$JCF=274.5 Hz), 120.82, 118.79, 95.18, 67.56, 62.37, 30.74 (q, $^2$JCF=29.4 Hz) 30.68, 22.14 (q, $^3$JCF=3.0 Hz); $^{19}$F NMR (376 MHz, CDCl$_3$) δ −66.29 (t, J=10.8 Hz); HRMS (ESI): C$_{15}$H$_{15}$F$_3$O$_6$Na$^+$ (M+Na): 371.0713, found: 371.0705.

7-Cyclopropylmethoxy-3-hydroxy-6-methoxy-1-oxo-isochroman-5-carbaldehyde (64). $^1$H NMR (400 MHz, CDCl$_3$) δ 10.52 (s, 1H), 7.82 (s, 1H), 5.88 (m, 1H), 4.12 (s, 3H), 3.93 (m, 2H), 3.62-3.48 (m, 2H), 3.10 (s, 1H), 1.32-1.27 (m, 1H), 0.68-0.65 (m, 2H), 0.38-0.35 (m, 2H); $^{13}$C NMR (100 MHz, CDCl$_3$) δ 191.8, 164.0, 158.6, 151.0, 130.4, 127.0, 120.5, 119.0, 95.3, 74.1, 62.2, 43.4, 30.7, 10.2, 3.3; Elemental analysis calcd (%) for C$_{16}$H$_{20}$O$_5$·H$_2$O: C, 58.06, H, 5.85; found: C, 58.02, H, 6.00.

7-Cyclobutylmethoxy-3-hydroxy-6-methoxy-1-oxo-isochroman-5-carbaldehyde (65). $^1$H NMR (400 MHz, CDCl$_3$) δ 10.52 (s, 1H), 7.85 (s, 1H), 5.88 (m, 1H), 4.07 (s, 3H), 4.03 (m, 2H), 3.99-3.88 (m, 1H), 3.62-3.46 (m, 1H), 2.87-2.81 (m, 1H), 2.15 (m, 2H), 1.96-1.87 (m, 4H); $^{13}$C NMR (100 MHz, CDCl$_3$) δ 191.8, 164.0, 158.3, 151.2, 130.3, 126.9, 120.5, 118.7, 95.3, 73.2, 62.1, 34.3, 30.7, 29.7, 24.9, 18.5; Elemental analysis calcd (%) for C$_{16}$H$_{18}$O$_6$: C, 62.74, H, 5.92; found: C, 62.50, H, 5.88.

7-Cyclohexylmethoxy-3-hydroxy-6-methoxy-1-oxo-isochroman-5-carbaldehyde (68). $^1$H NMR (400 MHz, CDCl$_3$) δ 10.52 (s, 1H), 7.85 (s, 1H), 5.88 (m, 1H), 4.07 (s, 3H), 4.03 (m, 2H), 3.99-3.88 (m, 1H), 3.62-3.46 (m, 1H), 2.87-2.81 (m, 1H), 2.15 (m, 2H), 1.96-1.87 (m, 4H); $^{13}$C NMR (100 MHz, CDCl$_3$) δ 191.8, 164.0, 158.3, 151.2, 130.3, 126.9, 120.5, 118.7, 95.3, 73.2, 62.1, 34.3, 30.7, 29.7, 24.9, 18.5; Elemental analysis calcd (%) for C$_{18}$H$_{22}$O$_6$·0.25H$_2$O: C, 63.80, H, 6.63; found: C, 63.62, H, 6.66.

7-Bicyclo[1.1.1]pentanylmethoxy-3-hydroxy-6-methoxy-1-oxo-isochroman-5-carbaldehyde (70). $^1$H NMR (400 MHz, CDCl$_3$) δ 10.52 (s, 1H), 7.81 (s, 1H), 5.87 (m, 1H), 4.11 (s, 3H), 4.03 (s, 2H), 3.64-3.44 (m, 2H), 2.58 (s, 1H), 1.87 (s, 6H); $^{13}$C NMR (100 MHz, CDCl$_3$) δ 191.8, 164.1, 158.2, 151.0, 130.5, 126.9, 120.3, 118.7, 95.4, 69.3, 62.1, 49.9, 42.7, 30.7, 28.7; Elemental analysis calcd (%) for C$_{17}$H$_{18}$O$_6$: C, 64.14, H, 5.70; found: C, 63.91, H, 5.65.

2. Compound Activities

Phosphatases and phosphopeptides: PTPRD, PTPRS and PTPRF phosphatase proteins (>95% purity) that are active in hydrolyzing pNPP substrate were produced in *E Coli* from His-tagged constructs and purified. Purchased PTPRJ and PTPN1 (PTP1B) were purchased from a commercial source. Human GSK30/GSK3α (QLVRGEPNVS-pY-ICSRYYRAPE) phosphopeptide (Pierce/ThermoFisher) were synthesized.

Phosphatase assays: Data for each assay type (3 wells/experimental condition, read using a Spectromax plate reader) was plotted vs time, and results derived from the slopes of linear regions were reported from triplicate independent experiments.

pNPP dephosphorylation to p-nitrophenolate: pNPP substrate was used, 405 nm detection of the dephosphorylation product, controls with 5×10$^{-5}$ M 7-BIA and 18 min incubations as described. See Uhl, G. R.; Martinez, M. J.; Paik, P.; Sulima, A.; Bi, G. H.; Iyer, M. R.; Gardner, E.; Rice, K. C.; Xi, Z. X., Cocaine reward is reduced by decreased expression of receptor-type protein tyrosine phosphatase D (PTPRD) and by a novel PTPRD antagonist. *Proc Natl Acad Sci USA* 2018, 115 (45), 11597-11602. For assays of compound ligands that were likely pseudo-irreversible, 18 min preincubations were also added. For work determining the effect of flavonoids on pNPP hydrolysis, a 96 well half-area plate was prepared by first filling each well to be tested with 18 µL of 50 µM pNPP and 25 uL of running buffer, and 2 µL of DMSO containing the desired concentration of flavonoid and/or peptide. PTPRD phosphatase was diluted 1:50 in a dilution buffer. At the zero time point, 5 uL of this solution was added to each well, and the optical density was measured in 36 second intervals at 405 nm.

Orthophosphate release assays (Promega V2471) used Malachite green and molybdate with spectrophotometric detection of liberated free orthophosphate from test phosphopeptides compared to control and mutant peptides with assessments for the times indicated. Reactions were carried out in a half-area 96-well plate, with three wells dedicated for each time point. To each experimental well, we added a mixture of 18 µL of ultrapure water, 25 L of running buffer (43.4 µM HEPES (pH 7.4), 2.2 µM dithiothreitol, 0.44% acetylated bovine serum albumin, 22.2 µM NaCl, 4.4 µM EDTA), 1 µL of a 10 mM DMSO solution of the desired peptide, and 1 µL of DMSO containing flavonoid or control. 50 µL of molybdate dye mixture was added at t=0, followed by 5 µL of a 1:100 dilution of enzyme in dilution buffer (22.9 µM pH 7.4 HEPES, 1% acetylated bovine serum albumin, 4.6 µM dithiothreitol). Other wells were initiated via the addition of 5 µL of the diluted enzyme mixture @ t=0 and terminated at the desired timepoints by addition of 50 µL of the dye solution. Wells were read @ 605 nm Small molecule in silico docking: The structure of the PTPRD phosphatase D1 (PDB ID 2NV5) was downloaded from the PDB database. See Almo, S. C.; Bonanno, J. B.; Sauder, J. M.; Emtage, S.; Dilorenzo, T. P.; Malashkevich, V.; Wasserman, S. R.; Swaminathan, S.; Eswaramoorthy, S.; Agarwal, R.; Kumaran, D.; Madegowda, M.; Ragumani, S.; Patskovsky, Y.; Alvarado, J.; Ramagopal, U. A.; Faber-Barata, J.; Chance, M. R.; Sali, A.; Fiser, A.; Zhang, Z. Y.; Lawrence, D. S.; Burley, S. K., Structural genomics of protein phosphatases. *J Struct Funct Genomics* 2007, 8 (2-3), 121-40. The model of the PTPRD phosphatase domain was prepared for docking by adding hydrogens, assigning protonation states and optimizing hydrogen bonds using the Schrödinger Protein Preparation Wizard. *Schrödinger Release 2019-4: Protein Preparation Wizard; Epik; Impact; Prime; Glide; LigPrep; Induced Fit Docking protocol*, Schrödinger LLC: New York, NY, 2019; Sastry, G. M.; Adzhigirey, M.; Day, T.; Annabhimoju, R.; Sherman, W., Protein and ligand preparation: parameters, protocols, and influence on virtual screening enrichments. *J Comput Aided Mol Des* 2013, 27 (3), 221-34. The compounds were modeled as covalent binders were prepared in their final, covalently-bound state. All small molecules were prepared using LigPrep to enumerate protonation and tautomerization states and to generate initial 3D structures.

A model of illudalic acid covalent bound to the active site of PTPRD was generated based on Ling, Q.; Huang, Y.; Zhou, Y.; Cai, Z.; Xiong, B.; Zhang, Y.; Ma, L.; Wang, X.; Li, X.; Li, J.; Shen, J., Illudalic acid as a potential LAR inhibitor: synthesis, SAR, and preliminary studies on the mechanism of action. *Bioorg Med Chem* 2008, 16 (15), 7399-409. The catalytic cysteine side chain was removed, and illudalic acid docked using Glide, with a positional constraint of 3.2-4.7 Å from the alpha carbon of the catalytic cysteine allowing identification of poses that contain an atom within 1.5 Å of the position of the catalytic cysteine's sulfur. *Schrödinger Release 2019-4: Protein Preparation Wizard; Epik, Impact; Prime; Glide; LigPrep; Induced Fit*

Docking protocol, Schrödinger LLC: New York, NY, 2019; Friesner, R. A.; Murphy, R. B.; Repasky, M. P.; Frye, L. L.; Greenwood, J. R.; Halgren, T. A.; Sanschagrin, P. C.; Mainz, D. T., Extra precision glide: docking and scoring incorporating a model of hydrophobic enclosure for protein-ligand complexes. *J Med Chem* 2006, 49 (21), 6177-96; Halgren, T. A.; Murphy, R. B.; Friesner, R. A.; Beard, H. S.; Frye, L. L.; Pollard, W. T.; Banks, J. L., Glide: a new approach for rapid, accurate docking and scoring. 2. Enrichment factors in database screening. *J Med Chem* 2004, 47 (7), 1750-9. The cysteine side chain was modeled back in, a covalent bond was formed and the covalent-bound model was subjected to minimization using Prime. *Schrödinger Release 2019-4: Protein Preparation Wizard; Epik, Impact; Prime; Glide; LigPrep; Induced Fit Docking protocol*, Schrödinger LLC: New York, NY, 2019; Jacobson, M. P.; Friesner, R. A.; Xiang, Z.; Honig, B., On the role of the crystal environment in determining protein side-chain conformations. *J Mol Biol* 2002, 320 (3), 597-608; Jacobson, M. P.; Pincus, D. L.; Rapp, C. S.; Day, T. J.; Honig, B.; Shaw, D. E.; Friesner, R. A., A hierarchical approach to all-atom protein loop prediction. *Proteins* 2004, 55 (2), 351-67. After removal of the ligand and the catalytic cysteine, this model was used to generate a receptor to dock 7-BIA and its analogs. These compounds were docked using Glide with its extra precision (XP) protocol and a core constraint of the fused ring.

Tolerability and biodistribution: Tolerability of acute ascending dose (to 20 mg/kg) and two-week alternate day 20 mg/kg regimens of 7-BIA and several congeners in C57 mice (Jax) were tested. For biodistribution studies, we administered 10 mg/kg doses of 7-BIA in 10% DMSO/30% PEG-400 (Fluka)/60% aqueous solutions containing 40% O-cyclodextrin sulfobutyl ether sodium salts (Captisol, Selleckchem) intravenously, intraperitoneally or orally (gavage) to 7-9 week old male Sprague Dawley rats (Vital River, Zhejiang PRC) which were sacrificed using $CO_2$ after varying intervals with plasma sampled via cardiac puncture, brains removed and samples stored at −80° C. Samples were extracted by homogenization in 4 volumes of water (6 sec, H-speed dispersator). 50 μL of homogenate was combined with 5 μL 50% methanol with 0.5% formic acid and 200 μL of acetonitrile containing LL-120001-NX or tolbutamide internal standards (7-BIA or compound 38; 10 ng/mL) was added. Mixtures were vortexed for 1 min and centrifuged at 4000 rpm for 15 mins. 5 or 7.5 ul supernatant samples (plasma and brain, respectively) were analyzed using an AB Sciex Triple Quad 5500 μLC/MS/MS with Analyst 1.6.3 software, negative ion electrospray and multiple reaction monitoring scan mode with 293.10/192.00 for 7-BIA and 327.08/269.00 for the internal standard. Chromatography @ 0.4 ml/min used a Waters Acquity Ultra Performance LC System, Acquity UPLC BEH C18 column (1.7 m, 100×2.1 mm), mobile phase A 1 mM $NH_4OAc$ in water (declining from 90% to 5% and returning to 90% during 4-4.5 min room temperature runs) and mobile Phase B acetonitrile. Results were compared to standard curves generated from plasma or brains from untreated animals spiked with 5-10000 ng authentic 7-BIA or congeners. The lower limit of quantitation was 5 ng/ml.

Table 3 shows $IC_{50}$ values of selected 7-position substituted compounds in inhibiting pNPP hydrolysis by recombinant PTPRD inhibiting PTPRD phosphatase in initial screening assays. For the $R_2$ substituents below, e.g., for compound 1, the $R_2$ substituent represents the formula:

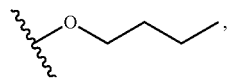 [SMILES: *OCCCC]

where the wavy bond indicates the connectivity point to the compound. The connectivity point for all $R_2$ substituents is at the left of the substituent as shown for the example $R_2$ substituent for compound 1.

TABLE 3

PTPRD INHIBITION

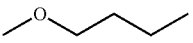

| Cmpd | Identifier | $R_1$ | $R_2$ | AVG PTPRD |
|---|---|---|---|---|
| 1 | 7-BIA | Methoxy | 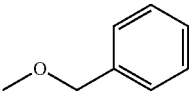 | 2.295 (3.055, 1.495, 2.295) |
| 27 | ZFX-C-16 | Methoxy | 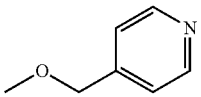 | 1.435 |
| 28 | ZFX-C-100 | Methoxy |  | 228.0 |

TABLE 3-continued
PTPRD INHIBITION
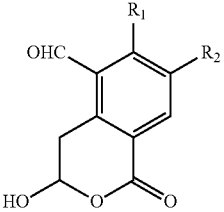
| Cmpd Identifier | | R₁ | R₂ | AVG PTPRD |
|---|---|---|---|---|
| 29 | ZFX-C-90 | Methoxy | 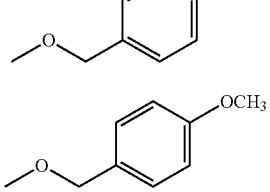 | 3.575 |
| 30 | ZFX-C-99 | Methoxy | 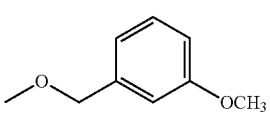 | 10-100 |
| 31 | ZFX-C-125 | Methoxy | 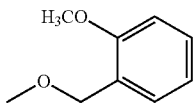 | 4.120 |
| 32 | ZFX-C-127 | Methoxy | 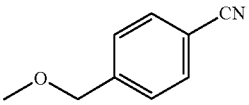 | >100 |
| 33 | ZFX-C-92 | Methoxy | 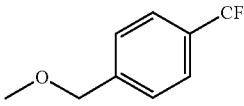 | >10 |
| 34 | ZFX-C-126 | Methoxy | 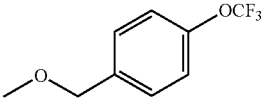 | 10.00 |
| 35 | ZFX-C-140 | Methoxy | 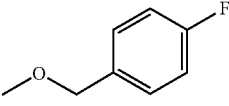 | >50 |
| 36 | ZFX-C-147 | Methoxy | 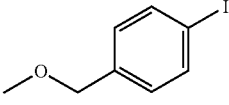 | >500 |
| 37 | ZFX-C-149 | Methoxy | 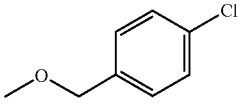 | 100-500 |
| 38 | ZFX-C-114 | Methoxy | | 5.195 |
| 39 | ZFX-C-141 | Methoxy | 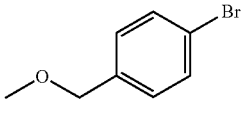 | 2.620 |

TABLE 3-continued
PTPRD INHIBITION
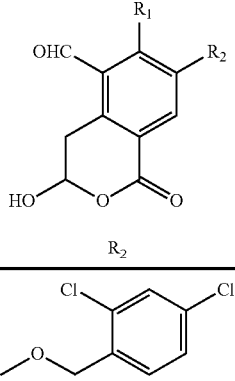
| Cmpd | Identifier | R₁ | R₂ | AVG PTPRD |
|---|---|---|---|---|
| 40 | ZFX-C-154 | Methoxy | 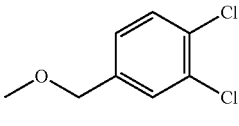 | 0.973 |
| 41 | ZFX-C-113 | Methoxy | 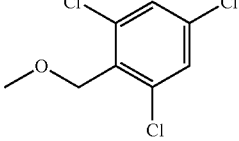 | >10 |
| 42 | ZFX-C-155 | Methoxy | 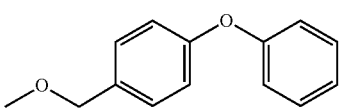 | 2.355 |
| 43 | ZFX-C-135 | Methoxy | 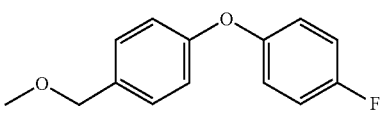 | 1.063 |
| 44 | ZFX-D-66 | Methoxy | 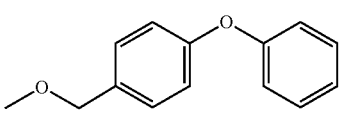 | 4.180 |
| 45 | ZFX-D-111 | n-Butoxy | 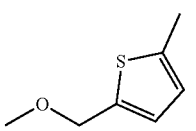 | ND |
| 46 | ZFX-C-172 | Methoxy | 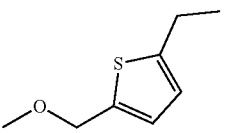 | 4.047 |
| 47 | ZFX-C-186 | Methoxy | 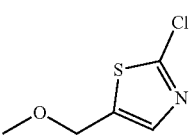 | >50 |
| 48 | ZFX-D-51 | Methoxy | 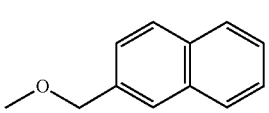 | >50 |
| 49 | ZFX-C-93 | Methoxy |  | 2.054 |

TABLE 3-continued
PTPRD INHIBITION
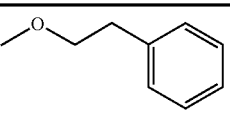
| Cmpd | Identifier | R₁ | R₂ | AVG PTPRD |
|---|---|---|---|---|
| 50 | ZFX-C-98 | Methoxy | 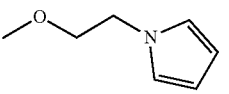 | 10.00 |
| 51 | NHB-1078 | Methoxy | 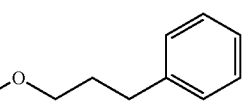 | 3.200 |
| 52 | ZFX-C-86 | Methoxy | 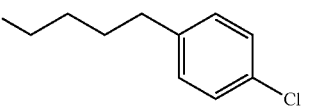 | 1.820 |
| 53 | ZFX-C-181 | Methoxy | 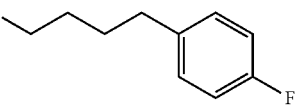 | 3.035 |
| 54 | ZFX-C-182 | Methoxy | 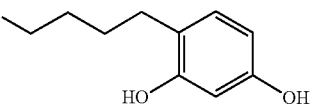 | 1.330 |
| 55 | ZFX-C-30 | Methoxy | 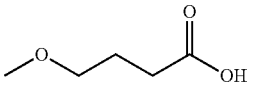 | 2.445 |
| 56 | ZFX-C-32 | Methoxy | 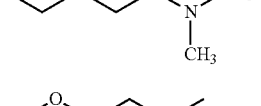 | >10 |
| 57 | ZFX-C-104 | Methoxy |  | >100 |
| 58 | ZFX-C-150 | Methoxy | 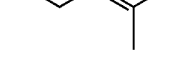 | 2.330 |
| 59 | NHB-1074 | Methoxy | 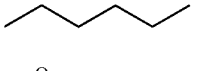 | 2.305 |
| 60 | NHB-1086 | Methoxy | 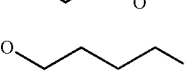 | >100 |
| 61 | ZFX-D-76 | Methoxy | 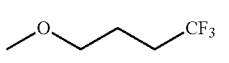 | 31.350 |
| 62 | ZFX-D-88 | Methoxy |  | 2.410 |
| 63 | ZFX-D-87 | Methoxy |  | 4.650 |

TABLE 3-continued
PTPRD INHIBITION
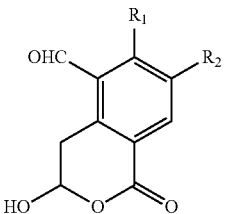
| Cmpd Identifier | | R₁ | R₂ | AVG PTPRD |
|---|---|---|---|---|
| 64 | NHB-1093 | Methoxy | cyclopropylmethoxymethyl | >100 |
| 65 | NHB-1094 | Methoxy | cyclobutylmethoxymethyl | 1.800 |
| 66 | NHB-1109 | Methoxy | cyclopentylmethoxymethyl | 0.689 |
| 67 | ZFX-D-50 | Methoxy | methoxyacetyl-benzofuran | ND |
| 68 | NHB-1128 | Methoxy | cyclohexylmethoxymethyl | 0.86 |
| 69 | SCB-P426 | Methoxy | cycloheptylmethoxymethyl | 1.47 |
| 70 | NHB-1119 | Methoxy | bicyclopentylmethoxymethyl | 3.36(1.1) |

Table 4 shows IC$_{50}$ values (mean+/−SEM of three independent experiments) of 7-position substituted 7-BIA (1) analogs with IC50 values <10 uM in inhibiting pNPP hydrolysis by recombinant PTPRD, PTPRS, PTPRF, PTPRJ and PTPN1 (PTPRB) phosphatases. *denotes compounds whose instability failed to allow valid triplicate experiments. For the R$_1$ substituents below, e.g., for compound 1, the R$_1$ substituent represents the formula:

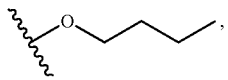 [SMILES: *OCCCC]

where the wavy bond indicates the connectivity point to the compound. The connectivity point for all R$_1$ substituents is at the left of the substituent as shown for example R$_1$ substituent of compound 1.

TABLE 4

Phosphatase Inhibition

| Cmpd | R1 | PTPRD | PTPRS | PTPRF | PTPRJ | PTP1B |
|---|---|---|---|---|---|---|
| 1 | (O-butyl) | 2.27 (0.2) | 1.27 (1) | 3.95 (0.7) | 27.4 (12.6) | 215 (38.6) |
| 27 | (OCH2-phenyl) | 1.64 (0.4) | 1.60 (0.4) | 3.62 (1.5) | 47.17 (8.3) | 171.27 (34.7) |
| 29 | (OCH2-4-Me-phenyl) | 3.80 (1.3) | 3.58 (1.2) | 6.57 (0.3) | 37.7 (11.6) | 148.4 (39.4) |
| 31 | (OCH2-3-OMe-phenyl) | 4.12 | 13.01 | | | |
| 39 | (OCH2-4-Br-phenyl) | 2.62* | 5.00* | 3.82* | 29.90* | |
| 40 | (OCH2-2,4-diCl-phenyl) | 0.98 (0.0) | 1.03 (0.2) | 3.55 (1.2) | 14.61 | 75.96 (5.2) |
| 42 | (OCH2-2,4,6-triCl-phenyl) | 2.47 (0.2) | 2.15 (0.4) | 2.84 (0.8) | 23.57 (10) | 28.87 (3.7) |
| 43 | (OCH2-4-phenoxy-phenyl) | 1.60 (0.29) | 1.34 (0.34) | 3.93 (1.7) | 28.40 | 16.71 (7.11) |
| 44 | (OCH2-4-(4-F-phenoxy)-phenyl) | 2.49* | | | | |

TABLE 4-continued

Phosphatase Inhibition

[Structure: isochromanone core with OCH₃, OHC, R₁ substituents, HO and lactone C=O]

| Cmpd | R1 | PTPRD | PTPRS | PTPRF | PTPRJ | PTP1B |
|---|---|---|---|---|---|---|
| 46 | (methylenoxy-methylthiophene) | 0.92* | 1.40* | 3.50* | 19.83* | |
| 49 | (methylenoxy-naphthalene) | 2.05 (1) | 4.61 (0.8) | 5.87 (1.8) | 33.29 (7.6) | 221.3 (38.4) |
| 50 | (ethoxy-phenyl) | 4.57 (1.4) | 3.03 (1.2) | 4.24 (1) | 54.85 (8.7) | 4.57 (1.4) |
| 51 | (ethoxy-pyrrole) | 3.20* | | | | |
| 52 | (propoxy-phenyl) | 1.82* | 0.93* | 4.41* | | |
| 53 | (butoxy-4-chlorophenyl) | 2.22 (1.02) | 3.09 (0.54) | 5.67 (1.3) | 28.94 (2.8) | 65.74 (16.6) |
| 55 | (butoxy-2,4-dihydroxyphenyl) | 4.45 (2.44) | 2.27 (0.34) | 6.80 (1.1) | 55.5 (14.4) | 319.8 (40.5) |
| 58 | (isopentyloxy) | 2.82 (0.4) | 2.76 (0.5) | 3.87 (0.5) | 51.91 (9.3) | 120.67 (27.6) |
| 59 | (prenyloxy) | 3.21 (1.1) | 1.80 (0.7) | 2.46 (0.1) | 17.83 (9) | >100 |
| 63 | (butoxy-CF₃) | 4.65* | | | | |
| 64 | (methoxy-cyclopropyl) | 4.18* | | | | |
| 65 | (methoxy-cyclobutyl) | 1.80 | 3.36 | 3.03 | | 5.82 |

TABLE 4-continued

Phosphatase Inhibition

| Cmpd | R1 | PTPRD | PTPRS | PTPRF | PTPRJ | PTP1B |
|---|---|---|---|---|---|---|
| 66 | cyclopentylmethoxy | 0.69 (0.1) | 0.61 (0.1) | 1.72 (0.6) | 29.3 (4.8) | 119.2 (53) |
| 68 | cyclohexylmethoxy | 0.86 (0.2) | 1.06 (0.1) | 0.76 (0.0) | 0.56 (0.5) | 100.5 (9.1) |
| 69 | cycloheptylmethoxy | 1.47 (0.2) | 0.77 (0.2) | 1.16 (0.2) | 9.81 (0.3) | 27.1 (7.3) |

Values are mean +/− SEM of results from three independent experiments (each with triplicate samples) for compounds with PTPRD phosphatase IC$_{50}$ values <5 μM.

| # | name | 7-position substituent | PTPRD | PTPRS | PTPRF | PTPRJ | PTP1B |
|---|---|---|---|---|---|---|---|
| 66 | NHB-1109 | cyclopentyl methoxy | 0.69 (0.1) | 0.61 (0.1) | 1.72 (0.6) | 29.31 (4.8) | 119.27 (53) |
| 68 | NHB-1128 | cyclohexyl methoxy | 0.86 (0.2) | 1.06 (0.1) | 0.76 (0.0) | 0.56 (0.5) | 100.53 (9.1) |
| 46 | ZFX-C-172 | (3-methylthiophen-1-yl) methoxy | 0.92* | 1.40* | 3.50* | 19.83* | nd |
| 40 | ZFX-C-154 | (2,4-dichlorophenyl) methoxy | 0.98 (0.0) | 1.03 (0.2) | 3.55 (1.2) | 14.61 (2-8) | 75.96 (5.2) |
| 43 | ZFX-C-135 | (4-phenoxyphenyl) methoxy | 1.60 (0.3) | 1.34 (0.3) | 3.93 (1.7) | 28.4 | 16.71 (7.1) |
| 69 | SCB-P-436 | cycloheptyl methoxy | 1.47 (0.2) | 0.77 (0.2) | 1.16 (0.2) | 9.8 (0.3) | 27.1 (7.3) |
| 27 | ZFX-C-16 | phenyl methoxy | 1.64 (0.4) | 1.60 (0.4) | 3.62 (1.5) | 47.2 (8.3) | 171.27 (34.7) |
| 65 | NHB-1094 | cyclobutyl methoxy | 2.76 (1.2) | 2.85 (0.3) | 4.52 (1.6) | 32.73 (6.5) | 24.10 (13.4) |
| 52 | WFX-C-86 | 3-phenylpropoxy | 1.82* | 0.93* | 4.41* | nd | nd |
| 49 | WFX-C-93 | 2-naphthylethoxy | 2.05 (1) | 4.61 (0.8) | 5.87 (1.8) | 33.3 (7.6) | 221.3 (38.4) |
| 1 | 7-BIA | butyl | 2.27 (0.2) | 1.27 (1) | 3.95 (0.7) | 27.4 (12.6) | 215 (38.6) |
| 55 | ZFX-C-30 | 4-(2,4-dihydroxy phenyl) butoxy | 4.45 (2.4) | 2.27 (0.3) | 6.80 (1.1) | 55.5 (14.4) | 319.8 (40.5) |
| 42 | ZFX-C-155 | (2,4,6-trichoro phenyl) methoxy | 2.5 (0.2) | 2.2 (0.4) | 2.8 (0.8) | 23.57 (10) | 28.9 (3.7) |
| 44 | ZFX-D-66 | [4-(4-fluorophenoxy) phenyl] methoxy | 2.49* | nd | nd | nd | nd |
| 39 | WFX-C-141 | (4-bromophenyl) methoxy | 2.62* | 5.00* | 3.82* | 29.90* | nd |
| 58 | WFX-C-150 | 3-methylbutoxy | 2.82 (0.4) | 2.76 (0.5) | 3.87 (0.5) | 51.91 (9.3) | 120.7 (27.6) |
| 53 | WFX-C-181 | 4-(4-chlorophenyl) butoxy | 2.22 (1.0) | 3.09 (0.5) | 5.67 (1.3) | 28.94 (2.8) | 65.74 (16.6) |
| 51 | NHB-1078 | 2-(N-pyrrolyl) ethoxy | 3.20* | nd | nd | nd | nd |
| 59 | NHB-1074 | prenyloxy | 3.21 (1.1) | 1.80 (0.7) | 2.46 (0.1) | 17.83 (9) | >100 |
| 70 | NHB-1119 | (1.1.1) bicyclopentane | 3.36 (1.1) | 2.09 (0.4) | 3.55 (0.3) | 21.03 (1.8) | 214.97 (38.6) |

-continued

| # | name | 7-position substituent | PTPRD | PTPRS | PTPRF | PTPRJ | PTP1B |
|---|---|---|---|---|---|---|---|
| 29 | WFX-C-90 | (4-methylyphenyl) methoxy | 3.80 (1.3) | 3.58 (1.2) | 6.57 (0.3) | 37.7 (11.6) | 148.4 (39.4) |
| 31 | WFX-C-125 | (3-trifluoromethoxy phenyl) methoxy | 5.64 (1.2) | 3.25 (0.6) | 5.73 (0.7) | 62.82 (10.1) | 202.78 (32.9) |
| 64 | ZFX-D-55 | cyclopropyl methoxy | 4.18* | nd | nd | nd | nd |
| 50 | WFX-C-98 | 2-phenylethoxy | 4.57 (1.4) | 3.03 (1.2) | 4.24 (1) | 54.85 (8.7) | 218.67 (79.1) |
| 63 | ZFX-D-87 | 3-trifluoromethyl propoxy | 4.7* | nd | nd | 108 (13) | nd |

Identification of gross toxicity and no observed adverse effect level (NOAEL) in wildtype and PTPRD knockout mice. We dosed wildtype C57BL/6J (Jax) or PTPRD knockout mice backcrossed for >12 generations on this same C57BL/6J genetic background of both genders by gavage, observed them (GRU and MM) over three days for survival (or inanition sufficient to require euthanasia), weight and obvious changes in behavior in their cages then sacrificed the remaining mice. Gross pathological examination by our veterinarian was followed by major organ histopathology performed by veterinary pathologists. Mice (n=3-6) with doses to 200 mg/kg of both genders revealed no changes in home cage behaviors that were obvious to nonblinded observers familiar with the behaviors of these strains. There were no changes in gross examination. There was no organ toxicity on histopathological examination.

All mice which received 2000 or 1000 mg/kg gavage doses and ⅓ of mice dosed with 400 and 600 mg/kg doses lost weight, reduced their oral intake, developed abdominal distension that was visible on examination during life and revealed distended stomachs and small intestines on necropsies. None of these mice displayed major organ histopathological abnormalities, however. These changes resulted in death (or euthanasia) prior to day 3 of 60% of mice dosed with 2000 mg/kg NHB1109, 40% of the mice dosed with 1000 mg/kg, 33% of mice dosed with 600 mg/kg but none that received 400 or 200 mg/kg doses. Some heterozygous and homozygous PTPRD knockout mice (n=3-4 each) displayed this same constellation of findings that we term "GI syndrome." Mice treated with 2000 mg/kg lost 17 g prior to euthanasia (p=0.001 vs vehicle treated mice which lost 1.7 g on average over three days). Losses vs vehicle treated mice did not reach significance for 1000 (9 g), 600 (1.1 g), 400 (3.4) or 200 (1.3 g) mg/kg NHB 1109 doses. We thus set the mouse no observed adverse effect level (NOAEL) for single NHB1109 doses at 200 mg/kg p.o. based on weight changes and these qualitative observations of gross pathology, histopathology and cage behaviors.

Obesity and metabolic syndrome provide substantial contributions to morbidity and mortality from cardiovascular and metabolic disorders. Mice and humans with reduced PTPRD expression are small and require more palatable/more accessible food following weaning. Treatments with PTPRD phosphatase inhibitors reduce food and water intake. Each of these findings suggests that the disclosed PTPRD phosphatase inhibitors might reduce food intake and serve as therapeutics for obesity and metabolic syndrome.

It will be apparent to those skilled in the art that various modifications and variations can be made without departing from the scope or spirit of this disclosure. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A compound having a structure represented by Formula (I):

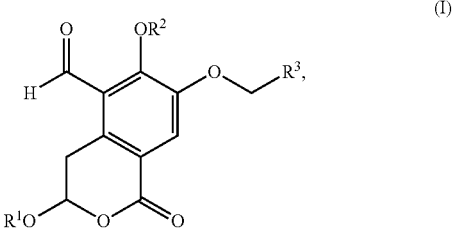

wherein $R^1$ is hydrogen, C1-C4 alkyl, C2-C4 alkenyl, C1-C4 haloalkyl, C1-C4 cyanoalkyl, C1-C4 hydroxyalkyl, C2-C4 alkoxy, C2-C4 haloalkoxy, C1-C4 alkylamino, C1-C4 acetyl, or (C1-C4)(C1-C4) dialkylamino;

$R^2$ is C1-C4 alkyl, C2-C4 alkenyl, C1-C4 haloalkyl, C1-C4 cyanoalkyl, C1-C4 hydroxyalkyl, C2-C4 alkoxy, C2-C4 haloalkoxy, C1-C4 alkylamino, or (C1-C4)(C1-C4) dialkylamino;

$R^3$ is hydrogen or has a structure represented by the formula:

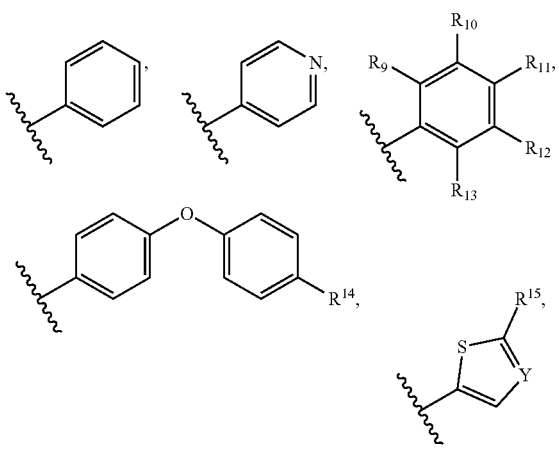

-continued

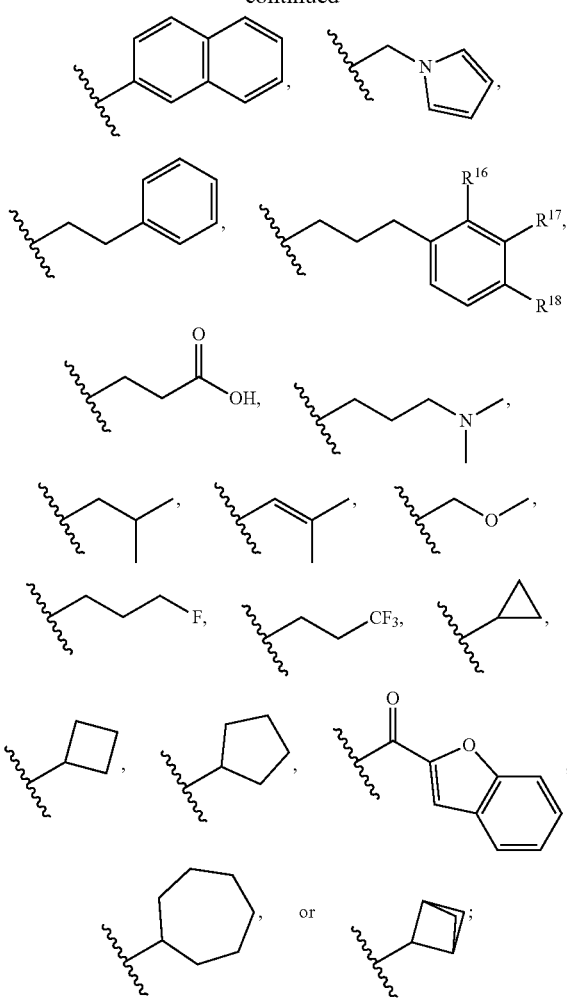

wherein R$^9$-R$^{13}$, when present, are independently hydrogen, methyl, —OCH$_3$, —CN, —CF$_3$, —OCF$_3$, or halide;

R$^{14}$, when present, is hydrogen or halide;

R$^{15}$, when present, is methyl or halide;

Y, when present, is CH or N; and

R$^{16-18}$, when present, are independently hydrogen, hydroxyl, or halide;

or a pharmaceutically acceptable salt thereof, provided that when R$^1$ is hydrogen and R$^2$ is methyl, then R$^3$ is not

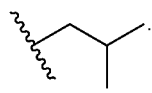 [SMILES: *CC(C)C]

2. The compound of claim 1, wherein:
R$^1$ is hydrogen or C1-C2 alkyl; and
R$^2$ is C1-C2 alkyl.

3. The compound of claim 1, having a structure represented by Formula (II):

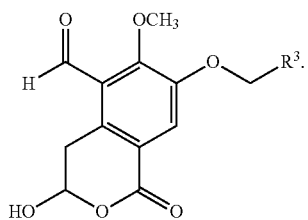

(II)

4. The compound of claim 1, wherein R$^3$ has a structure represented by the formula:

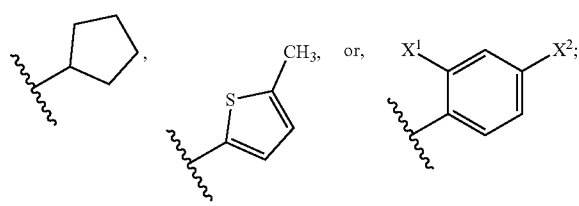

wherein X$^1$ and X$^2$, when present, is independently —Cl, —Br, —I, or —F.

5. The compound of claim 1, having a structure represented by the formula:

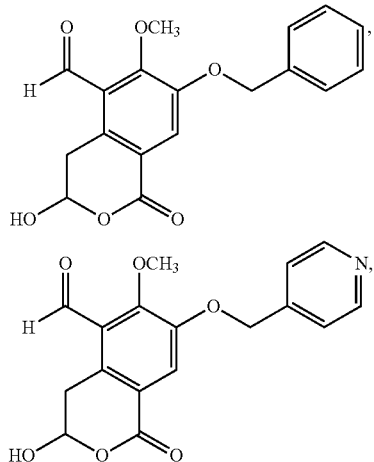

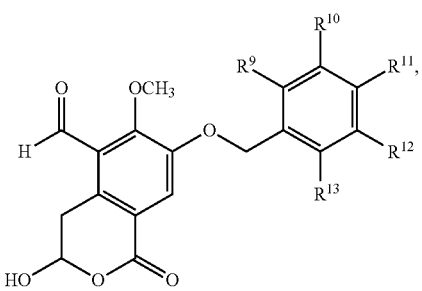

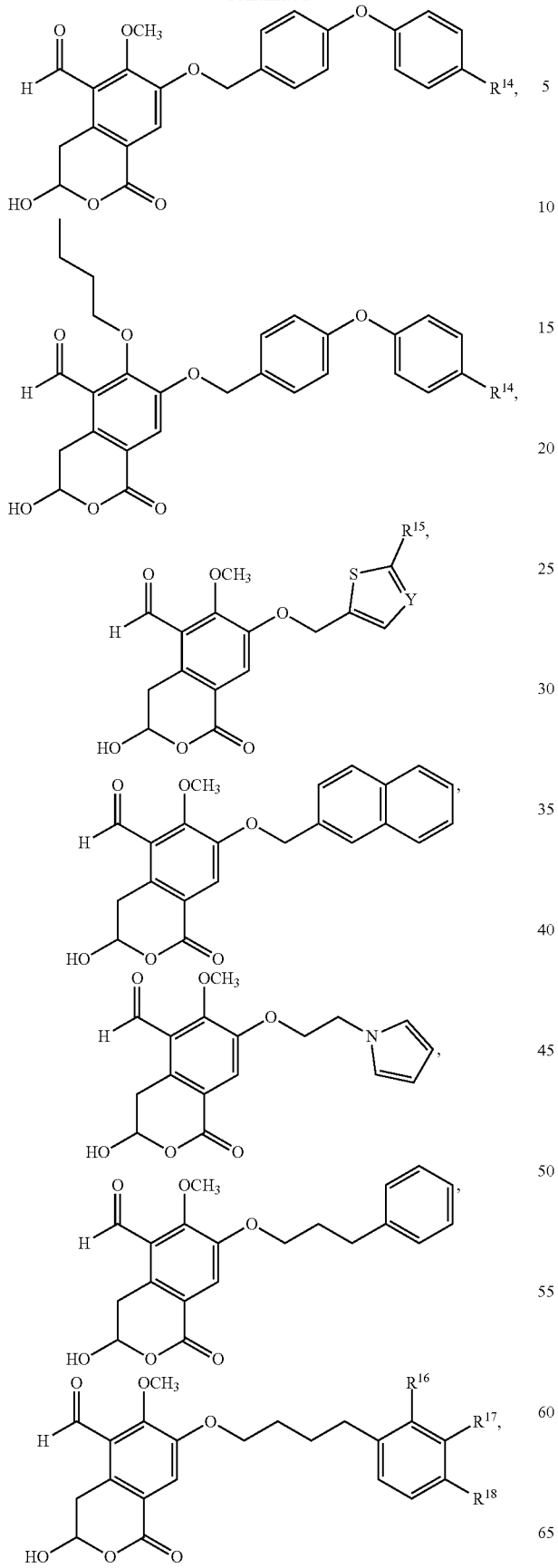
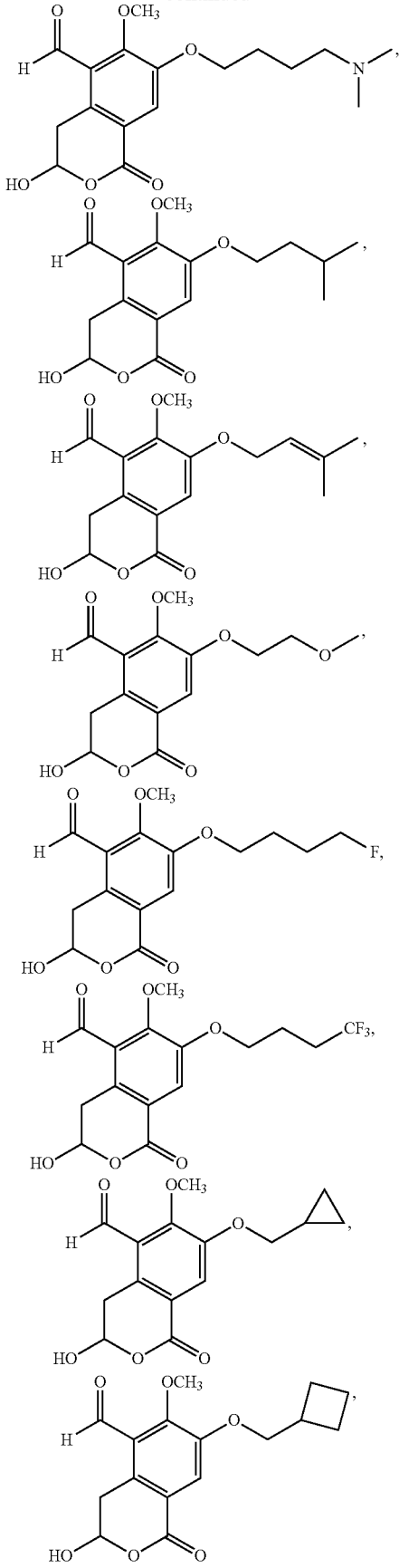

149

-continued

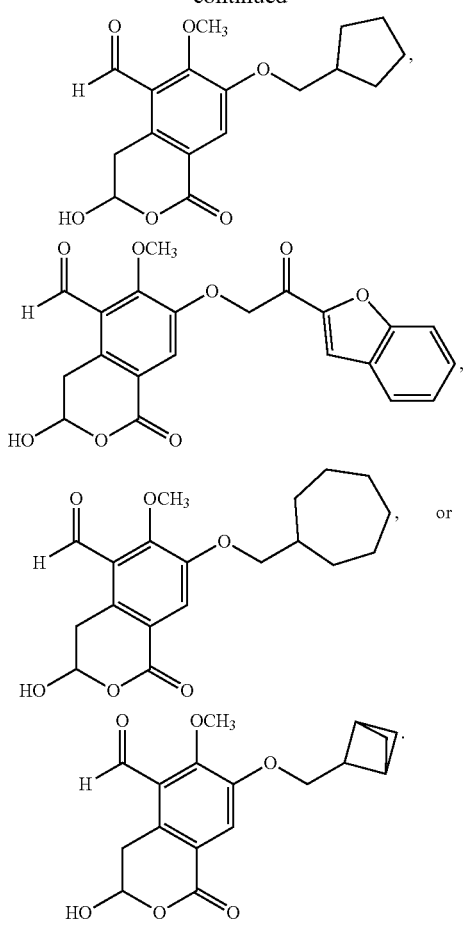

6. The compound of claim 1, having a structure represented by the formula:

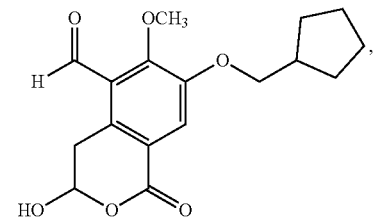 [SMILES: COc1c(OCC2CCCC2)cc2c(c1C=O)CC(O)OC2=O]

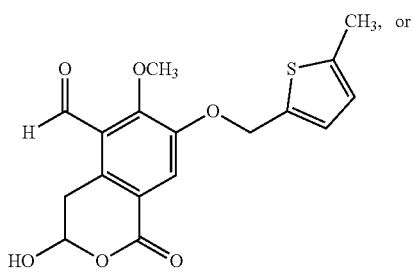

150

-continued

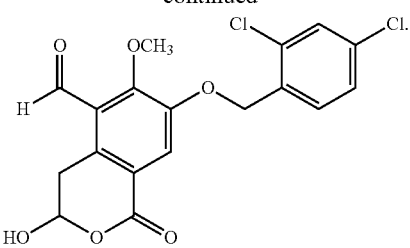

7. The compound of claim 1, having a structure represented by the formula:

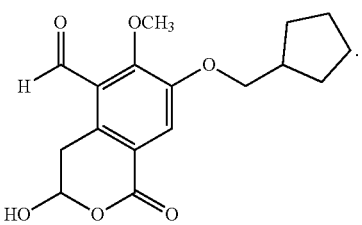

8. A method for treating a disorder responsive to inhibition of receptor-type tyrosine-protein phosphatase delta (PT-PRD), the method comprising administering to a subject in need thereof an effective amount of the compound of claim 1, wherein the disorder is a substance-use disorder, nicotine dependence, obesity, or metabolic syndrome.

9. The method of claim 8, wherein:
R$^1$ is hydrogen or C1-C2 alkyl; and
R$^2$ is C1-C2 alkyl.

10. The method of claim 8, wherein the compound has a structure represented by Formula (II):

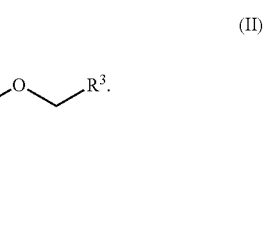

11. The method of claim 8, wherein R$^3$ has a structure represented by the formula:

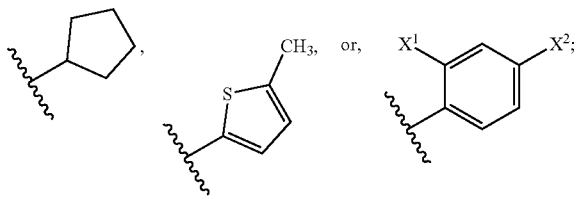

wherein X$^1$ and X$^2$, when present, are independently —Cl, —Br, —I, or —F.

12. The method of claim 8, wherein the compound has a structure represented by the formula:
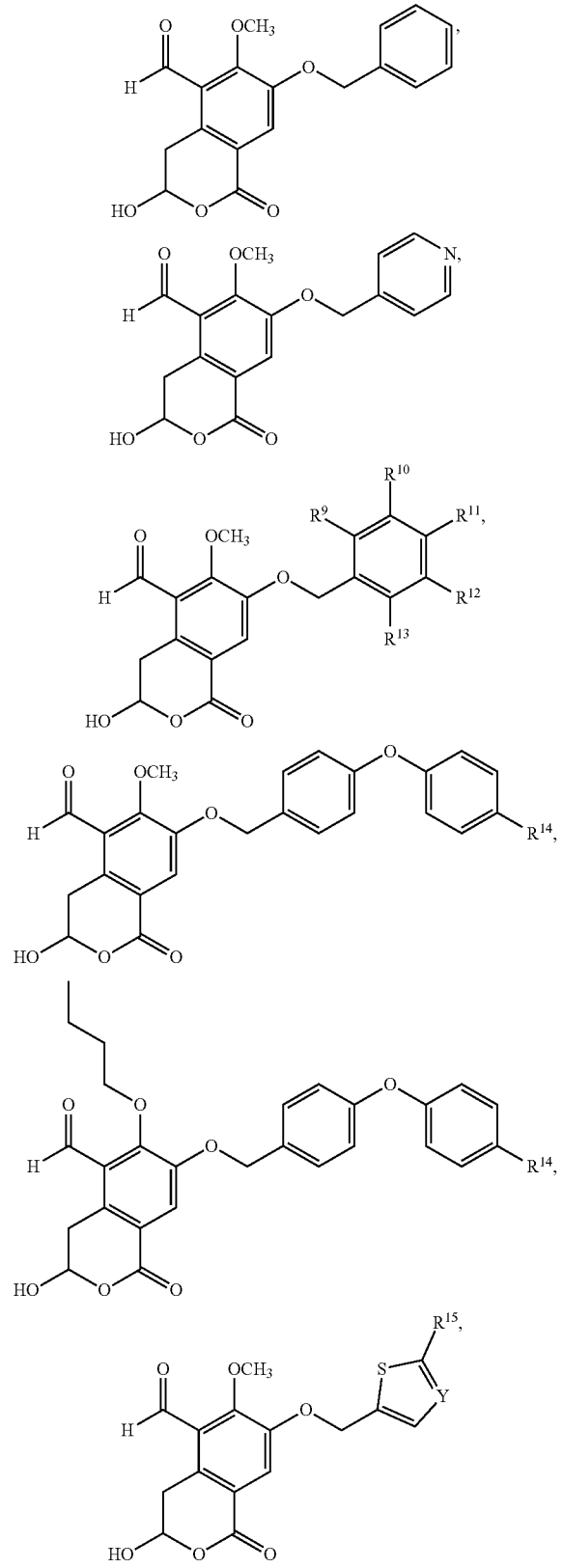
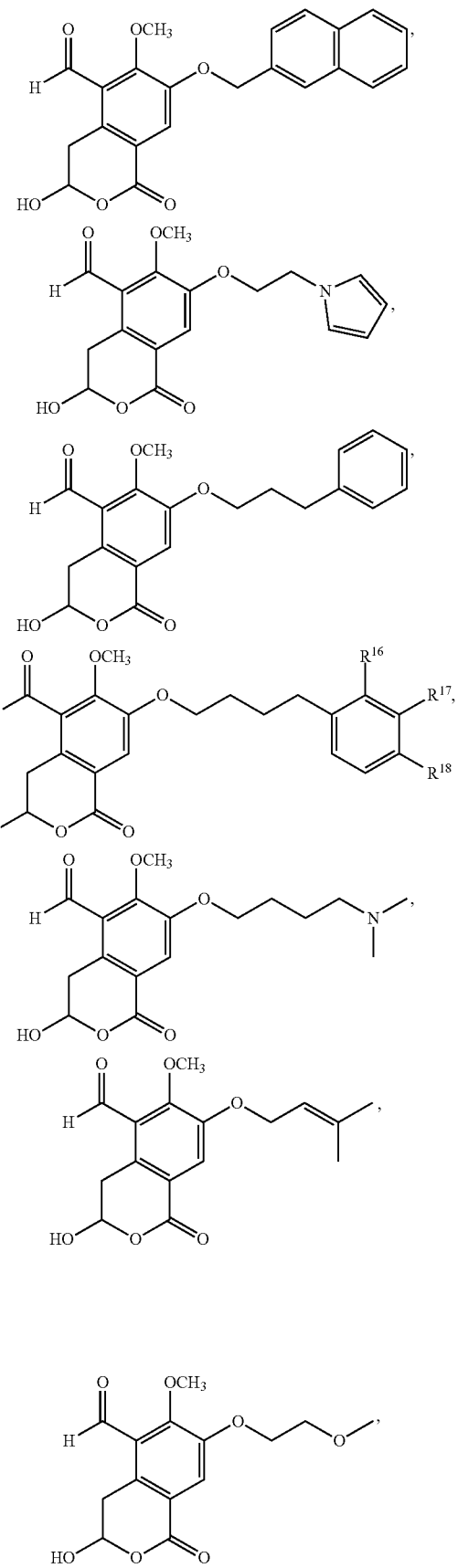

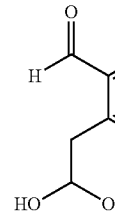
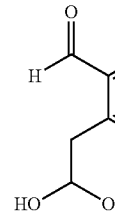
13. The method of claim 8, wherein the compound has a structure represented by the formula:
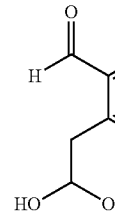
14. The method of claim 8, wherein the compound has a structure represented by the formula:
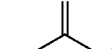
15. The method of claim 8, wherein the substance-use disorder is a stimulant-use disorder.
16. The method of claim 8, wherein the substance-use disorder is an opioid-use disorder.
* * * * *

UNITED STATES PATENT AND TRADEMARK OFFICE
CERTIFICATE OF CORRECTION

PATENT NO. : 11,987,564 B2
APPLICATION NO. : 17/734897
DATED : May 21, 2024
INVENTOR(S) : George Richard Uhl et al.

It is certified that error appears in the above-identified patent and that said Letters Patent is hereby corrected as shown below:

In the Specification

Column 1, please amend Lines 13-16 under the heading "STATEMENT REGARDING FEDERALLY SPONSORED RESEARCH" as follows:
-- "This invention was made with government support under grant number 047713 awarded by the National Institutes of Health. The government has certain rights in the invention." --

Signed and Sealed this
Thirtieth Day of July, 2024

Katherine Kelly Vidal
*Director of the United States Patent and Trademark Office*